(12) United States Patent
Lochhead et al.

(10) Patent No.: US 8,586,347 B2
(45) Date of Patent: *Nov. 19, 2013

(54) SYSTEM AND METHOD FOR DETECTING MULTIPLE MOLECULES IN ONE ASSAY

(75) Inventors: Michael J. Lochhead, Boulder, CO (US); Jeffrey Ives, Arvada, CO (US); Kathryn Todorof, Boulder, CO (US); Charles Greef, Louisville, CO (US); Marie J. Delaney, Boulder, CO (US); Kevin D. Moll, Boulder, CO (US); Kurt R. Vogel, Boulder, CO (US); Keagan B. Rowley, Boulder, CO (US); Evelyn S. Woodruff, Longmont, CO (US); John S. Dunn, Arvada, CO (US); Christopher J. Myatt, Boulder, CO (US); Daniel T. Nieuwlandt, Longmont, CO (US)

(73) Assignee: MBio Diagnostics, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/233,794

(22) Filed: Sep. 15, 2011

(65) Prior Publication Data

US 2012/0071342 A1    Mar. 22, 2012

Related U.S. Application Data

(60) Provisional application No. 61/383,150, filed on Sep. 15, 2010, provisional application No. 61/391,909, filed on Oct. 11, 2010, provisional application No. 61/391,911, filed on Oct. 11, 2010, provisional application No. 61/438,864, filed on Feb. 2, 2011, provisional application No. 61/468,650, filed on Mar. 29, 2011, provisional application No. 61/468,659, filed on Mar. 29, 2011, provisional application No. 61/469,954, filed on Mar. 31, 2011, provisional application No. 61/505,421, filed on Jul. 7, 2011.

(51) Int. Cl.
*C40B 30/04* (2006.01)
*G01N 21/75* (2006.01)
*C12Q 1/68* (2006.01)
*C12M 1/00* (2006.01)

(52) U.S. Cl.
USPC .......... 435/283.1; 435/6.1; 422/82.05; 506/9; 506/39; 385/14

(58) Field of Classification Search
None
See application file for complete search history.

(56) References Cited

U.S. PATENT DOCUMENTS

| 4,608,344 A | 8/1986 | Carter et al. |
| 4,746,179 A | 5/1988 | Dahne et al. |

(Continued)

FOREIGN PATENT DOCUMENTS

| AU | 768800 | 3/1997 |
| CA | 2069539 | 12/1992 |

(Continued)

OTHER PUBLICATIONS

Lochhead, M. et al., Low-Cost Fluorescence Microscopy for Point-Of-Care Cell Imaging, Proc. Of SPIE vol. 7572, 2010, 75720B-1-75720B-6.

(Continued)

*Primary Examiner* — Betty Forman
(74) *Attorney, Agent, or Firm* — Lathrop & Gage LLP

(57) ABSTRACT

A rapid diagnostic system that delivers a panel of serologic assay results using a small amount of blood, serum, or plasma is described. The system includes a disposable cartridge and a reader instrument, based on planar waveguide imaging technology. The cartridge incorporates a microarray of recombinant antigens and antibody controls in a fluidic channel, providing multiple parallel fluorescence assay results for a single sample.

22 Claims, 33 Drawing Sheets

(56) References Cited

U.S. PATENT DOCUMENTS

| | | | |
|---|---|---|---|
| 4,810,658 A | | 3/1989 | Shanks et al. |
| 4,849,340 A | | 7/1989 | Oberhardt |
| 4,852,967 A | | 8/1989 | Cook et al. |
| 4,978,503 A | | 12/1990 | Shanks et al. |
| 5,044,717 A | * | 9/1991 | Levatter .................. 385/33 |
| 5,227,134 A | | 7/1993 | Janata |
| 5,340,715 A | * | 8/1994 | Slovacek et al. .......... 435/6.11 |
| 5,344,784 A | | 9/1994 | Attridge |
| 5,469,264 A | * | 11/1995 | Shigemori ................. 356/417 |
| 5,496,700 A | | 3/1996 | Ligler et al. |
| 5,599,668 A | | 2/1997 | Stimpson et al. |
| 5,677,196 A | | 10/1997 | Herron et al. |
| 5,747,274 A | | 5/1998 | Jackowski |
| 5,832,165 A | | 11/1998 | Reichert et al. |
| 5,843,651 A | | 12/1998 | Stimpson et al. |
| 5,919,712 A | | 7/1999 | Herron et al. |
| 5,959,292 A | | 9/1999 | Duveneck et al. |
| D426,783 S | | 6/2000 | Christensen et al. |
| 6,108,463 A | | 8/2000 | Herron et al. |
| 6,137,117 A | | 10/2000 | Feldstein et al. |
| 6,192,168 B1 | | 2/2001 | Feldstein et al. |
| 6,222,619 B1 | | 4/2001 | Herron et al. |
| 6,242,267 B1 | | 6/2001 | Herron et al. |
| 6,287,871 B1 | | 9/2001 | Herron et al. |
| 6,316,274 B1 | | 11/2001 | Herron et al. |
| 6,356,676 B1 | | 3/2002 | Herron et al. |
| 6,384,912 B2 | | 5/2002 | Kraus et al. |
| 6,395,558 B1 | | 5/2002 | Duveneck et al. |
| 6,485,905 B2 | | 11/2002 | Hefti |
| 6,574,390 B2 | | 6/2003 | Kropp |
| 6,596,545 B1 | | 7/2003 | Wagner et al. |
| 6,611,634 B2 | | 8/2003 | Herron et al. |
| 6,682,942 B1 | | 1/2004 | Wagner et al. |
| 6,686,208 B2 | | 2/2004 | Meusel et al. |
| 6,767,733 B1 | | 7/2004 | Green |
| 6,847,746 B2 | | 1/2005 | Uchiyama |
| 6,861,251 B2 | | 3/2005 | Green |
| 6,951,715 B2 | | 10/2005 | Cunningham et al. |
| 6,961,490 B2 | | 11/2005 | Maisenhoelder et al. |
| 6,979,567 B2 | | 12/2005 | Herron et al. |
| 6,984,491 B2 | | 1/2006 | Mirkin et al. |
| 7,022,515 B2 | | 4/2006 | Herron et al. |
| 7,056,676 B2 | | 6/2006 | Korlach et al. |
| 7,175,811 B2 | | 2/2007 | Bach et al. |
| 7,189,361 B2 | | 3/2007 | Carson et al. |
| 7,202,076 B2 | | 4/2007 | Cunningham et al. |
| 7,236,666 B2 | | 6/2007 | Towle et al. |
| 7,248,361 B2 | | 7/2007 | Kiesel et al. |
| RE39,772 E | | 8/2007 | Herron et al. |
| 7,268,868 B2 | | 9/2007 | Kiesel et al. |
| 7,276,368 B2 | | 10/2007 | Saaski |
| 7,327,454 B2 | | 2/2008 | Cunningham et al. |
| 7,368,281 B2 | | 5/2008 | Mozdy et al. |
| 7,386,199 B2 | | 6/2008 | Schmidt et al. |
| 7,456,953 B2 | | 11/2008 | Schmidt et al. |
| 7,496,245 B2 | | 2/2009 | Saaski |
| 7,522,811 B2 | | 4/2009 | Schmidt et al. |
| 7,529,438 B2 | | 5/2009 | Schmidt et al. |
| 8,300,993 B2 | * | 10/2012 | Moll et al. .................. 385/14 |
| 8,331,751 B2 | * | 12/2012 | Delaney et al. ............ 385/129 |
| 2005/0036728 A1 | | 2/2005 | Braunisch |
| 2005/0048599 A1 | * | 3/2005 | Goldberg et al. ............ 435/34 |
| 2006/0068412 A1 | | 3/2006 | Tang |
| 2006/0188873 A1 | | 8/2006 | Abel et al. |
| 2006/0216696 A1 | * | 9/2006 | Goguen ....................... 435/5 |
| 2007/0231851 A1 | | 10/2007 | Toner et al. |
| 2008/0219616 A1 | | 9/2008 | Wimberger-Friedl et al. |
| 2009/0014360 A1 | | 1/2009 | Toner et al. |
| 2009/0253119 A1 | | 10/2009 | Zhou et al. |
| 2010/0220318 A1 | | 9/2010 | Moll et al. |
| 2012/0088230 A1 | * | 4/2012 | Givens et al. ............... 435/5 |

FOREIGN PATENT DOCUMENTS

| | | |
|---|---|---|
| CA | 2162996 | 11/1994 |
| CA | 2248189 | 9/1997 |
| CA | 2303794 | 3/1999 |
| EP | 0519623 | 8/1998 |
| EP | 0700514 | 11/2001 |
| EP | 1801564 A1 | 6/2007 |
| JP | 2007171182 A | 7/2007 |
| WO | WO0208762 | 1/2002 |
| WO | WO2011026030 | 3/2011 |

OTHER PUBLICATIONS

Lochhead, M. et al. Rapid Multiplexed Immunoassay for Simultaneous Serodiagnosis of HIV-1 and Coinfections, J. Clinical Microbiology, Oct. 2011, pp. 3584-3590.

PCT/US11/051791, International Search Report & Written Opinion mailed Dec. 30, 2011, 15 pages.

PCT/US11/051791, Response to Written Opinion filed Jul. 13, 2012, 36 pages.

Axelrod, "Cell-Substrate Contacts Illuminated by Total Internal Reflection Fluorescence", J Cell Biol (1981).

Axelrod, "Total Internal Reflection Fluorescence Microscopy in Cell Biology", Traffic (2001).

Desmet et al., "Nonthermal Plasma Technology as a Versatile Strategy for Polymeric Biomaterials Surface Modification: A Review", BioMacromolecules (2009).

Duveneck et al., "Planar waveguides for ultra-high sensitivity of the analysis of nucleic acids", Analytica Chimica Acta (2002).

Golden et al., "A comparison of imaging methods for use in an array biosensor", Biosensors Bioelectronics (2002).

Grandin et al., "Waveguide excitation fluorescence microscopy: A new tool for sensing and imaging the biointerface", Biosensors Bioelectronics (2006).

Herron et al., "Fluorescent immunosensors using planar waveguides", SPIE Proceedings (1993).

Ligler et al., "Integrating Waveguide Biosensor", Analytical Chemistry (2002).

Ligler et al., "Array biosensor for detection of toxins", Anal Bioanal Chem (2003).

Liron et al., "Voltage-induced inhibition of antigen-antibody binding at conducting optical waveguides", Biosensors Bioelectronics (2002).

Lundgren et al., "A liquid crystal pixel array for signal discrimination in array biosensors", Biosensors Bioelectronics (2000).

Myers et al., "Innovations in optical microfluidic technologies for point-of-care diagnostics", Lab on a Chip (2008).

O'Brien et al., "The development of immunoassays to four biological threat agents in a bidiffractive grating biosensor", Biosensors Bioelectronics (2000).

Okagbare et al., "Fabrication of a cyclic olefin copolymer planar waveguide embedded in a multi-channel poly(methyl methacrylate) fluidic chip for evanescence excitation", Lab on a Chip (2009).

Okagbare et al., "Fabrication of a cyclic olefin copolymer planar waveguide embedded in a multi-channel poly(methyl methacrylate) fluidic chip for evanescence excitation", Lab on a Chip (2010).

Rowe-Taitt et al., "Evanescent wave fluorescence biosensors", Biosensors Bioelectronics (2005).

Schmidt et al., "Optofluidic waveguides: I. Concepts and implementations", Microfluid Nanofluid (2008).

TIRF Technologies, "Shallow Angle Fluorescence Microscopy", http://www.tirftechnologies.com/tm1003-shallow.php (downloaded Nov. 10, 2010).

Moon, SJ, et al., Integrating Microfluidics and Lensless Imaging for Point-of-Care Testing, Biosens Bioelectron. Jul. 15, 2009; 24(11): 3208-3214.

Moon, SJ et al., Enumeration of CD4+ T-Cells Using a Portable Microchip Count Platform in Tanzanian HIV-Infected Patients, PLoS ONE, Jul. 2011, vol. 6, Issue 7, pp. 1-8.

Zhu, H. et al., A microdevice for multiplexed detection of T-cell-secreted cytokines, Lab Chip, 2008, 8, 2197-2205.

(56) References Cited

OTHER PUBLICATIONS

Yin, D. et al., Integrated optical waveguides with liquid cores, Applied Physics Letters, Oct. 18, 2004, vol. 85, No. 16, pp. 3477-3479.

Singh, K., et al., "Analysis of Cellular Structure by Light Scattering Measurements in a New Cytometer Design Based on a Liquid-Core Waveguide", IEE Proc.-Nanobiotechnol., Feb. 2004, vol. 151, No. 1, pp. 10-16.

Wang, Z. et al., Microfluidic CD4+ T-Cell Counting Device Using Chemiluminescence-Based Detection, Anal. Chem. 2010, 82, 36-40.

Zhu, H. et al., A miniature cytometry platform for capture and characterization of T-lymphocytes from human blood, Analytica Chimica Acta 608 (2008) 186-196.

Cheng, X., et al., A Microchip Approach for Practical Label-Free CD4+ T-Cell Counting of HIVInfected Subjects in Resource-Poor Settings, Acquir Immune Defic Syndr vol. 45, No. 3, Jul. 1, 2007, pp. 257-261, Lippincott Williams & Wilkins.

Cheng, X., et al., A microfluidic device for practical label-free CD4+ T cell counting of HIV-infected subjects, Lab Chip, 2007, 7, 170-178.

Cheng, X., et ai, Enhancing the performance of a point-of-care CD4+ T-cell counting microchipthrough monocyte depletion for HIV/ AIDS diagnostics, Lab Chip, 2009, 9, 1357-1364.

Cheng, x., et al., Cell detection and counting through cell lysate impedance spectroscopy in microfluidic devices, Lab Chip, 2007, 7, 746-755.

\* cited by examiner

FIG. 28
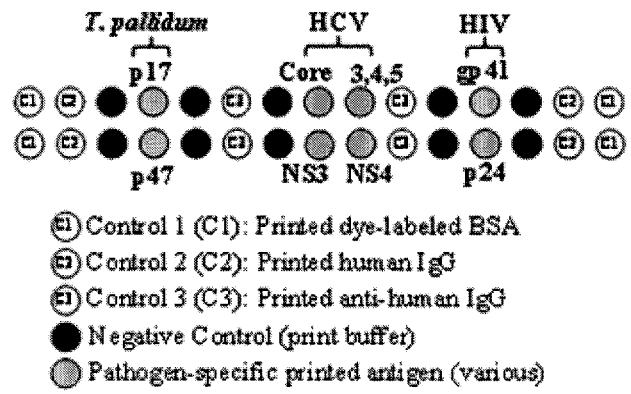
FIG. 29
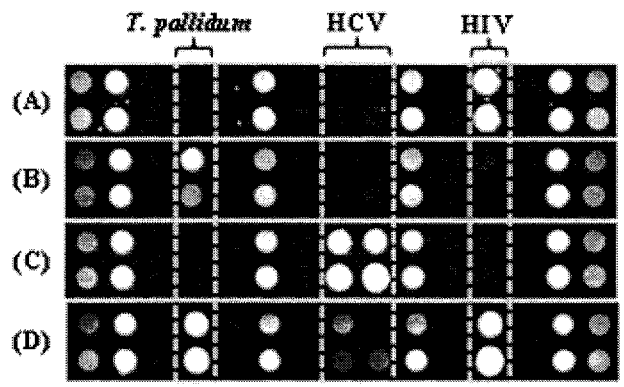
FIG. 30
Background-subtracted, normalized spot intensities.
| | HIV-1 | | T. pallidum | | Hepatitis C Virus (HCV) | | | |
|---|---|---|---|---|---|---|---|---|
| ID | gp41 | p24 | p17 | p47 | Core | NS3 | NS4 | Multi |
| (A) | 3.46 | 1.47 | -0.02 | -0.01 | -0.01 | 0.00 | 0.02 | -0.01 |
| (B) | 0.07 | 0.00 | 0.97 | 0.22 | 0.00 | 0.00 | 0.02 | 0.00 |
| (C) | 0.03 | 0.01 | 0.00 | 0.01 | 2.02 | 2.34 | 3.43 | 1.99 |
| (D) | 2.82 | 2.66 | 2.10 | 2.09 | 0.29 | 0.06 | 0.11 | 0.02 |

Whole Blood

Plasma

| Microarray Antigens | Labeled Antigens Input — HIV p24 | HIV gp41 | T pallidum p17 | T pallidum p47 | Known Sample Serostatus | Experimental Result — HIV | Syphilis |
|---|---|---|---|---|---|---|---|
| (image) | − | − | + | − | NEG | − | − |
| (image) | + | − | − | − | HIV+ | + | − |
| (image) | − | + | − | − | HIV+ | + | − |
| (image) | − | − | + | − | SYPH+ | − | + |
| (image) | − | − | − | + | SYPH+ | − | + |
| (image) | + | + | − | − | HIV+ | + | − |
| (image) | − | − | + | + | SYPH+ | − | + |
| (image) | + | + | + | + | HIV+, SYPH+ | + | + |

FIG. 41

|  | Reference Tests | | | | MBio Results | |
| --- | --- | --- | --- | --- | --- | --- |
| Sample ID | Viral RNA Result | HIV-1 Antibody EIA[1] | Western Blot | | HIV-1 Antibody | HIV-1 Antigen (p24) S/CO |
| Postive RNA; Negative HIV antibody enzyme immunoassay | | | | | | |
| 1 | POS | NEG | | | NEG | 0.2 |
| 2 | POS | NEG | | | NEG | 0.1 |
| 3 | POS | NEG | | | NEG | 1.7 |
| 4 | POS | NEG | | | NEG | 2.2 |
| 5 | POS | NEG | | | NEG | 0.2 |
| Postive RNA; Indeterminate HIV-1 Ab Western Blot | | | | | | |
| 6 | POS | | IND | | IND | 0.4 |
| 7 | POS | | IND | | POS | 0.2 |
| 8 | POS | | IND | | POS | 0.5 |
| 9 | POS | | IND | | NEG | 0.6 |
| 10 | POS | | IND | | IND | 0.3 |
| 11 | POS | | IND | | NEG | 0.1 |
| 12 | POS | | IND | | POS | 0.3 |
| 13 | POS | | IND | | NEG | 0.6 |
| 14 | POS | | IND | | POS | 0.2 |
| 15 | POS | | IND | | POS | 0.4 |
| Postive RNA; Weak Positive HIV-1 Ab Western Blot | | | | | | |
| 16 | POS | | Weak POS | | POS | 0.1 |
| 17 | POS | | Weak POS | | POS | 0.1 |
| 18 | POS | | Weak POS | | POS | 0.1 |
| 19 | POS | | Weak POS | | POS | 0.1 |
| 20 | POS | | Weak POS | | POS | 0.1 |
| 21 | POS | | Weak POS | | POS | 0.3 |
| 22 | POS | | Weak POS | | POS | 0.2 |
| 23 | POS | | Weak POS | | POS | 0.2 |
| 24 | POS | | Weak POS | | POS | 0.6 |
| 25 | POS | | Weak POS | | POS | 0.1 |

[1] EIA = Enzyme Immunoassay

SYSTEM AND METHOD FOR DETECTING MULTIPLE MOLECULES IN ONE ASSAY

RELATED APPLICATIONS

This application claims benefit of priority to U.S. Provisional Patent Application Ser. Nos. 61/383,150, filed Sep. 15, 2010, 61/391,909, filed Oct. 11, 2010, 61/391,911, filed Oct. 11, 2010, 61/438,864, filed Feb. 2, 2011, 61/468,650, filed Mar. 29, 2011, 61/468,659, filed Mar. 29, 2011, 61/469,954, filed Mar. 31, 2011, and 61/505,421, filed Jul. 7, 2011. All of the aforementioned applications, except Application Ser. No, 61/391,911, are incorporated herein by reference.

GOVERNMENT INTEREST

This invention was made with government support under award number AI0068543 awarded by the National Institute of Health. The government has certain rights in the invention.

FIELD OF THE INVENTION

The present disclosure pertains to diagnosis of disease. More particularly, the disclosure relates to the manufacture and use of certain system for rapid detection of multiple disease markers. A system for detection of analytes, including those identified for immunodiagnostic applications, is disclosed. The system includes a cartridge, containing an optical waveguide, and a reader instrument, containing an imaging system and a light source for reading light signal from an analyte-containing cartridge.

BACKGROUND

Early detection of a disease is often critical for successful control and treatment of the disease. Providing accurate, high speed, and low cost blood analysis, infection diagnosis, pathogen detection, or other biological or chemical analyte detection remains a major challenge for health providers and hazardous response teams. This challenge is particularly acute for point-of-care ("POC") environments, where extreme or highly variable environmental conditions are common, testers may have limited training, and practice of test procedures may be significantly different between testers. Such variation is of particular concern for tests offering quantitative or semi-quantitative results, which can critically depend on standardized sample preparation and readout.

A case in point is the diagnosis of infectious diseases such as Acquired Immune Deficiency Syndrome ("AIDS"), which may be spread rapidly among the population if the infection is not detected early. Partly because of their compromised immune system, AIDS patients are usually more vulnerable to a number of co-infections, which account for a significant fraction of human immunodeficiency virus ("HIV") associated morbidity and mortality. Substantial amount of time and resources have been invested in developing a host of HIV screening and diagnostic techniques. However, recurring challenges remain as to how to rapidly identify HIV infection and the various co-infections. Existing diagnoses for multiple co-infections typically require use of a number of different serological diagnostic tools, which render the tests too costly and complex for a POC setting. This problem is exacerbated in countries where resource is limited and HIV prevalence is high.

As an example, the ability to diagnose HIV and opportunistic infections simultaneously at the point-of-care should lead to more effective therapy decisions and improved linkage to care. System utility is demonstrated for a multiplexed HIV-1/syphilis/hepatitis C virus ("HCV") assay using a combination of clinical sample collections. The ability of the disclosed system to provide quantitative read-outs may also lead to more effective data sharing among the various care-providers, commercial vendors, government entities, and non-profit organizations.

Multi-analyte testing for AIDS and its co-infections is important for the development of individualized management of HIV-1 infections and its common co-pathogens. At the time of HIV diagnosis, the standard-of-care may include determination of common co-infections such as HCV, hepatitis B virus ("HBV"), *Toxoplasma gondii* ("*T. gondii*"), *Treponema pallidum* ("*T. pallidum*", causative organism of syphilis), and cytomegalovirus ("CMV"). Co-infection information may be used for treatment (as in the case of *T. pallidum*), vaccinations (as in the case of HBV) and prophylaxis (in the case of *T. gondii*). The multiplexed system described here has the potential to offer a combination of critical tests which detect multiple pathogens in a single assay.

Increased access to anti-retroviral therapy in resource limited settings, and in particular sub-Saharan Africa, has had a major impact on morbidity and mortality from AIDS. By the end of 2009, over 5 million people living in low and middle income countries were receiving anti-retroviral therapy. By most estimates, even before treatment recommendations were revised to encourage the initiation of antiretroviral therapy at higher CD4 cell counts, contemporary anti-retroviral therapy was only reaching 30-40% of those needing therapy. In all likelihood, there will continue to be a substantial gap between the number of people needing antiretroviral therapy and the resources available to treat them. In order to maximize the benefits from the resources available, it is essential that anti-retroviral therapy be delivered as efficiently as possible to those most likely to benefit. A multiplex platform that provides rapid and accurate information about critical co-infections may help prioritize those who should be treated immediately and may also provide guidance on anti-retroviral drug selection.

In addition to anti-viral treatment decisions based on improved co-infection information, the ability to simultaneously detect markers for multiple pathogens in the same sample offers diagnostic advantages. It is well known that HIV infection complicates HCV serodiagnosis. An HIV/HCV co-infection test may help identify infections that were too difficult to characterize at the time of initial screening.

One widely adopted solution for use in primarily qualitative testing (i.e., identifying whether or not an analyte is present at some threshold value) is commonly referred to as a rapid diagnostic test ("RDT"). While a RDT can provide the advantages of low per-test cost, simple operation, and minimal or no required instrumentation, there are also significant limitations. RDTs are often configured to test for only a single analyte, so multiple devices are needed to support co-infection testing, which can be prohibitive from test cost, personnel training, and results management perspectives. Many RDTs are based on chromatographic or lateral flow technology, in which whole or processed blood or other sample, such as urine, is introduced into an absorbent test strip that contains an immunologically-responsive analyte detector. If the analyte is present, a visually-perceptible color change in a portion of the test strip can indicate presence of the analyte and, in certain conditions, user or automated review of the color change can provide a semi-quantitative understanding of analyte concentration. However, such RDTs are limited by the subjective nature of result interpretation by visual inspection and a narrow read time window, both of which require rigorous staff training and quality assurance for result accuracy. Although RDTs that do not require read-out instrumentation can present cost and simplicity advantages, they also present disadvantages, including lack of a link to electronic medical records or laboratory information management system, no automated quality control, no untrained user lockout and no expired lot rejection.

RDTs have had an enormous impact on infectious disease screening programs worldwide over the last decade, and are the backbone of HIV screening efforts. Some in the global health field argue against any type of instrumented test in a point-of-care setting. Arguments against instrumentation hinge primarily on instrument procurement costs and servicing requirements that are not a factor in visually read tests. However, while RDTs provide the advantages of low cost, simple operation, and no required instrumentation, RDTs also have significant limitations. For example, most RDTs require extensive personnel training and lack the capability to be linked to electronic medical records. The nuance of switching between different RDT protocols is also a challenge for care providers.

While more sophisticated analyte detection systems are available, they can be bulky, costly, and require extensive training to calibrate, operate and maintain. For example, POC analyte testing machines that use microfluidics have been disclosed, but many such machines have large numbers of moving parts and complicated structures, including micropumps or pressure sources, require expensive and difficult sample preparation and calibration, or have low throughput. In addition, such systems can require multiple sensors, lasers, or highly skilled technical operators, all of which greatly increase the operation cost of the analyte detection system.

BRIEF DESCRIPTION OF THE FIGURES

FIGS. 28-30 show the array layout, representative images, array layout, and result summary for an exemplary multiplex HIV/Syphilis/HCV assay.

FIG. 41 shows an exemplary analysis summary obtained using the assay system, in accordance with an embodiment.

FIG. 50 shows the results from the HIV antigen and antibody combination assay.

Figure 1:
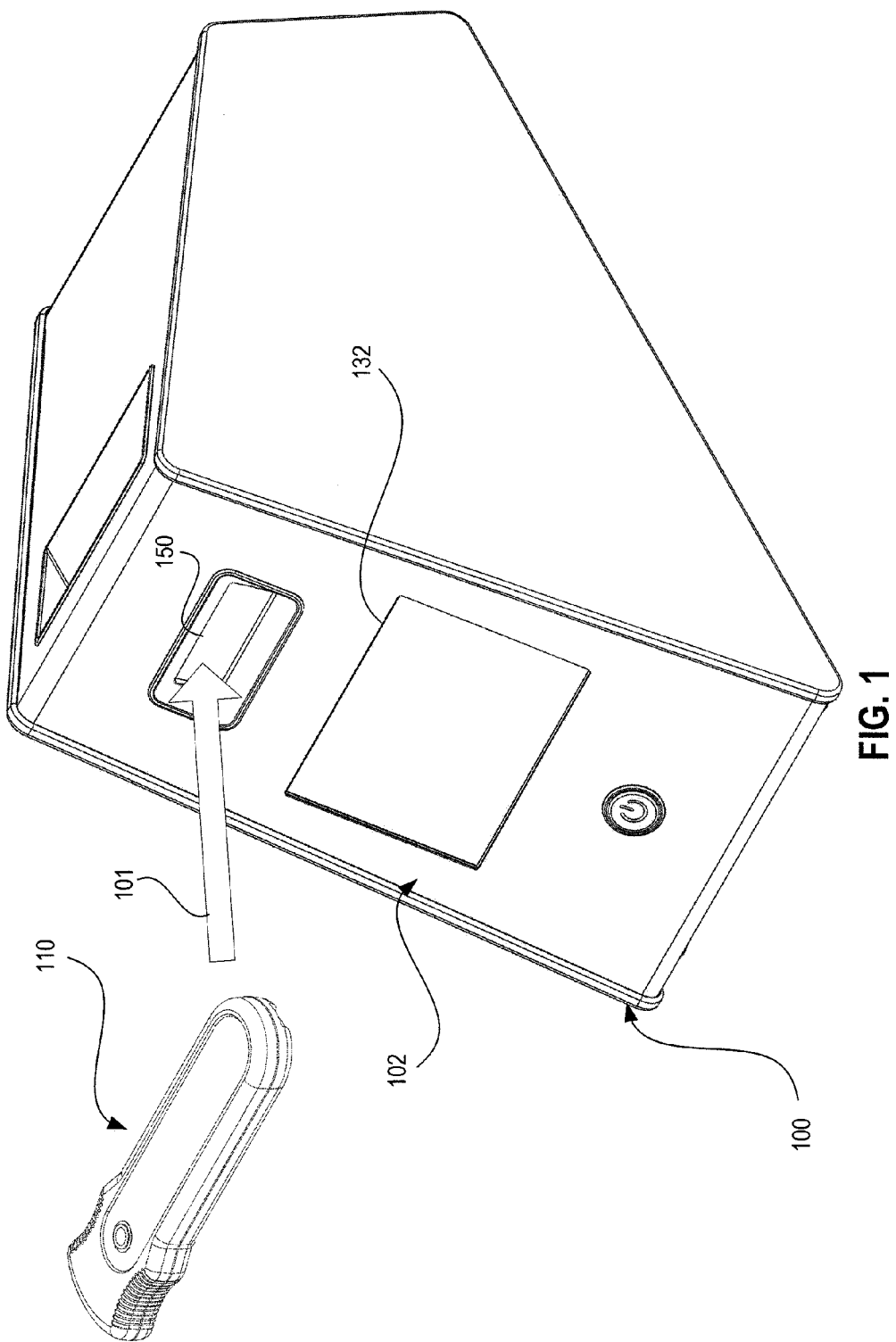
FIG. 1 is a view of a reader instrument with an insertable cartridge, in accordance with an embodiment.

It is noted that, for purposes of illustrative clarity, certain elements in the drawings may not be drawn to scale.

DETAILED DESCRIPTION

The present instrumentalities advance the art by providing a simple diagnostic system that solves many of the problems in the field. The system is capable of delivering a panel of serologic assay results rapidly using a small volume of samples including, but not limited to, whole blood, serum, or plasma.

In one embodiment, the system may contain a device such as a cartridge and a reader instrument capable of reading and processing data obtained from the cartridge. In another embodiment, the disclosed device and system may yield results from multiple fluorescence assays using a single sample. The device (e.g., cartridge) may contain one or more capture molecules such as antigens or antibodies. The device may further contain a fluidic channel to allow for the flow and contact between the sample and the capture molecules. After a sample is loaded onto the device, the analyte(s) in the sample may make contact with the capture molecules. Detection molecules that bind to the analyte(s) may be added to the device to generate signals, which are detected and/or quantified by the reader instrument. In one aspect, the sample may be a fluidic sample from a human, an animal or otherwise obtained from the environment or from an industrial process. In another aspect, the system and method disclosed herein may be employed to deliver a panel of serologic assay results rapidly using a single drop of blood, serum, or plasma sample from a human or an animal. For purpose of this disclosure, a protein may be natural, synthetic or recombinant. The sample suitable for the purpose of the present disclosure may be whole blood sample, serum or plasma.

It is also disclosed here a method for analyzing a sample having one or more analytes, the method may include: (a) adding the sample or a portion thereof to the device as described herein; (b) allowing the sample to incubate with the plurality of capture molecules on the first surface; (c) adding a detection reagent (such as an antibody) to said device, wherein the detection reagent has been labeled with an excitable tag; and (d) allowing the detection reagent to incubate with the first surface. In another aspect, the method may further include (e) providing light from a light source to illuminate the refractive volume of the device, wherein the light is coupled to the planar waveguide via the refractive volume. In another aspect, the method may further include (f) detecting light signal emitted by the excitable tag. The detection reagent may be, for example, an anti-human IgG antibody or an anti-human IgM antibody. An advantageous feature of the disclosed device is that only a small amount of the sample is required for each assay. For instance, about 30 microliters or less of blood sample is sufficient to ensure full contact between the sample and all reaction sites of the device.

In another embodiment, a method is disclosed for analyzing a sample having one or more analytes, wherein the method may include the steps of: (a) adding the sample or a portion thereof to a detection reagent and allowing the detection reagent to bind to target analyte(s) if present; then (b) allowing the sample-detection reagent mixture incubate with the plurality of capture molecules on the first surface. Optionally, (c) applying a wash may be used to remove unbound material from the first surface. In another aspect, the method may further include (d) providing light from a light source to illuminate the refractive volume of the device, wherein the light is coupled to the planar waveguide via the refractive volume. In another aspect, the method may further include (e) detecting light signal emitted by the excitable tag. The detection reagent may be, for example, a fluorescently labeled recombinant antigen, peptide, protein, antibody, or aptamer.

In another embodiment, a device is disclosed for analyzing a sample having one or more analytes. The device may be in the form of a slide, a cartridge or other forms of solid support.

The device may contain a planar waveguide, and a refractive volume. The planar waveguide and the refractive volume may be integrated into one single piece, with the refractive volume being configured for optically coupling light provided by a light source into the planar waveguide. In an embodiment, the refractive volume includes a lens. The planar waveguide may be made of a plastic material that is optically transparent and, additionally, exhibits low auto-fluorescence. Examples of such optically transparent plastic material include, but are not limited to, cyclic olefin polymer, cyclic olefin copolymer, polyolefin, polystyrene, acrylic, polymethylmethacrylate, polycarbonate, and combinations thereof.

In another aspect, the planar waveguide may have at least two surfaces, a first surface and a second surface, wherein the second surface is opposite from the first surface. The plurality of capture molecules may be immobilized to the first surface of the planar waveguide. The device may have an inlet port for addition of sample onto the device, and an outlet port for letting out the sample. The device and the planar waveguide may be configured such that, after the sample is loaded onto the device through the inlet port, the first surface is in contact with the sample.

In another embodiment, the device has a channel to allow the sample to flow therein and to be in contact with the reaction sites and the control sites. The device may further contain a configuration for allowing the sample to be in contact with all reaction sites and control sites.

In another aspect, at least a portion of the first surface may be modified to improve attachment of the capture molecules to the first surface. In another aspect, the modification may provide means for covalently attaching capture molecules to the first surface; exemplary attachment chemistries include, but are not limited to organosilane or polymer formulations providing epoxy groups, aldehyde groups, amine groups, thiol groups, thiol-reactive groups, or succinimidyl esters. In another aspect, the modification may provide a means for immobilizing capture molecules via hydrophobic interactions; exemplary attachment chemistries include self-assembled monolayers with long chain hydrocarbons. In another aspect, the modification may provide means for immobilization of capture molecules via ionic interactions; exemplary attachment chemistries include polycationic polymers, such as poly-L-lysine. In another aspect, the modification may provide means for immobilization of capture molecules via hydrogen bonding or van der Waals interactions. In another aspect, the modification may provide means for immobilization of capture molecules via ligand binding interactions; an exemplary ligand binding system is avidin-biotin. In another aspect, the modification may provide means for improved attachment of capture molecules via a combination of one or more mechanisms, including covalent attachment, hydrophobic interactions, ionic interactions, hydrogen bonding, van der Waals interactions, or ligand binding mechanisms. In another aspect, the modification helps provide a water contact angle of between 60 and 75 degrees on the modified first surface. The modification of the first surface may be performed by using a number of different processes, such as plasma activation, chemical vapor deposition, liquid phase deposition, or surface polymerization of an activation chemistry. Many different chemicals may be used to modify the first surface of the planar waveguide. Examples of such chemicals include but are not limited to organosilane, alkoxysilane, chlorosilane, alkylsilane, epoxy silane, glycidoxy silane, aldehyde silane, aminosilane, or combination thereof. Specifically, glycidoxypropyltriethoxysilane or glycidoxypropyltrimethoxysilane may be used as the modifying chemicals. Example polymer surface modifications include those based on polyethylene glycols, acrylate polymers, dextran, and combination thereof.

The term "capture molecule" is used here to describe any of a variety of molecules that could be attached to the first surface for performing a useful assay. The capture molecules may be a peptide, a polypeptide, a protein, an antibody, an antigen, an aptamer, a polysaccharide, a sugar molecule, a carbohydrate, a lipid, an oligonucleotide, a polynucleotide, a synthetic molecule, an inorganic molecule, an organic molecule, and combination thereof. The terms "polypeptide," "peptide" and "protein" may be used interchangeably in this disclosure. The terms "oligonucleotide," and "polynucleotide" may also be used interchangeably in this disclosure. For purpose of this disclosure, when referring to a polypeptide or a polynucleotide molecule, it is intended that either the full length molecule or a fragment of the full length molecule may be used. Moreover, any mutated forms of a polypeptide (antigen) or the DNA molecule encoding such a polypeptide are also within the scope of the disclosure, if such mutation or mutations do not reside within any epitope of the polypeptide (antigen), or if the mutation or mutations do not substantially decrease the binding affinity between the polypeptide (antigen) and a specific antibody against the polypeptide or a fragment thereof. Plural or singular forms of a noun may be used interchangeably unless otherwise specified in the disclosure. Capture molecules may also be in the form of a molecular mixture. For example, a cell lysate preparation containing a mixture of molecules may be attached to the first surface.

In one embodiment, the first surface of the planar waveguide may contain at least one reaction site (e.g., spot or stripe), wherein each of the reaction site may be formed by printing (i.e., spotting or depositing) a composition onto the first surface. In another embodiment, the first surface of the planar waveguide may have an array (also referred to as a "microarray") of two or more reaction sites. In another aspect, the first surface may contain an array having four, five, six, seven, eight, nine, or ten reaction sites. In yet another aspect, the first surface may contain an array having between two and thirty reaction sites. In yet another aspect, the first surface may contain an array having between two and fifty reaction sites. In yet another aspect, the first surface may contain an array having between two and three hundred reaction sites. Each of reaction sites on the array may be formed by printing a composition onto the first surface. Each composition that is printed onto each reaction site may contain one or more capture molecules. Typically, different reaction sites have different capture molecules. However, for the purpose of having replicate readings, multiple reaction sites may contain identical capture molecules.

For the purpose of this disclosure, the method and system described are based on assays that use fluorescence signal to quantify analyte(s) present in a sample. However, the embodiments described herein may be applicable to assays beyond fluorescence-based signal transduction. In addition, the method and system may also be compatible with luminescence, phosphorescence, and light scattering based signal transduction. In exemplary embodiments, excitable tags may be used as detection reagents in assay protocols. Exemplary tags include, but are not limited to, fluorescent organic dyes such as fluorescein, rhodamine, and commercial derivatives such as Alexa dyes (Life Technologies) and DyLight products; fluorescent proteins such as R-phycoerythrin and commercial analogs such as SureLight P3; luminescent lanthanide chelates; luminescent semiconductor nanoparticles (e.g., quantum dots); phosphorescent materials, and microparticles that incorporate these excitable tags. For the purpose of this disclosure, the term "fluorophore" is used generically to describe all of the excitable tags listed above.

Additionally, the first surface of the waveguide may include a pre-formed feature to serve as, for instance, a reaction site, such as an analyte detection site, a negative control site, a positive control site or a reference site. When two or more reaction sites are present, the array may be arranged such that the reaction sites are spread out on the first surface in rows and columns, with the distance between neighboring column and the distance between neighboring rows being relatively constant within the array.

It is to be recognized that each device may have one or more arrays, and certain reaction sites may be placed on the same surface as the array but outside the array. For instance, certain reference sites or fiducial features for positioning purpose may be placed outside of the normal array arrangement. In another aspect, the first surface of the planar waveguide may also contain a reference site for calibrating the intensity or uniformity of the light provided into the planar waveguide from the light source. The reference site may contain an excitable molecule immobilized on a portion of the first surface and may be located proximal to the array or being part of the array. In another aspect, the reference site may be formed during execution of an assay. By way of example, a human IgG spot printed on the first surface may serve as the reference site in an assay that uses fluorophore-labeled anti-human IgG as the detection reagent.

In another embodiment of the disclosure, the array on the first surface of the waveguide contains one or more negative control sites, wherein at least one of such negative control site is formed by printing onto the first surface a composition that does not contain any molecule that detectably binds to any analyte in the sample. In one aspect, a composition containing only the buffer or solvent may be printed onto the first surface to form a negative control site. In another aspect, a negative control site may contain a molecule that is known to not interact with the analytes of interest in the sample. For instance, for the detection of antibodies against HIV in a human blood sample, a composition that does not contain any molecules known to interact with the human anti-HIV antibodies directly or indirectly may be printed onto the first surface to form one of the negative control sites. Note that the composition for negative control sites also shall not contain molecules that interact with the detection reagent. In an example, at least one of the negative control sites is located at a proximal end of the array that is closest to the inlet port.

In another embodiment of the disclosure, the array on the first surface of the waveguide contains one or more positive control sites, wherein at least one of such positive control site is formed by printing onto the first surface a composition that contains a molecule that detectably binds to one or more analytes in the sample. In one aspect, the composition for the positive control site contains a molecule that consistently binds to one or more analytes in the sample. In another aspect, the composition for the positive control site contains a molecule that binds to the detection reagent. In another aspect, at least one of the positive control sites contains an antibody against human immunoglobulin. In yet another aspect, at least one of the positive control sites contains a human immunoglobulin. In still another aspect, at least one of the positive control sites contains a protein labeled with an excitable tag. In an embodiment, at least one of the positive control sites is located at a distal end of the array farthest from the inlet port.

In another embodiment, the array may have two or more reaction sites and some of the reaction sites may contain identical molecules selected from the plurality of capture molecules for purpose of duplicate reading. In one aspect, each of the reaction sites may contain a different capture molecule selected from the plurality of capture molecules.

In another embodiment, the plurality of capture molecules is a plurality of antigens, wherein the antigens are peptides, polypeptides, or proteins. In one aspect, each of the different molecules on different reaction sites may bind different markers characteristic of different diseases. Thus, the presence or absence of signals from each reaction site may be indicative of whether or not the sample is positive for the particular disease. For example, one reaction site may carry an HIV antigen that binds to anti-HIV antibodies, while another reaction site may carry a HCV antigen that binds to anti-HCV antibodies. Signals from these two reaction sites may indicative of whether or not the sample contains antibodies against HIV and HCV, respectively.

Alternatively, because one disease, pathogen, or other indication may have more than one marker, different reaction sites may carry capture molecules that bind to these different markers characteristic of the same disease, pathogen, or indication. For instance, glycoprotein 41 ("gp41"), p24, gp31, gp160 and gp36 (for HIV-2) are antigens commonly used in HIV-1/2 antibody assay. It may also be beneficial to have an array of reaction sites with one, some, or all of the HIV-1 antigens that are commonly used in the HIV-1 Western Blot: p17, P24, p31, gp41, p51, p55, p66, gp120, and gp160. Sub-type-specific antigens, such as gp41 Type O may also be applicable. Array reaction sites may carry antigens individually, e.g., one site carrying gp41, another site carrying gp120, etc. Alternatively, a reaction site may contain a combination of antigens, such as one site carrying both gp41 and gp160. Signals from reaction sites may be detected and processed to indicate whether or not the sample contains anti-HIV antibodies. Reaction site signals may be further processed to define overall reactivity status for HIV infection.

In another embodiment, reaction site analysis algorithms may be defined within the assay system to define sample status. For example, an analysis algorithm may be used to render a determination of "reactive" or "positive" for a given disease, pathogen, or indication, if any one of a number of reaction sites yields a signal. Alternatively, the analysis algorithm may use some combination of signals on multiple reaction sites to render a determination of "reactive" or "positive" for a given disease pathogen or indication.

In one aspect, signal from each reaction site may be treated as a binary value, such as positive or negative relative to a pre-defined cutoff value of measured signal. In another aspect, signal from each reaction site may be measured as a quantitative signal value.

In another embodiment, the analysis algorithm for determining sample status for a particular disease, pathogen, or indication may be predefined in the firmware or software associated with the reader instrument. In another embodiment, the analysis algorithm may be configurable according to information carried on a given assay device (e.g., cartridge). For example, a cartridge may carry information (e.g., in a barcode affixed to the cartridge) that defines the specific analysis algorithm to be used for that given cartridge. In another embodiment, a given cartridge may carry a code for selecting a particular analysis algorithm that has been pre-loaded on the reader instrument software.

In another embodiment, the analysis algorithm may be based on a reactivity signature or pattern that has been defined by running multiple known samples on the reaction site array. For example, a statistically significant collection of known samples may be considered a "training set" for defining an analysis algorithm.

In another embodiment, the disclosed system may be used to detect infections by at least one microorganism (e.g., virus, bacteria, fungus, parasite, etc.), wherein the microorganism is the causative agent of at least one disease selected from the group consisting of AIDS, syphilis, hepatitis, tuberculosis and combination thereof. In one aspect, two more antigens from the same microorganism may be immobilized to the first surface of the waveguide to form two or more reaction sites. The immobilized antigen may bind to antibodies produced by the host animal or human against the same antigen. Therefore, signals from the two or more reaction sites may indicate the presence or absence of infection by the one microorganism. In another aspect, two more antigens from different microorganisms may be immobilized to the first surface of the waveguide to form two or more reaction sites. Signals from the two or more reaction sites may indicate the presence or absence of infection by the different microorganisms.

In another embodiment, the first surface may contain two or more reaction sites, and at least one of the reaction sites may contain an immobilized antigen, while at least another one of the reaction sites may contain an immobilized antibody. The presence or absence of detectable interactions between the antigen and analytes in the sample may indicate whether or not the sample contain detectable amount of an antibody against this antigen. In the meantime, presence or absence of detectable interactions between the antibody and analytes in the sample may indicate whether or not the sample contain detectable amount of an antigen that may bind the immobilized antibody. The combination of antigen and antibody in the same array may provide an assay with improved levels of accuracy and confidence. For example, it may be beneficial in HIV-1/2 screening assays to measure both antibody reactivity and the presence or absence of viral antigen, such as p24 antigen. Antibody reactivity may be used to identify individuals who have seroconverted to HIV infection. Viral antigen detection may be used to identify individuals in the pre-seroconversion "window phase" of HIV infection, also called the acute infection phase.

In another embodiment, the array may have two or more reaction sites, and each of the two or more reaction sites contains a different capture molecule selected from the group consisting of gp41, p24, gp120, and gp160 antigens of HIV-1; gp36, gp120, and p24 antigens of HIV-2; antibodies against p24 for HIV; p17, p47, p15, and TmpA of *T. pallidum*; core antigen, NS3, NS4, and NS5 of HCV and fragments thereof; antibodies against HCV antigens; antibodies against hepatitis B surface antigen ("HBsAg"); core and surface antigens of HBV; antigens of human herpes virus 8 ("HHV-8"); and combinations thereof.

In another embodiment, the array on the first surface contains a first reaction site and a second reaction site, wherein the first reaction site contains gp41 antigen of HIV-1, while the second reaction site contains p24 antigen of HIV-1. In another embodiment, the array further contains a third reaction site and a fourth reaction site, wherein the third reaction site contains p47 of *T. pallidum*, and the fourth reaction site contains p17 of *T. pallidum*. In yet another embodiment, the array further contains a fifth reaction site and a sixth reaction site, wherein the fifth reaction site contains HCV core antigen, and the sixth reaction site contains an HCV antigen selected from the group consisting of HCV NS3, HCV NS4, HCV NS5, and combination thereof. In another embodiment, the array may contain at least five reaction sites, wherein each of reaction sites contains a different capture molecule selected from the group consisting of p41 antigen of HIV-1, p24 antigen of HIV-1, p17 of *T. pallidum*, p47 of *T. pallidum*, HCV core antigen, and combination thereof.

As an alternative to visually-read RDTs, a disposable cartridge designed to be inserted into a reader instrument that provides qualitative, semi-quantitative, or fully quantitative results may be considered. Such a cartridge may have a defined channel volume through which a sample fluid can flow and, in certain embodiments, analyte presence may be determined by changes in fluorescent properties of reaction in the cartridge. The cartridge may be further configured to support identifying indicia capable of being read in the same field of view as the fluorescent analyte sites. The depth of field of the reader instrument may be such that the fluorescent sites and identifying indicia (e.g., bar codes or alphanumeric symbols) may be simultaneously read.

Figure 2:
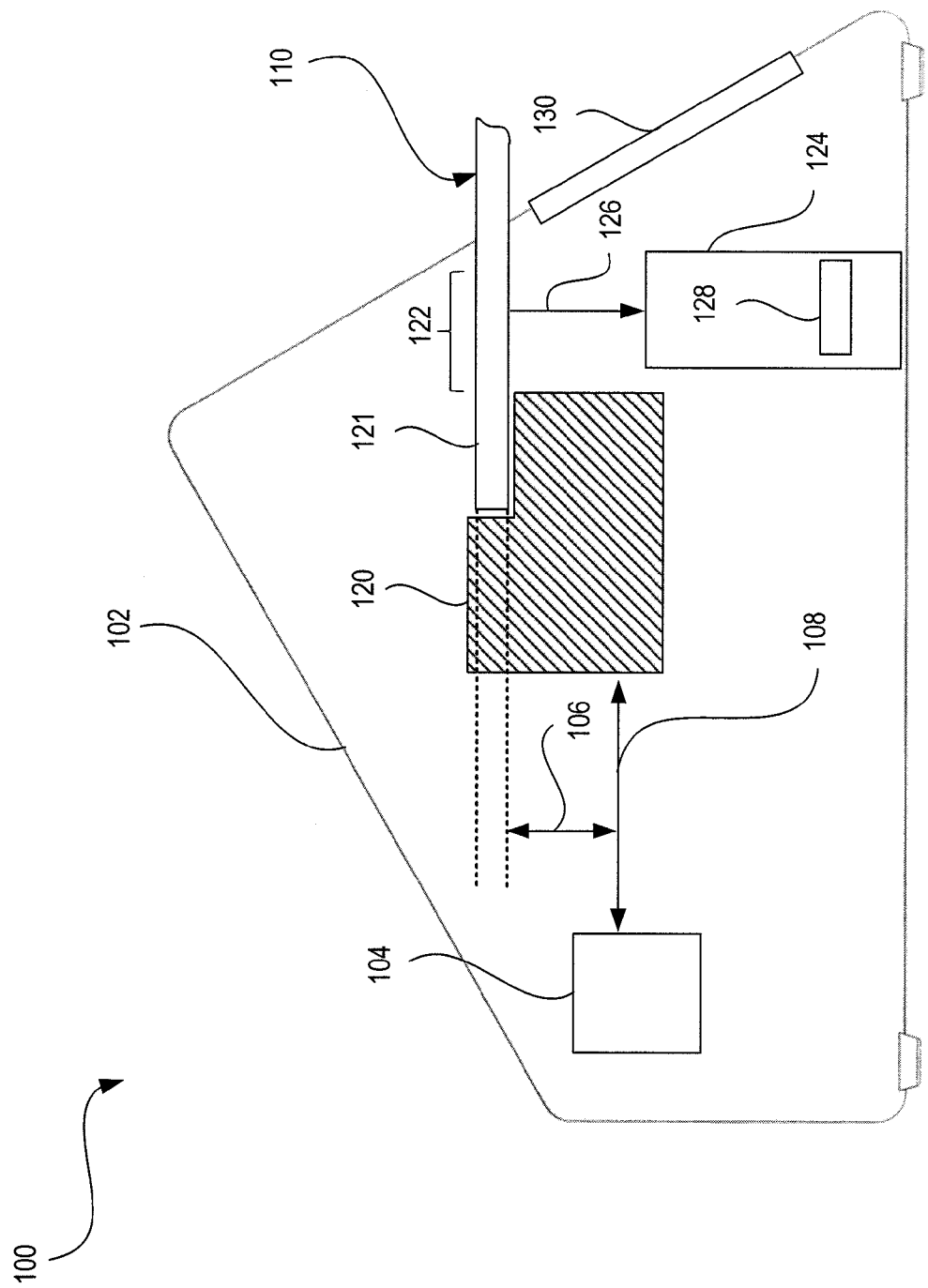
FIG. 2 is a view of a reader instrument with an inserted cartridge, in accordance with an embodiment.

A reader instrument 100 for analyte detection is schematically illustrated in FIGS. 1 and 2. Insertion of a cartridge 110 into reader instrument 100, as indicated by an arrow 101 is schematically illustrated in FIG. 1. Suitable cartridge embodiments are discussed in U.S. Patent Application Ser. No. 61/391,911 entitled "Fluidic Assay Cartridge with Controlled Passive Flow" filed 11 Oct. 2010, as well as U.S. Pat. No. 5,677,196 entitled "Apparatus and Methods for Multi-Analyte Homogeneous Fluoroimmunoassays" to Herron et al., the disclosures of which are both herein incorporated by reference. Reader instrument 100 may include, for example, a housing 102, a screen 132, and an aperture 150 for receiving cartridge 110.

Reader instrument 100 may be used for rapid detection or quantitation of analytes in various settings including, but not limited to, medical clinics in small hospitals, centralized laboratory facilities, public health laboratories, remote and low resource settings, and mobile monitoring units in the United States and internationally. Reader instrument 100 may be a component of a rapid analyte detection system for quickly and accurately identifying target analytes in a sample carried by a cartridge 110. The sample may be a biological or environmentally-derived fluid, sputum, tears, urine, animal or human blood, serum, plasma, or any other sample, which potentially contains an analyte, that is suitably processed before or after placement in cartridge 110. That is, the sample may be a fluidic sample from a human, an animal or otherwise obtained from the environment or from an industrial process. Although shown as a standalone unit, in certain embodiments, the reader instrument may be integrated with other laboratory or processing equipment, including modules for automatic sample preparation, sample storage or containment, or additional laboratory testing.

As may be seen in FIG. 2, reader instrument 100 may be formed from housing 102 that contains a rigidly mounted laser illumination module 104. Laser illumination module 104 may optionally be offset vertically (as indicated by a double-headed arrow 106) or longitudinally (as indicated by a double-headed arrow 108) from cartridge 110. Cartridge 110 includes a refractive volume 120 coupled with a planar waveguide 121. Optionally, refractive volume 120 and planar waveguide 121 may be integrally formed from one material as a single unit, such as disclosed in U.S. Provisional Pat. App. Ser. No. 61/156,586, filed Mar. 2, 2009 and entitled "Waveguide with Integrated Lens," and U.S. patent application Ser. No. 12/617,535, filed Nov. 12, 2009 and also entitled "Waveguide with Integrated Lens," both of which applications are incorporated by reference in their entirety herein. Laser illumination module 104 may include lenses, refractive or reflective elements, spatial or intensity patterning elements, and/or beam diffusers or homogenizers that condition and redirect light emitted from laser illumination module 104. In certain embodiments, laser illumination module may include a rotating beam homogenizer element that reduces speckle and improves reader instrument imaging performance, as discussed in U.S. Patent Application Ser. No. 61/383,150 entitled "Uniform Illumination of a Region by Laser Light Guided in a Planar Waveguide Using a Rotating Diffuser in a Target Imaging System" and filed 15 Sep. 2010, the disclosure of which is herein incorporated by reference. In other embodiments, beam homogenizer element may be omitted, or alternately formed using piezoelectric, acoustic or other time and/or spatially varying optical elements that reduce speckle without requiring large scale rotational, oscillatory, or random motion of optical elements.

In the illustrated embodiment, planar waveguide 121 capable of transmitting laser light directly, or through total internal reflection, to an assay region 122. In one embodiment, cartridge 110 incorporates a microarray of proteins, such as recombinant antigens and antibody controls, in a channel, and is capable of providing multiple parallel fluorescence assay results from a single sample. Cartridge 110 may include a channel, optionally with an inlet port and an outlet port, and may be formed as a single piece or separate pieces that cooperate to define the channel. Cartridge 110 may optionally include multiple parallel channels. For example, multiple channels on the same cartridge may be used to run replicates of the same assay on multiple samples, providing increased throughput. Alternatively, multiple channels on the same cartridge may be used to run different assays on the same sample.

Reader instrument 100 may be configured such that a user is protected from exposure to any potentially dangerous light that is emitted by laser illumination module 104 when a cartridge is fully inserted into an aperture or slot in housing 102, partially inserted, or not inserted at all. Reader instrument 100 may include an interlock switch that electrically disengages light emitting circuitry when cartridge is not inserted or only partially inserted. Reader instrument 100 may be fitted with an opaque door that automatically closes when cartridge is fully extracted from actuator, providing a light tight enclosure. Additional baffles and light blocking elements incorporated into reader instrument 100 or cartridge 110 may further minimize the amount of stray light power that is emitted external to housing 102 when cartridge is inserted.

An imaging system 124 is used to capture images of light signal 126 emitted from assay region 122. A sensor 128, such as a two-dimensional sensor charge coupled device ("CCD") or complementary metal-oxide-semiconductor ("CMOS") sensor, as well as any imaging optics components may be rigidly mounted with respect to laser illumination module 104 and to housing 102. Imaging system 124 may also include one or more imaging optics, such as lenses, refractive or reflective elements, phase-modifying elements, and spatial- or intensity-patterning elements having both sufficient field of view and depth of field to simultaneously image the entire assay region. Alternatively, a variable focus lens may be used so as to enable adjustable focusing on various regions. In certain embodiments, as shown in FIG. 2, imaging system 124 may be oriented with its optical axis perpendicular to the plane of planar waveguide 121. Furthermore, imaging system 124 may be configured so as to image assay region 122 through planar waveguide 121. As later described, in certain embodiments, the field of view may be even larger than detection region 122, allowing capture of fiducial markers, cartridge tracking information, or other desirable cartridge identification indicia (e.g., barcodes).

In the illustrated embodiment, planar waveguide 121 is capable of transmitting laser light directly, or through total internal reflection, to a detection region 122. In one embodiment, cartridge 110 incorporates a microarray of biomarkers, such as printed proteins (e.g., natural, purified, or recombinant antigens, antibodies, and/or controls) in a fluidic channel, and is capable of providing multiple parallel fluorescence assay results from a single sample. Cartridge 110 may include a fluidic channel, optionally with an inlet port and an outlet port, and may be formed as a single piece or separate pieces that cooperate to define channel.

For portable or semi-portable operation, a lightweight, dimensionally small, and low material cost disposable cartridge is useful. The following describes various aspects of one embodiment of such a portable cartridge that is useful in conjunction with a reader instrument, such as that described in co-pending U.S. Patent Application Ser. No. 61/468,659, entitled "Improved Cartridge Reader", filed 29 Mar. 2011, which disclosure is incorporated herein by reference in its entirety. A smaller or larger cartridge or cartridges with other design elements may also be contemplated.

Figure 3:
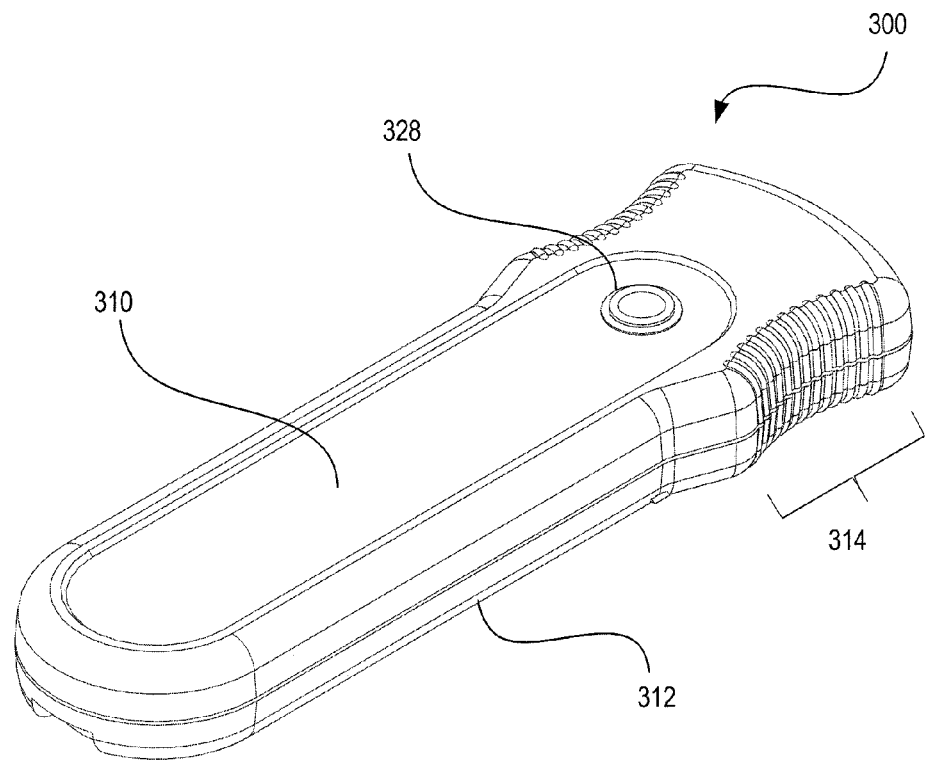
FIGS. 3-11 are various views of a cartridge, in accordance with an embodiment.
Figure 4:
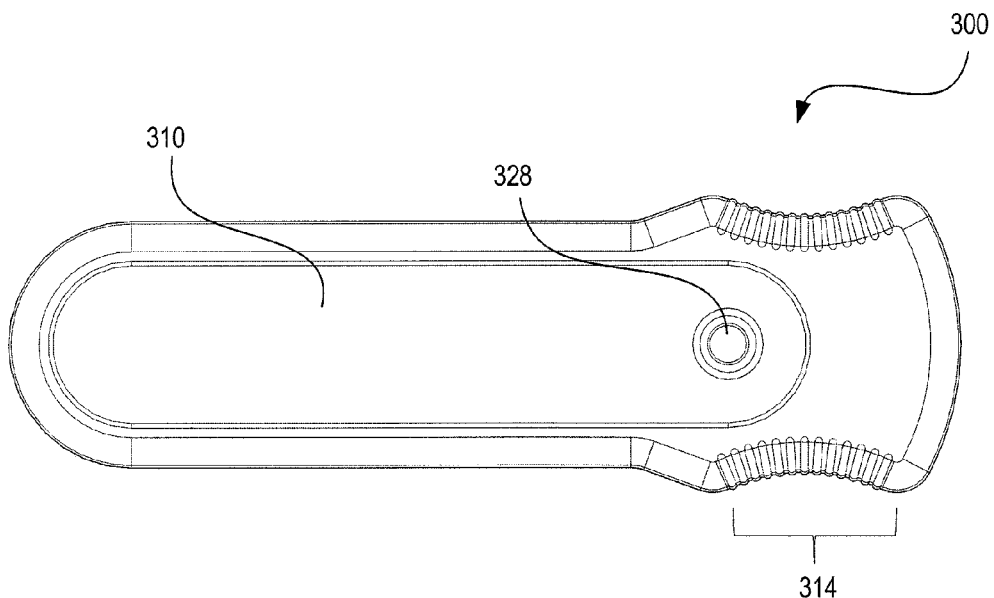
Figure 5:
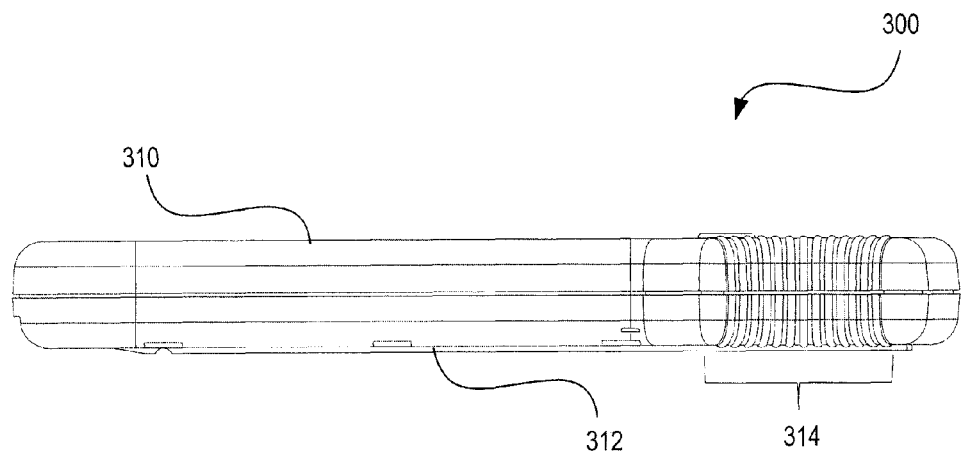
Figure 6:
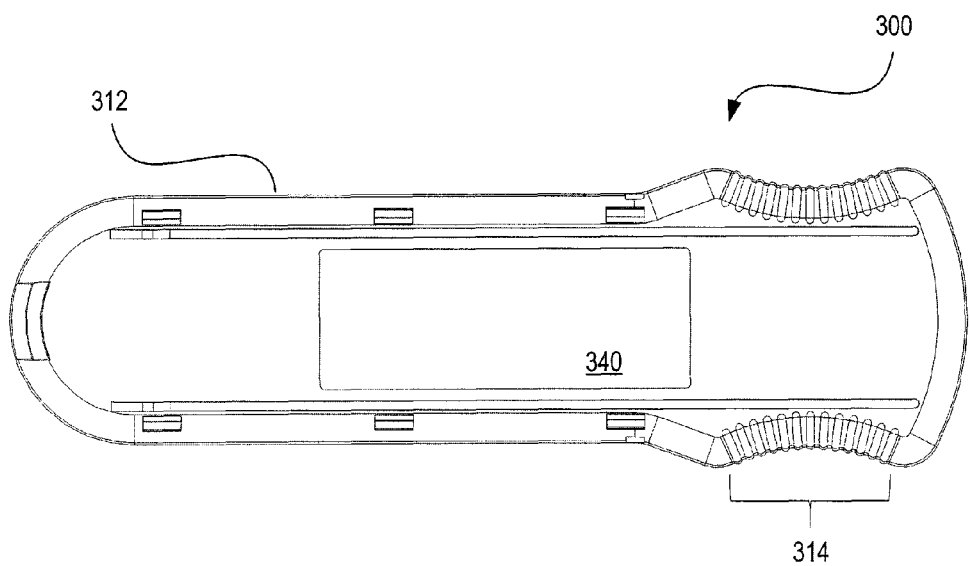

A cartridge 300 is illustrated in perspective view in FIG. 3, top view in FIG. 4, in cross side view in FIG. 5, and in bottom view in FIG. 6. As may be seen in FIGS. 3-5, a cartridge 300 includes an upper piece 310 in snap-fit, press-fit, weld, glue, or other attachment with a matching lower piece 312. Textured grooves 314 in both upper and lower pieces 310 and 312, respectively, improve ease of handling. Cartridge 300 may be formed from a low cost moldable plastic that may be color coded or marked with tracking indicia. In certain embodiments, adhesive strips with alphanumeric labeling, one or two dimensional bar codes, or other tracking indicia may be affixed to cartridge 300. Upper piece 310 may be further configured to accommodate an inlet port 328. As seen in FIG. 6, a window 320 in lower piece 312 allows imaging access therethrough.

Figure 7:
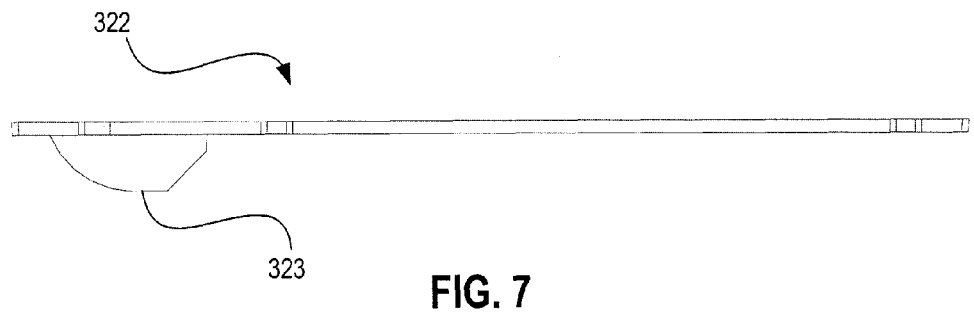
Figure 8:
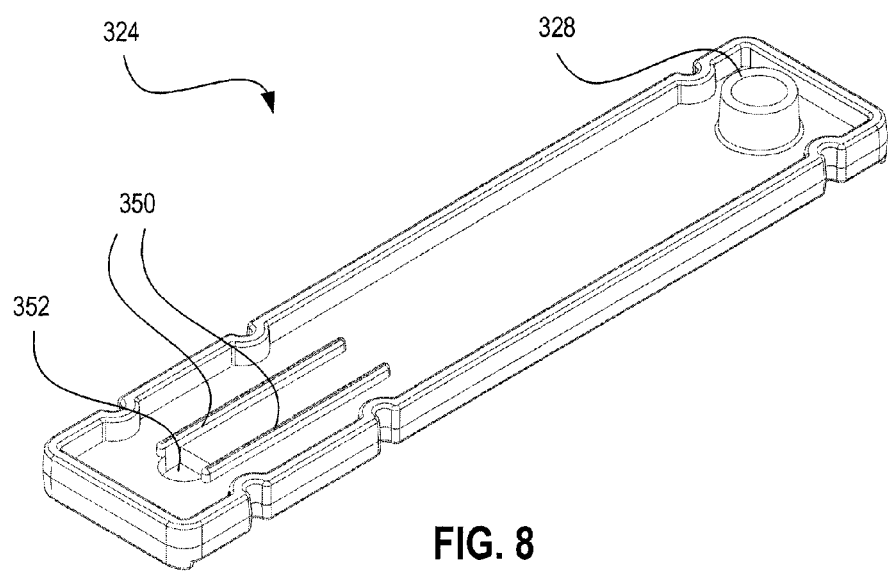
Figure 9:
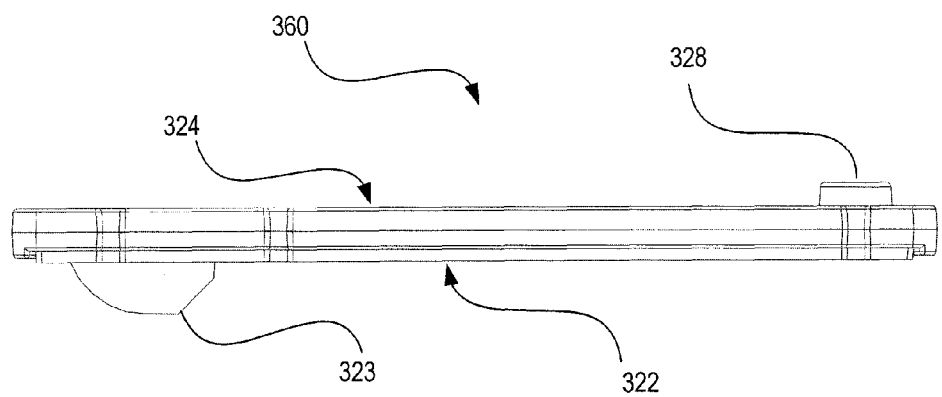

A waveguide 322 with an integral lens 323, as shown in FIG. 7, is held within cartridge 300. As visible in FIGS. 8 and 9, a flow plate 324 with a sample inlet port 328, rails 350 and an outlet port 352, is mated with waveguide 322 using laser welding, chemical or adhesive attachment or other suitable, fluid-tight mating arrangement to form an assembly 360. Assembly 360 may be positioned within cartridge 300, and may further incorporate a wick pad 326 for waste containment, as seen in top and bottom exploded perspective views of FIGS. 10 and 11. A planar surface of waveguide 322 and a groove 370 in flow plate 324 cooperate to define an empty fluidic channel for receiving sample therein. Advantageously, use of waveguide 322 that is separately manufactured from upper piece 310 and lower piece 312 may allow for reduced overall cost and/or increased design flexibility than embodiments in which the waveguide and peripherals (e.g., clamshell or equivalent protective elements) are fabricated together.

Figure 10:
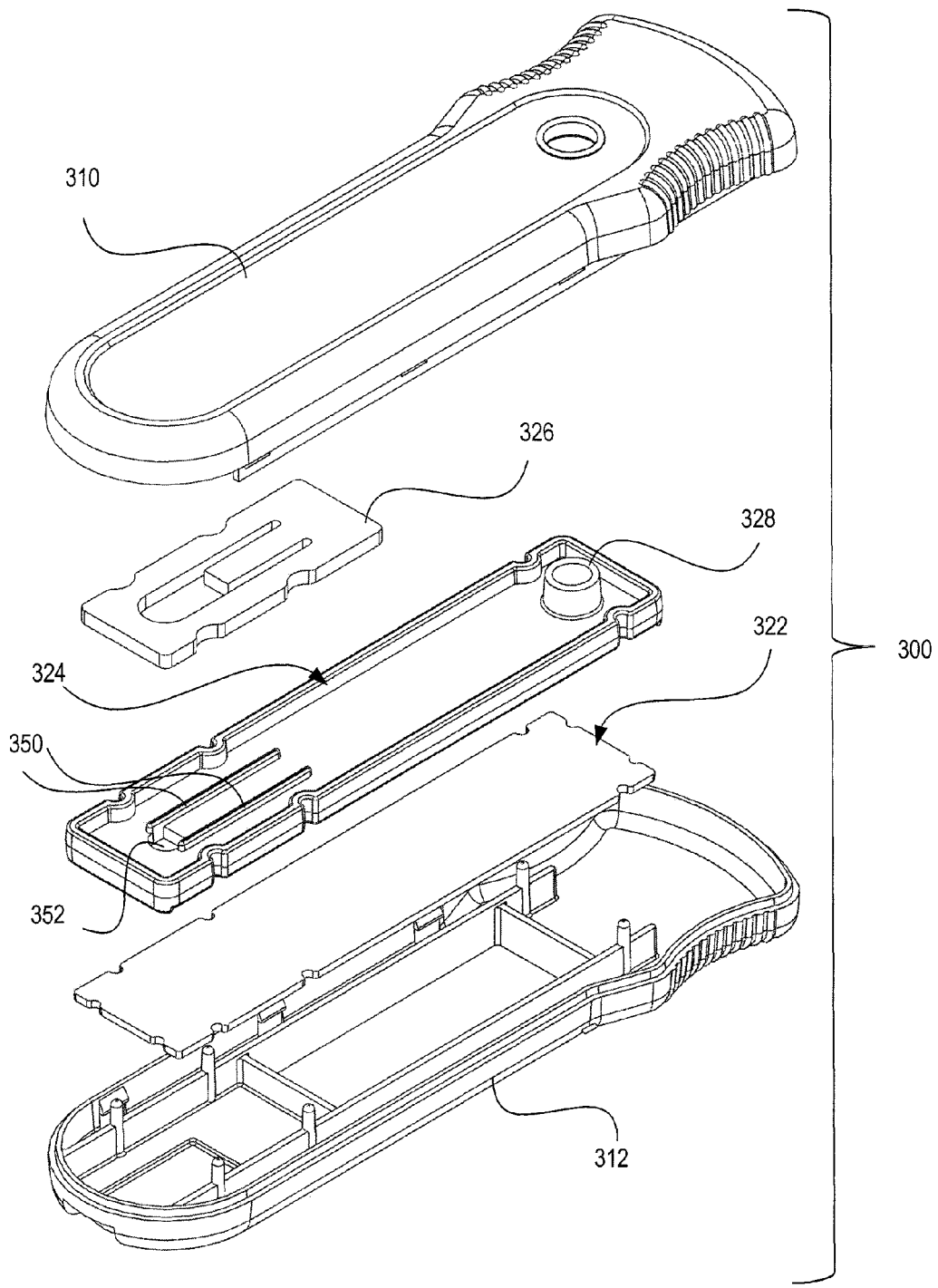
Figure 11:
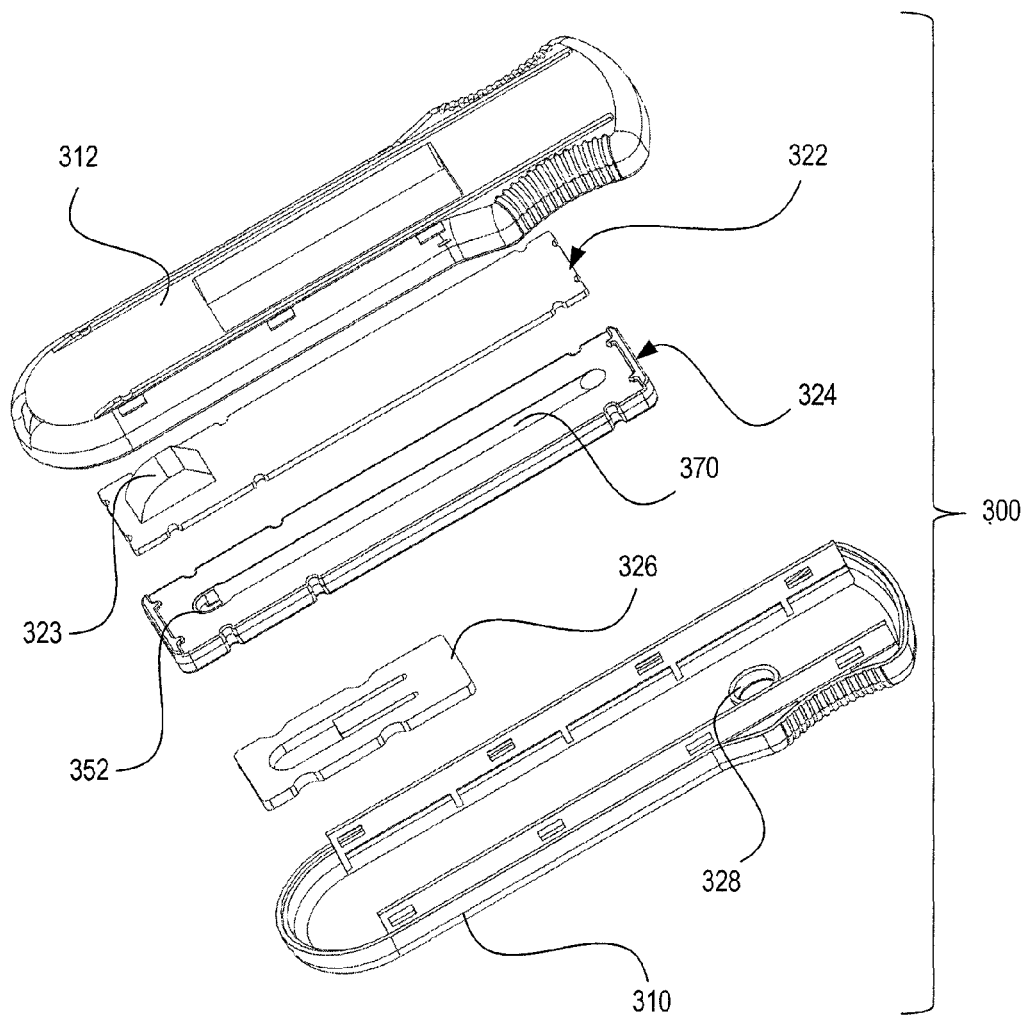

FIG. 10 shows an exploded perspective view of the components of cartridge 300, including, from the top of the figure, upper piece 310, wick pad 326, flow plate 324, waveguide 322, and lower piece 312. FIG. 11 is another exploded perspective view of the components of cartridge 300, this time as viewed with lower piece 312 at the top of the figure, shown here to illustrate the features on the underside of the components, such as integral lens 323 on the underside of planar waveguide 322 and a groove 370 on the underside of flow plate 324. Groove 370, when positioned against planar waveguide 322, defines an empty fluidic channel into which sample may be inserted from input port 328 and flows through the fluidic channel to outlet port 352.

The components include a variety of features, such as notches and protrusions, to assist with the alignment of the components with respect to each other. These alignment features may be modified from those shown in FIGS. 10 and 11 while remaining within the spirit of the present disclosure.

In certain embodiments, the fluidic channel with inlet and outlet ports in the cartridge may be formed when molded components are bonded together. Exemplary bonding methods include, but are not limited to, laser welding, ultrasonic welding, solvent bonding, other chemical bonding methods, or adhesive bonding. In another embodiment, the fluidic channel may be formed when an appropriately cut adhesive gasket joins two cartridge components, as shown in FIGS. 10 and 11. The size of the resulting fluidic channel may be partly determined, for example, by the width of a cut-out for sample containment made in the gasket, as well as the thickness of the gasket itself.

Usefulness and cost effectiveness of a cartridge may be improved by simplifying cartridge construction. In certain embodiments, the cartridge may be constructed by thermally fusing, adhesively attaching, welding or otherwise connecting a planar waveguide with a hermetically-sealed channel defining piece that allows a sample fluid into a channel through an inlet.

In certain embodiments, the cartridge may be marked with identifying indicia such as cartridge parameters, cartridge type, print geometry and layout, print lot, serial number, and expiration date, either by direct printing onto the planar or by attachment of a sticker or the like, printed with identifying information. This marking allows for accurate cartridge identification and tracking based on, for example, one or two dimensional bar codes, RFID readers, or other available tracking technologies. In other embodiments, cartridge affixed RFID, or other tracking technology may be contemplated.

In certain embodiments, the cartridge may include a location for accepting sample-specific identifying information. In another embodiment, the cartridge may have a region for accepting hand-written identifying information. In another embodiment, the cartridge may have a region for applying a label, including barcodes or other sample-specific labels, for identifying the sample being processed on that cartridge.

To further improve usability, the cartridge may be further enclosed in a handling shell. The handling shell may be, for example, a low cost plastic clamshell composed of clamshell elements that snap-fit together. The clamshell may be an opaque, low cost plastic that blocks unwanted transmission of light out of the cartridge. In certain embodiments, clamshell may be color- or pattern-coded to distinguish between diagnostic and/or analyte test types.

The system presented here offers several potential technical advantages over existing technology. Most significant, in an embodiment, is the ability to perform quantitative multiplexed immunoassays on whole blood samples at the point-of-care in a cost effective manner. While some RDTs do offer a degree of multiplexing (see, for example the five band Dual-Path Platform HIV-1/2 test in development by Chem-Bio, Inc.), the system disclosed herein may readily be configured to simultaneously measure 45 different markers or more. The system described here may also provide the advantages of multiple RDTs in a single-protocol, disposable cartridge with automatic quality control features. Further, the system is capable of quantitative output more analogous to laboratory analyzers or enzyme immunoassays ("EIAs").

Referring again to FIG. 2, in one embodiment, cartridge 110 supports a multiplexed fluorescence bioassay including a printed array of biomarkers immobilized on a waveguide contacting surface (e.g., assay region 122) that forms a portion of cartridge 110. Typically, prior to insertion into reader instrument 100, the sample and other assay reagents are added to cartridge 110 according to an assay protocol. After processing, which may take minutes or even hours, the processed cartridge is then inserted into reader instrument 100, which illuminates the waveguide at one or more different exposure times, ranging from milliseconds to seconds. Emitted fluorescence from the biomarker array is optically collected, imaged, and analyzed within a few seconds to minutes. An embedded or external microprocessor may analyze the recorded image.

Advantageously, separation of the slower cartridge processing steps from the faster reader instrument imaging steps allows for a high system throughput, since dozens to hundreds of cartridges may be prepared in batches or parallel processes by one or more technicians and, when ready, may be read relatively quickly by a single technician operating one reader instrument 100.

Overall operation of reader instrument 100 may be controlled through a user interface 130, which may include a touchscreen, barcode reader, operable connection to a separate computer with its own interface (not shown), and/or conventional button, toggles, switches, keyboard, voice/audio control, or other human-machine interface. In diagnostic applications, a cartridge may be processed with a sample according to clinical assay protocol specific to the cartridge being tested. The cartridge is then inserted into the reader instrument. Cartridge parameters (e.g., type, print geometry and layout, print lot, cartridge serial number, and expiration date) may be automatically read, as cartridge parameters may be encoded on the cartridge in the form of a barcode or other information indicia. The sample identifier may be input via user interface 130 into reader instrument 100. Alternatively, the sample identifier may be read automatically. For example, a user may write information on the cartridge by hand or apply identifiers such as barcode stickers to the cartridge, which are in turn imaged or read by the reader instrument. In an embodiment, a sample record, which links cartridge parameters and sample identifier information, may be automatically generated by the reader instrument. Simultaneous cartridge and sample identifier reading in the reader instrument at the time of a measurement provides quality assurance advantages over systems that rely on manual linkage of this information.

Upon insertion, reader instrument may automatically acquire and analyze fluorescent images from imaging system 124 and cartridge 110. This image-derived data may be analyzed to determine qualitative presence of an analyte, semi-quantitative or quantitative evaluation of analyte concentration, or even infection/disease diagnoses. Analysis results may be displayed on user interface 130, such as a front panel display, printed, stored in memory, or transmitted to an information management system for later review.

In addition to operation simplicity, reader instrument 100 has other advantages based on its design. Generally, it is easier to manufacture and maintain devices that have few or no moving parts. Advantageously, reader instrument 100 may be constructed to have few or no moving parts. Laser illumination module 104, and imaging system 124 may be constructed of non-moving parts that are fixed with respect to each other in operation. Shock or drop performance of reader instrument 100 is also improved by limiting the number of moving parts, making reader instrument 100 more suitable for use in field or portable applications.

Various other aspects and alternative embodiments of the described reader instrument may be better understood after consideration of the following non-limiting examples. The reagents, chemicals and other materials are presented as exemplary components or reagents, and various modifications may be made in view of the foregoing discussion within the scope of this disclosure.

Example 1

A Portable Reader Instrument

Figure 13:
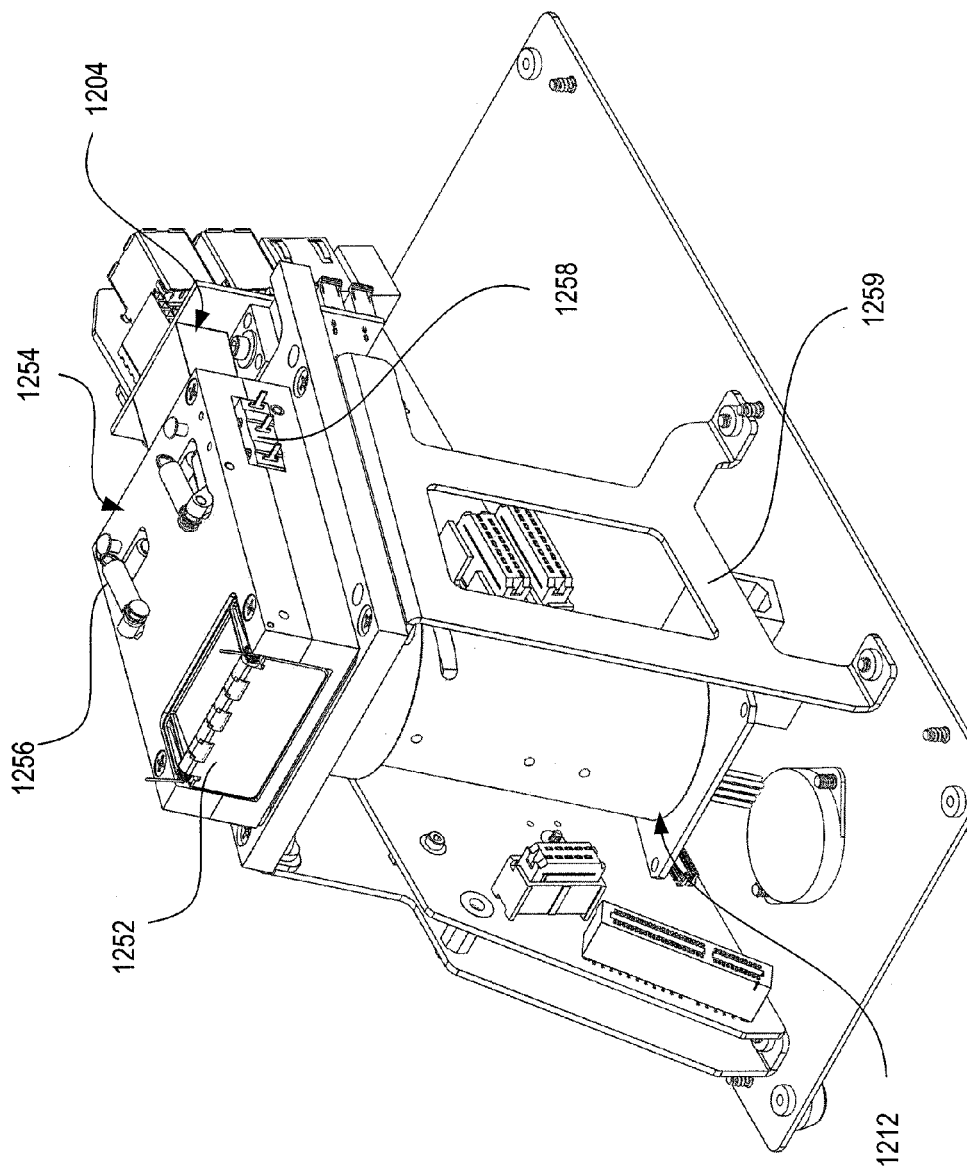
FIG. 13 is a view of an embodiment of a reader instrument with more of the housing removed to reveal positioning of an imaging system therein.
Figure 14:
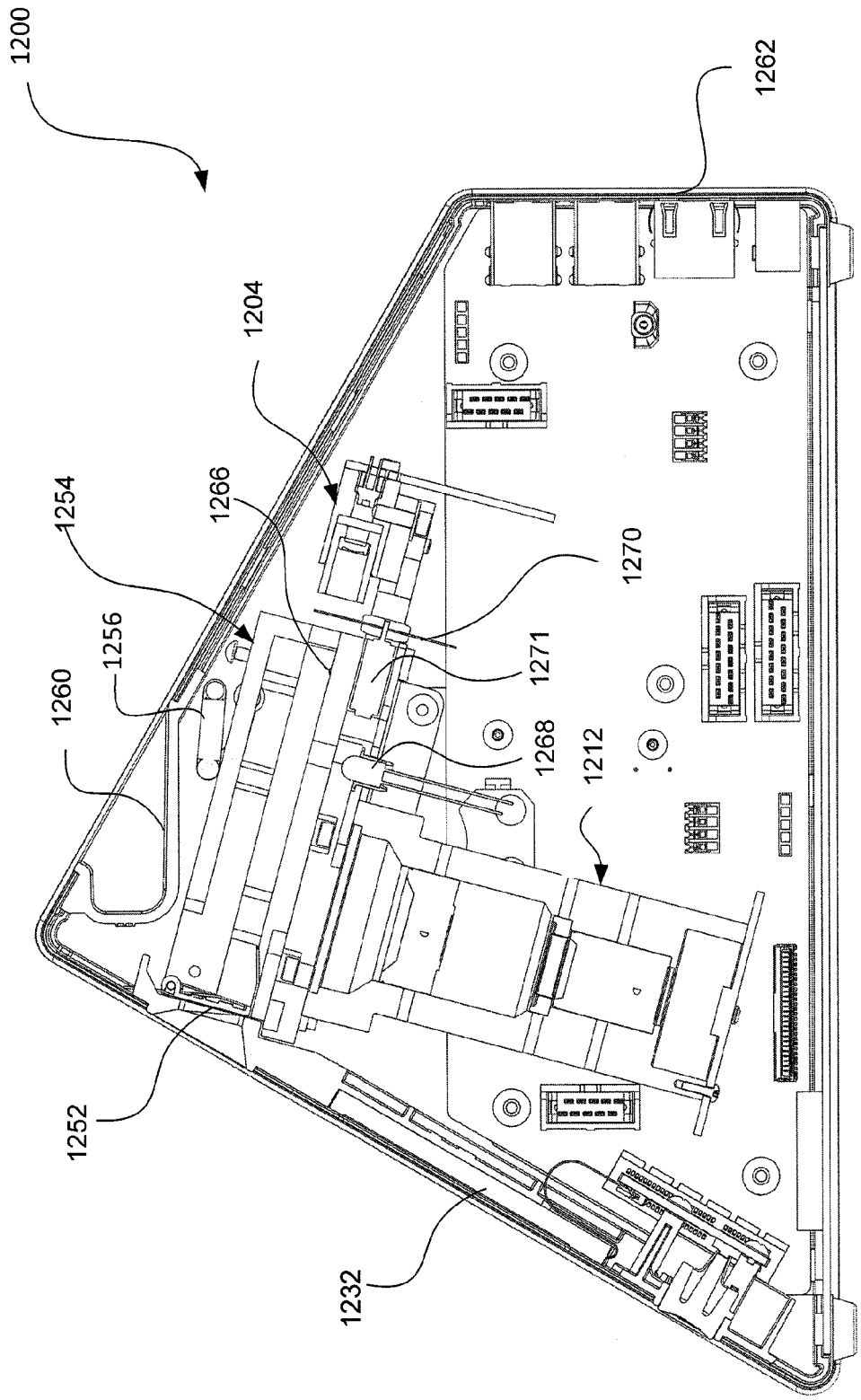
FIG. 14 is a side cross sectional view of an embodiment of a reader instrument to indicate relative positioning of components.
Figure 15:
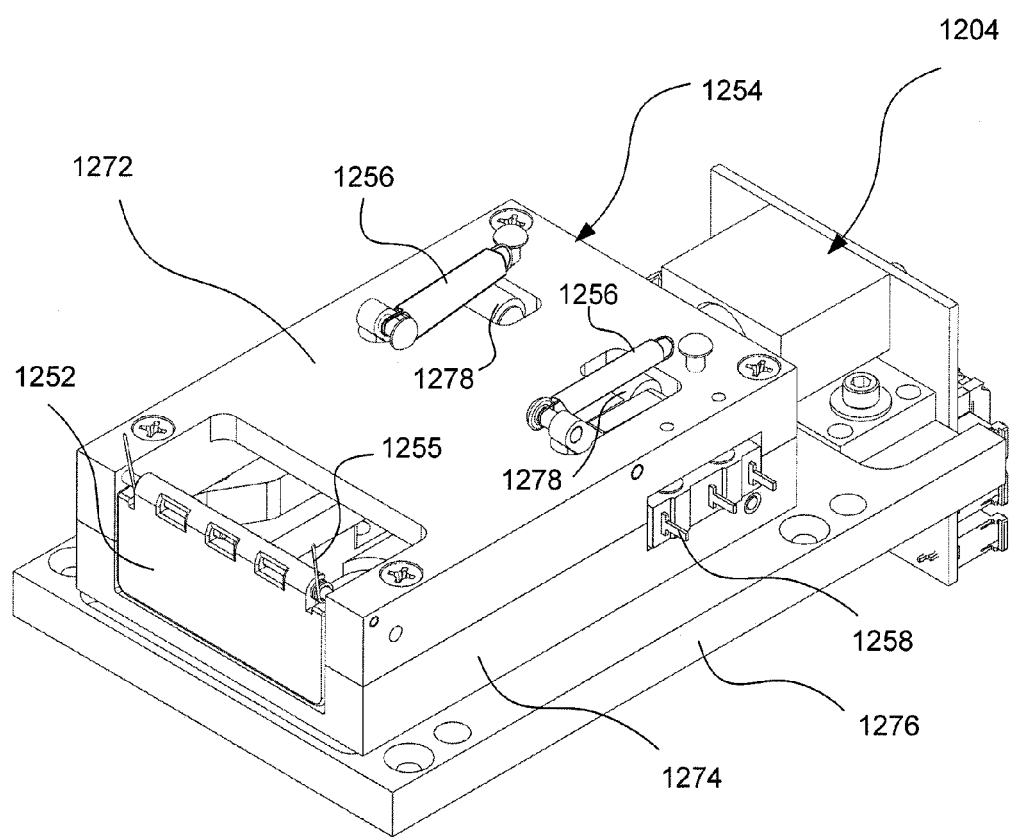
FIG. 15 is perspective view of a cartridge holder assembly, shown in isolation.
Figure 16:
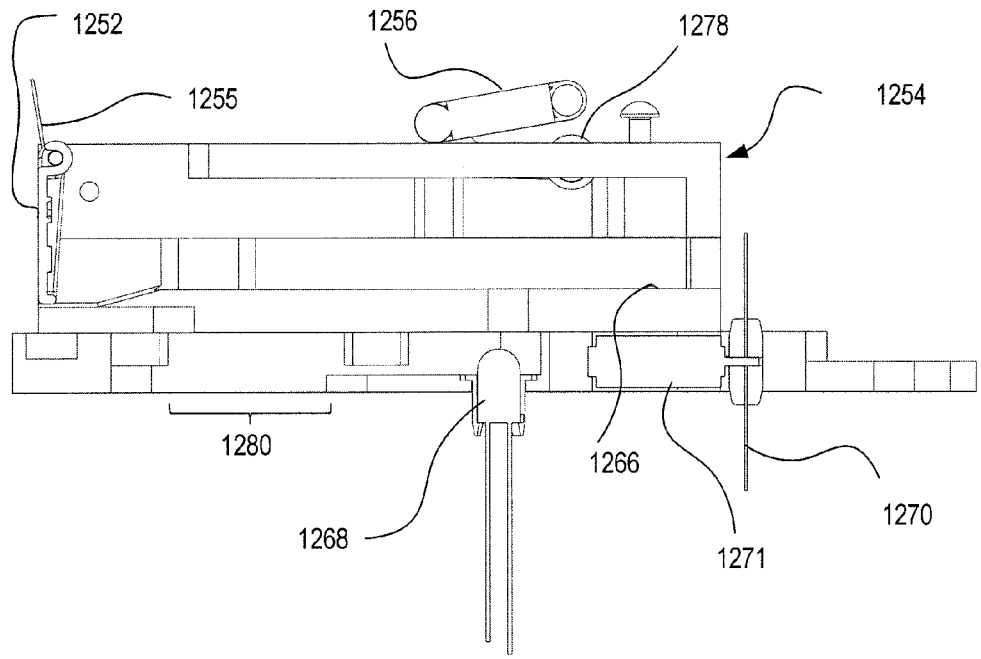
FIG. 16 is a side cross sectional view of the cartridge holder assembly of FIG. 15, with no cartridge inserted.
Figure 17:
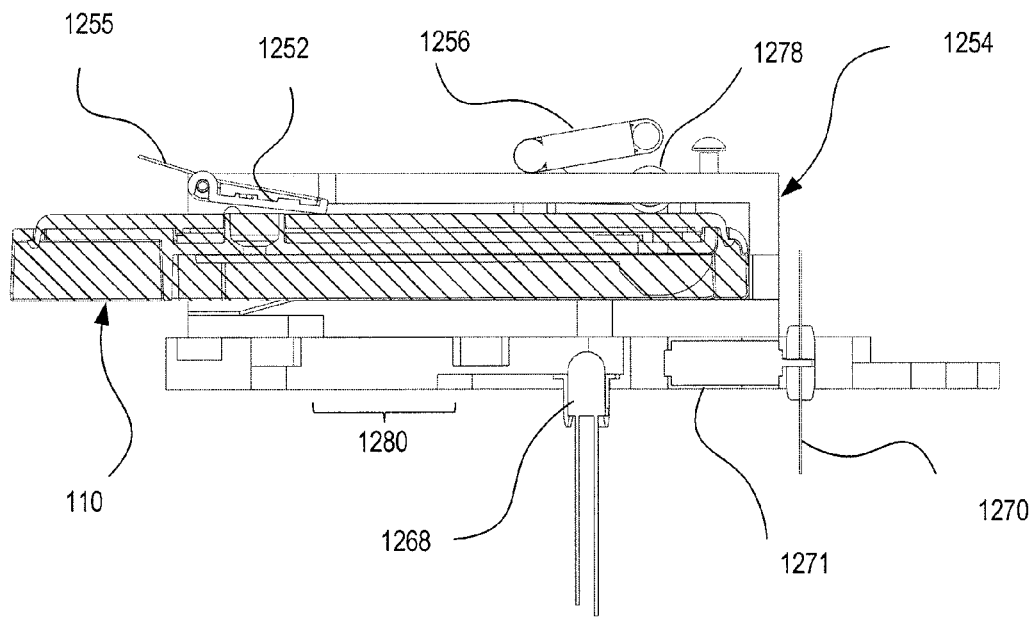
FIG. 17 is a side cross sectional view of the cartridge holder assembly of FIG. 15, with a cartridge inserted therein.

For portable or semi-portable operation, a lightweight, dimensionally small, and space efficient reader instrument is useful. The following paragraphs describe various aspects of one embodiment of such a portable reader instrument. It will be understood that this is a non-limiting example, and smaller or larger stand-alone reader instrument are contemplated, as well as reader instrument integrated as components of a larger sample processing device. A reader instrument 1200 is illustrated in perspective view with its housing partially removed in FIGS. 12 and 13, in cross section in FIG. 14, and with respect to selected components as seen in FIGS. 15 through 17.

Size and Housing

Figure 12:
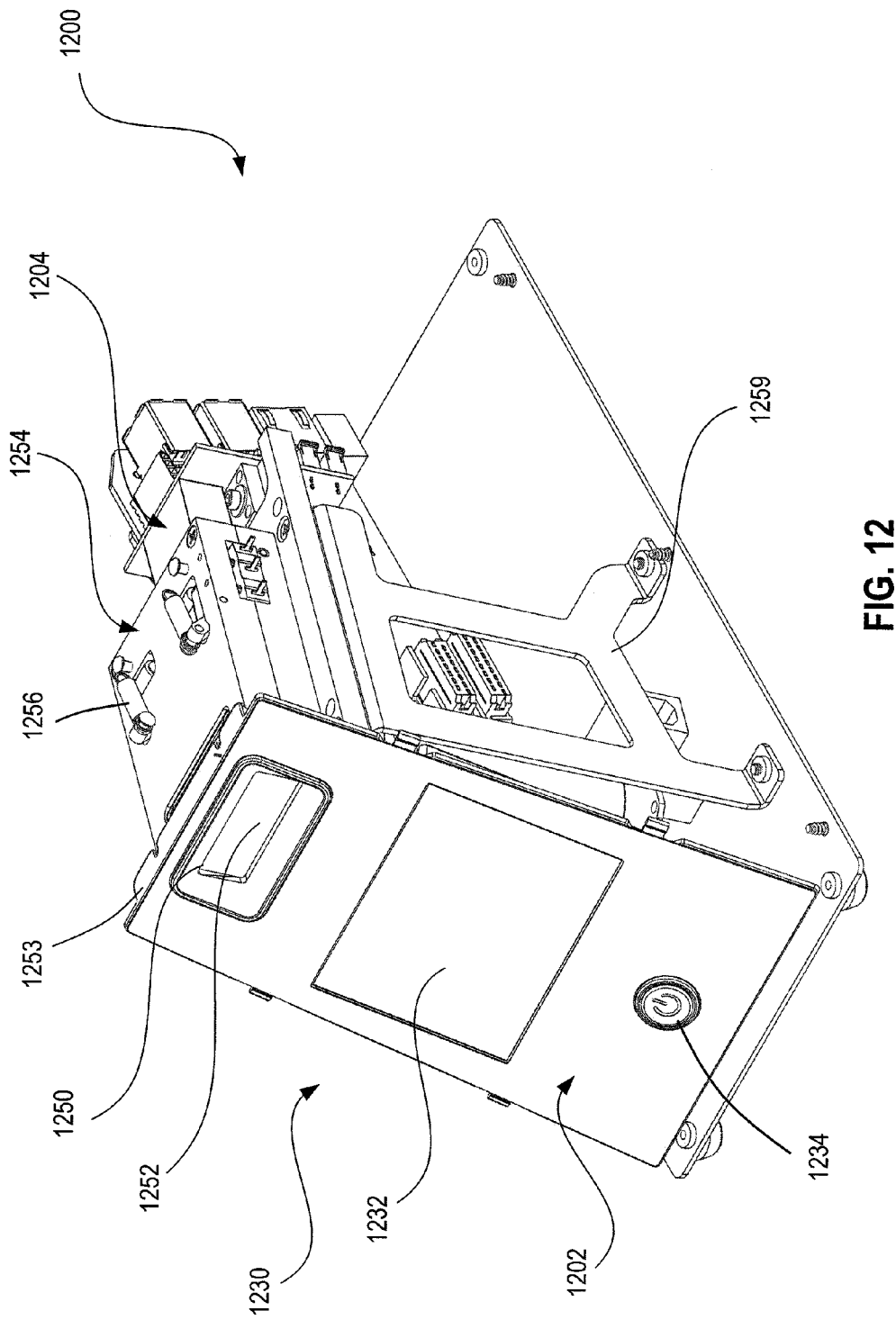
FIG. 12 is a view of an embodiment of a reader instrument of FIG. 1 with the housing partially removed to reveal positioning of components.

One embodiment of such a portable reader instrument is illustrated in FIG. 12 which illustrates a reader instrument 1200 (similar to reader instrument 100 of FIG. 1) with its housing 1202 partially removed for better illustrating layout of internal components. Reader instrument 1200 is suitable for the operational needs and constraints of clinical environments. The reader instrument may weigh less than 10 kg, and it typically weighs only 1 to 3 kg, making it easily transportable. The reader instrument may have volume less than 5000 $cm^3$, and typically has a volume of only 2000 to 3000 $cm^3$. The reader instrument footprint is similarly small, being less than 500 $cm^2$, and typically only 200 to 300 $cm^2$. The reader instrument is small enough to be easily transported and may be stackable on other equipment. To aid in transport, an integral handle 1260 may be formed, as seen in cross section in FIG. 14. The exterior finishing of housing 1202 may be constructed of stainless steel, protectively coated metal, high durability plastics, or other suitable materials capable of withstanding regular cleaning with commercially available solutions, including but not limited to clinical biocides (e.g., Cavicide™), 70% solution isopropyl alcohol, or 20% solution household bleach (i.e., 2% sodium hypochlorite).

User Interface

Continuing to refer to FIG. 12, at least a portion of housing 1202 is angled to allow easy access to a cartridge insertion door and viewing of a user interface 1230. As shown, the user interface may include a flat panel touchscreen display 1232, a power/reset button 1234, and a sound generator (not shown). A user may engage a cartridge (such as cartridge 110 of FIG. 1 or cartridge 300 of FIGS. 3-11) into reader instrument 1200 by inserting it through an aperture 1250 protected by a door 1252. Although door 1252 is shown in FIG. 12 as a spring-loaded flap door, it may alternatively be implemented as a sliding door, a loading tray (manual or automatic), a manual flap door, or any other appropriate mechanism to protect aperture 1250 when reader instrument 1200 is not in use and/or to prevent light leakage while the light sources internal to reader instrument 1200 are in operation. Additionally, while FIGS. 2 and 17 show the cartridge partially protruding from the reader instrument during the operation of the reader instrument, it may be desirable in certain applications for the cartridge to be fully enclosed within the reader instrument while the cartridge is being analyzed therein.

A cartridge holder assembly 1254 physically prevents cartridges from being inserted backwards. Cartridge holder assembly 1254 may include mechanical or electronic components that indicates to the user when a cartridge is fully inserted, such as by audible sound, tactile feedback, display signal, or some combination of above. Cartridge holder assembly 1254 and inserted cartridge are positioned above touchscreen display 1232 in a manner that does not interfere with the operation of touchscreen display 1232 or any other front panel components of user interface 1230.

A user may interact with reader instrument 1200 by using touchscreen display 1232. Touchscreen display 1232 may display analysis results to the user, allow for input of sample and user identifiers to the reader instrument, and allow the user to configure the operation of the reader instrument by choosing options presented on the display. The display may further display status and fault information to the user. The touchscreen may be compatible with a user wearing no gloves (bare fingers), a single layer of gloves, a double layer of gloves, nitrile gloves, or latex gloves, or any other hand protection available to a user.

In certain embodiments, the display size (measured on diagonal) is between 7 and 11 cm. Display resolution may be QVGA (240×320 pixels) in landscape mode or greater. The display may include RGB color with 16-24 bit depth. The display may be backlit with white light emitting diodes ("LEDs"), cold cathode fluorescent tube lighting, or may be internally lit using organic LED displays, or externally lit using electronic ink, micro-electro-mechanical system ("MEMS") interference display or passively lighted display screens. The user may control the power state of the reader instrument by pushing a button 1234 located on front panel. For example, momentarily pressing button 1234 may power the reader instrument to its normal operational state. The reader instrument may wake if in a low power "sleep" state or do nothing if already powered on. Pressing button 1234 for greater than five continuous seconds may cause the reader instrument to safely power off. Button may be located such that it does not interfere with operation of the touchscreen display or any other front panel components.

To increase throughput, in an exemplary embodiment, the reader instrument may be configured to produce analysis results after approximately 30 seconds from cartridge insertion to delivery of analysis results to user. These results may be displayed in whole or in part on touchscreen display 1232. Additionally, the reader instrument may store in internal memory storage two thousand or more analysis results. Such analysis results may include, for example, patient or sample identifier, cartridge lot number, date and time of test, date and time of a linked quality control operation, signal-to-cutoff ratio for all biomarkers, and analysis result (e.g., positive/negative/indeterminate for the presence of antibodies in the sample, and a quantitative output) for all tested analytes. Finally, the user may have the option to store and download measurement results that include full image sequences of the cartridge microarray and any associated cartridge identification information.

Since a user may wish to use other input devices or support remote usage of the reader instrument, communication with external peripheral devices may be enabled. The reader instrument may have, for example, a USB Type A port that supports an optional barcode reader (compatible with one or both of standard 1-D and 2-D codes) for inputting sample identifiers or user codes. A USB Type A connectors may be located on a rear panel 1262 (FIG. 14) to support computer-to-computer communication as a slave device. The reader instrument may also allow networked communication with other computer systems connected by Ethernet, and accordingly includes one RJ45 Ethernet connector located on rear panel.

Cartridge Holder Assembly

Precise positioning and reliable engagement of a cartridge with reader instrument 1200 may be required for proper operation of the reader instrument. Positioning of cartridge holder assembly 1254 with respect to housing 1202 is illustrated in FIGS. 15 through 17. While FIG. 12 shows the cartridge holder assembly with respect to the housing, an isolated cartridge holder assembly 1254 is indicated in perspective view in FIG. 15, and side cross sectional views with cartridge absent and fully inserted are respectively seen in FIGS. 16 and 17.

Cartridge holder assembly 1254 may be attached, at least in part, to housing 1202 by a front bracket 1253 and a side bracket 1259. Cartridge holder assembly 1254 may include a door 1252, which may be spring-loaded with a spring 1255 to block aperture 1250 in a normally closed position, protecting users from inadvertent exposure to laser light potentially emanating from reader instrument 1200, and limiting admission of dust, dirt or other contaminants into reader instrument 1200.

Elements that assist in proper positioning of a cartridge are illustrated in FIGS. 15, and 16-17. A cartridge may be mechanically held in proper position by cooperation of door 1252, spring-loaded levers 1256, and rollers 1278. Spring pressure from spring-loaded levers 1256 and rollers 1278 holds a cartridge in position against laser illumination module 1204. In the exemplary embodiment shown in FIG. 15, cartridge holder assembly 1254 is formed of a lever plate 1272, onto which door 1252, spring-loaded levers 1256 and rollers 1278 are mounted, a guide plate 1274, which includes features for guiding an inserted cartridge into proper position, and a base plate 1276, onto which laser illumination module 1204 and guide plate 1274 are fastened. Guide plate 1274 and base plate 1276 are configured with openings therein so as to collectively define an aperture 1280 through which the inserted cartridge may be viewed and imaged.

The correct positioning of the cartridge within the reader instrument activates a safety interlock switch 1258, which allows activation of the laser in laser illumination module 1204. In other words, safety interlock switch 1258 (FIGS. 13 and 15) monitors when a cartridge is properly inserted into reader instrument 1200, thereby enabling laser illumination to occur. Proper positioning of the cartridge may be indicated to the user by, for example, an audible and/or tangible "click" produced by a pin 1266 (FIGS. 14 and 16), which is configured to produce the "click" when compressed by a cartridge placed thereon. When the cartridge is extracted, switch 1258 physically disables the laser illumination circuitry, preventing possible accidental laser radiation exposure to the operator. Upon removal of the cartridge, door 1252 rotates back to a closed position.

Laser Illumination Module and Light Transmission Module

Precise and accurate illumination control is an important element of reader instrument 1200 operation. In one embodiment illustrated in part with respect to FIGS. 12 through 14, laser illumination module 1204 produces illumination light capable of optically coupling to waveguide of cartridge after passing through the light transmission module, which is cooperatively composed of housing-mounted optical elements and cartridge-mounted integral lens elements.

Laser illumination module 1204 may provide light with suitable optical power, for example, between 10 and 100 milliwatts. To maintain calibration and desired reader instrument sensitivity, it may be advantageous for the optical power to have long-term stability better than 15% drift per month, along with a short-term stability better than 1% RMS variation at a 5-second integration time. In some embodiments, laser light may have wavelength equal to 660±5 nm. This wavelength specification may be changed (e.g., to 642 nm±5 nm) to accommodate different fluorescent tag systems, and in some advanced reader instrument embodiments multiple or tunable laser light wavelengths may be used.

In an embodiment, the laser light may be polarized orthogonal to plane of cartridge waveguide, to better than 10% polarization extinction ratio. The laser light may be directed toward the cartridge so that it propagates in a direction inside the waveguide that is within 1°, such as between 0.10° and 0.25° of being parallel to the long axis (centerline) in the plane of the assay surface of the waveguide. The laser light ordinarily propagates along the centerline of the waveguide. Ideally, the relative average power difference between waveguide surface locations that are equidistant from the centerline is less than 10%, such as between about 1% and 5%. When a cartridge is fully inserted into the reader instrument, laser light may enter the coupling lens of the cartridge waveguide at a height and angle relative to top surface of waveguide that optimizes assay performance. The laser light is collimated (e.g., to less than 2 to 5 degrees far-field divergence angle) so as to ensure uniformity of illumination throughout the length of the waveguide, particularly in the assay region. Additionally, collimation of the laser light may further reduce sensitivity of the reader instrument to longitudinal displacement (i.e., in a direction indicated by double-headed arrow 108 in FIG. 2) of the waveguide with respect to laser illumination module 1204. Beam width ($1/e^2$ full width) is parallel to polarization axis and selected to be about 1.7±0.2 mm (affects longitudinal uniformity). Beam width ($1/e^2$ full width) perpendicular to polarization axis may be, for example, 9±1 mm (this parameter affects transverse uniformity). In operation, far-field spatial deviations in the imaging region negligibly contribute to site-to-site variations of the assay. RMS variations of the optical power at the surface of the waveguide, with an averaging window of 60 μm, may be less than 10%. Finally, RMS variations of the optical power at the surface of the waveguide, with an averaging window of 600 μm, may be less than 10% (typically between 1% and 5%).

Additional light sources may be used to illuminate portions of the cartridge when inserted into the reader instrument. For instance, an LED 1268 may be used to illuminate features, such as a barcode or a fiducial mark, disposed on a bottom portion of the cartridge.

In an embodiment, a rotating diffuser system may be used to further improve the uniformity of the laser light illumination. For example, a diffuser (such as rotating diffuser 1270 of FIGS. 16 and 17) may be used with rotation, in which the diffuser itself is rotated about an axis parallel to, but offset from the laser beam propagation direction. In this way, the need for any wedge and/or focusing lenses for the laser beam around the location of diffuser 1270 is eliminated, hence greatly simplifying the optical path compared to existing art (see, for example, Hard et al., "Phase-randomized laser illumination for microscopy," J. Cell Sci. 23:335-343, 1977).

It is recognized that the method, as disclosed herein, removes undesirable non-uniformities in the planar waveguide illumination, and thus in the fluorescence images of microarrays (including one or more reaction sites) illuminated by the laser beam inserted into the planar waveguide, thereby resulting in several positive benefits: 1) improved image quality; 2) reduced intra-site coefficient of variation ("CV"); and 3) reduced inter-site CV. The improved image quality is due to the fact that, without speckle, the fluorescence images give a very clear picture of the morphology of the reaction sites. The intra-site intensity variation may be significantly reduced and better reflect the actual reaction site morphology, thus eliminating the need for averaging over a large spatial area in order to obtain a reliable average reaction site signal intensity. Accordingly, it may be possible to reduce the size of the reaction site and pack more features into the microarray without suffering from speckle-induced degradation in the data quality. Furthermore, in the presence of speckle effects in the captured image, the spatial averaging in a fluorescence imaged affected by speckle is not ideal, even with a reaction site spot diameter of ~0.6 mm. In an array with replicate features within a row, the speckle therefore contributes to the inter-site CV. Rotating diffuser 1270 may substantially eliminate the speckle-induced contribution resulting in an improved inter-site CV.

Referring again to FIGS. 15-17, diffuser 1270 is placed in the excitation beam in the abovementioned target imaging system. Diffuser 1270 may be rotated, for example, using a motor 1271. In an example, the diffuser has random structure which imposes structure on the laser beam by means of diffraction. The diffuser does not significantly degrade the coherence of the laser beam. However, if the laser beam is passed through rotating diffuser 1270 (rotating in the plane of the diffuser about an axis offset from the beam axis), any speckle effect is virtually eliminated from the laser beam profile when time-averaged over a sufficiently long time period. Consequently, when the microarray imaging exposure time is much greater than the diffuser structure sampling time, all signs of speckle in the excitation light disappear. This provides uniform excitation of the microarray, which in turn yields speckle-free fluorescence images.

Figure 18:
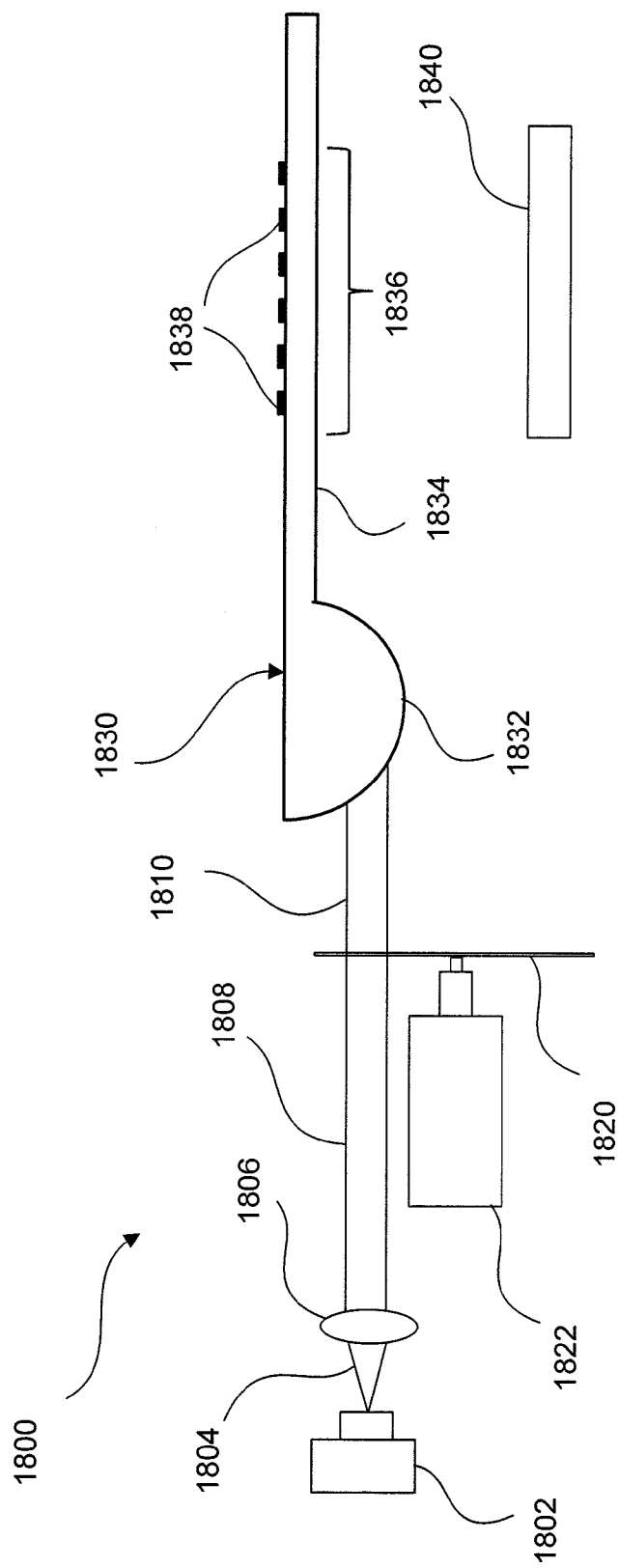
FIG. 18 shows a schematic diagram of a target imaging system, in accordance with an embodiment. The output of a laser diode is collimated, passed through a rotating holographic diffuser, then coupled into a planar waveguide.

Referring particularly to FIG. 18, a diagrammatic illustration of an exemplary waveguide-based sample imaging system 1800 is shown, in accordance with an embodiment. A laser diode 1802 emits a diverging beam 1804, which is passed through a collimating lens 1806 so as to be transformed into a collimated beam 1808. Collimated beam 1808 passes through a diffuser 1820, which is rotated about an axis parallel to the propagation direction of collimated beam 1808, so as to generate a uniform beam 1810. Uniform beam 1810 is directed toward a waveguide arrangement 1830. Waveguide arrangement 1830 includes an integrated lens 1832, a planar portion 1834 and an assay region 1836, which includes a plurality of reaction sites 1838. Reaction sites may include immobilized biomolecules such as antigens, antibodies, proteins, peptides, glycans, or nucleic acids. Various methods of preparing printed microarrays, including contact printing, inkjet printing, piezoelectric printing, and solenoid valve jet printing are available.

Continuing to refer to FIG. 18, uniform beam 1810 is coupled into waveguide arrangement 1830 via integrated lens 1832 such that uniform beam 1810 is guided through planar portion 1834 by total internal reflection. Consequently, the evanescent wave portion of uniform beam 1810, so guided through planar portion 1834, illuminates assay region 1836. Any resulting signal, such as fluorescence, is captured at a sensor 1840. This method may be applicable for both a waveguide with an integrated coupling lens (as shown in FIG. 18) and a waveguide with coupling optics that is separate from the planar portion of the waveguide arrangement.

The location of the rotating diffuser in the path of collimated beam 1808 is advantageous because rotating diffuser 1820 may be selected to impart only a small amount of divergence to collimated beam 1808 while generally preserving the coherence of collimated beam 1808. In other words, the diffuser may be disposed as close to planar portion 1834 such that any small, potentially unavoidable divergence of collimated beam 1808 created by diffuser 1820 has minimal effect over the extent of waveguide arrangement 1830. Also, for combinations of a small laser diode and an inexpensive collimating lens, space constraints may preclude the possibility of inserting a diffuser in the path of diverging beam 1804.

Imaging System

Referring again to FIGS. 12-14, an imaging sensor (such as a two dimensional CMOS or CCD sensor) may be used in reader instrument 1200. In one embodiment illustrated in part with respect to FIGS. 12 through 14, sensor 1212 may be mounted in reader instrument 1200. Imaging optics may be positioned over the imaging sensor. Use of imaging optics fixed with respect to the imaging sensor may lower reader instrument cost, eliminate a requirement for potentially expensive autofocus circuitry, and increase tolerance of the sensor to shock.

The sensor may be, for example, MT9M001 from Micron (Aptina), which is a ½", 1.3 Mpixel, monochrome sensor with 1280×1024 pixels (Pixel size: 5.2 μm×5.2 μm). The objective system may be, for example, V13VM615 from Xiamen Leading Optics, which is a closed-circuit television ("CCTV") lens with variable focus/zoom/iris with f/1.4 and focal length of 6-15 mm. The objective system may be used as is or, alternatively, separated into components and mounted into a custom-made barrel. Due to the fact that the imaging system creates a demagnified image in performing the analyte detection, the depth of field of the aligned system is approximately 2 mm. The object to image distance may be, for example, less than 100 mm. A fluorescence emission filter may be placed within the imaging system, in an embodiment. The fluorescence emission filter serves to block light having approximately the same wavelength as the laser light illuminating the planar waveguide, while transmitting fluorescence signal from the assay region. For example, the fluorescence emission filter may be positioned between the objective system and the cartridge, or between separated components within the objective system. The resulting magnification provided by the imaging system is approximately ⅐. The resulting pixel size in object space is approximately 35 μm×35 μm. The light signal is prevented from reaching a vertical belt (short dimension) along one side of the sensor such that this part of the sensor then gives a measurement of the dark noise (i.e., readout noise). Furthermore, a series of exposure times are used in the imaging process in order to extend the dynamic range to almost 4 orders of magnitude, as enabled by the dark noise subtraction.

Example 2

Automatic Cartridge Identification with Peripherals

Accurate cartridge identification and tracking is useful for commercial reader instruments. Peripheral tracking modules based on one or two dimensional bar codes, RFID readers, or other conventional tracking technologies are contemplated. As may be seen in FIG. 19, for example, a peripheral device 1980. Peripheral device 1980 may be, for example, a USB-attached computer, printer, keyboard, mouse, barcode reader, or other device to aid with information input or output from the reader instrument. As desired, peripheral device 1980 may be configured to read bar codes, color codings, alphanumeric labeling, RFID tags, or any other suitable cartridge identification mechanism. In other embodiments, internally mounted barcode, RFID, or other readers are contemplated.

Example 3

Automatic Cartridge Identification with Internal Imaging System

As previously noted, accurate cartridge identification and tracking may be useful in certain applications. In one embodiment, the image sensor may also be used to identify the cartridge. This specification further minimizes the opportunity for human error, and eliminates the need for auxiliary bar code, RFID, or other expensive attached or separately mounted cartridge identification mechanisms. In an embodiment, instead of having a user scan a cartridge's optical encoding using a peripheral device, as discussed with respect to FIG. 19, the reader instrument may automatically scan the optical encoding after insertion of the cartridge into the analysis slot. This process is schematically illustrated in FIG. 20, which shows a cartridge 2020 containing information indicators 2023 adjacent to reaction sites 2021, which are imaged by an imaging system 2012 having a field of view 2070. Information indicators 2023 may be, for example, printed two-dimensional bar codes. Various other features of cartridge 2020, such as an enclosure (e.g., cartridge 300 of FIG. 3), are omitted from FIG. 20 for illustrative clarity. The reaction sites may be printed on the cartridge in the same field of view 2070 of imaging system 2012 as information indicators 2023. To maximize the amount of printable information, field of view 2070 of imaging system 2012 may include edges of the cartridge and bar code printable portions of the cartridge surrounding reaction sites 2021. In certain other embodiments, bar code or other information may be separately printed and attached to a cartridge.

Figure 21:
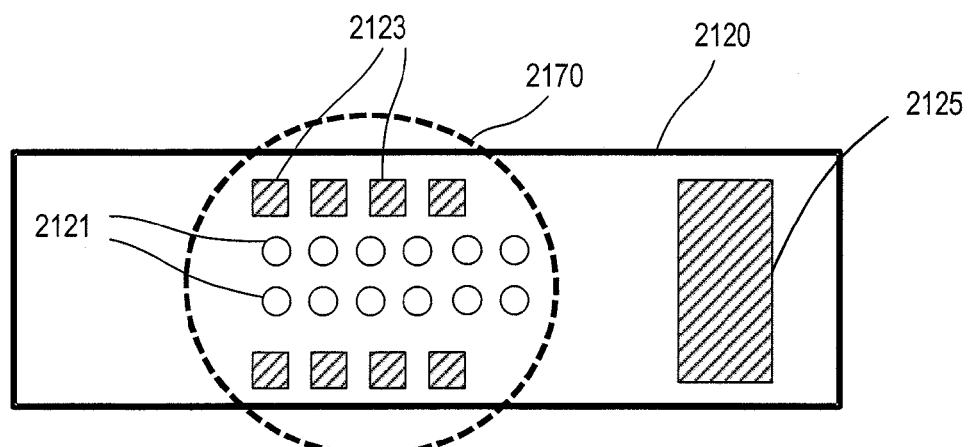
FIG. 21 is schematic top down view of the field of view of an imaging system, including various markings and analyte markers, in accordance with an embodiment.

An exemplary layout of features on a cartridge is shown in FIG. 21. A cartridge 2120 (again, with various features omitted for illustrative clarity), includes a plurality of reaction sites 2121 with small information indicators 2123 and a large information indicator 2125. Reaction sites 2121 and small information indicators 2123 are shown to be within a field of view 2170 of an imaging system (not shown), while large information indicator 2125 is outside of field of view 2170. Consequently, small information indicators 2123 may be imaged and decoded by the same sensor within the imaging system that is used to perform the analyte detection, while large information indicator 2125 may be read separately by another sensor, a peripheral device, or by a user. Small and large information indicators 2123 and 2125, respectively, may be printed bar codes. Large information indicator 2125 may be, for instance, a note handwritten by a user or an ID code or sticker.

In an embodiment, a prepared cartridge with identifying information may be inserted into the reader instrument for analysis. Before analysis occurs, the imaging system images optical encoding (bar code, coded dot patterns, OCR evaluated text, or other suitable information symbols) located on the underside of the cartridge. The read data is stored in a log file, and may optionally be automatically associated with additional calibration or tracking material, internally stored in the reader instrument or available by wired, wireless, or internet connection. The reader instrument proceeds to automatically analyze the sample and stores those results as well. After test completion, the reader instrument indicates to the user the test is complete and the cartridge is automatically ejected or ready to be manually removed. Advantageously, using this procedure and apparatus the pertinent information optically encoded in the cartridge is accurately read and stored every time a cartridge is analyzed without the need for an extra internal scanner or extra manual steps. Optionally, an LED (such as LED 1268 of FIGS. 14, 16 and 17) or some other type of light source that is internal to the reader instrument may be used to illuminate the barcode during imaging.

Example 4

Automatic Reaction Site Identification and Layout Recognition

Figure 22:
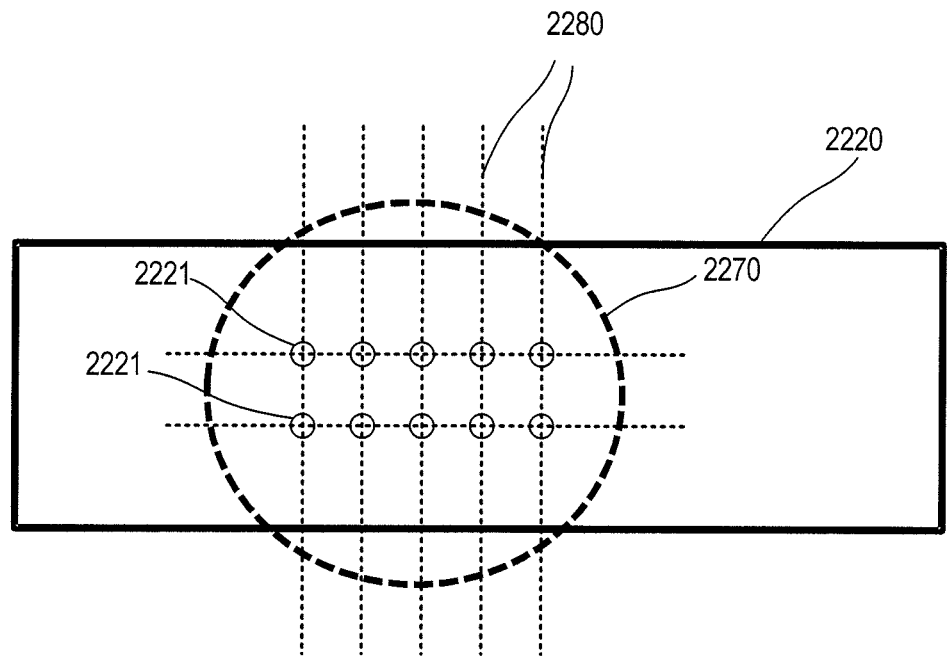
FIGS. 22 and 23 respectively illustrate rectangular grid and staggered patterns for reaction site layout, in accordance with an embodiment.
Figure 23:
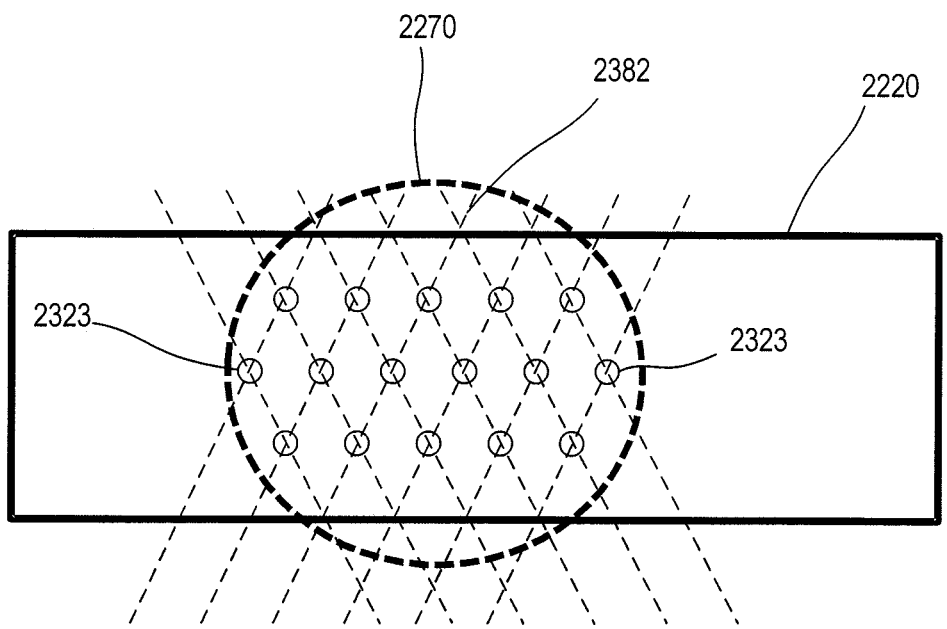

FIGS. 22 and 23 illustrate site layout patterns for analyte detecting molecules immobilized onto a waveguide 2220.

Reaction sites may be printed onto a waveguide 2220. For example, as shown in FIG. 22, reaction sites 2221 may be printed in a rectangular layout. Alternatively, as shown in FIG. 23, reaction sites 2323 may be printed in a staggered, diagonal layout. Other geometric layout configurations may be contemplated. In any layout, the reaction sites are located within a field of view 2270 of the imaging system within the reader instrument (not shown). When locating the reaction sites in a captured image, the reader instrument may use firmware-contained, cartridge-defined, or internet-downloaded information to correlate reaction site position and recognition. In certain embodiments, reader instrument algorithms may be programmed to identify a specific grid layout as one step toward determining reaction site identity. For example, a grid pattern 2280, as indicated by dashed lines in FIG. 22, or a slanted grid pattern 2382, as indicated in FIG. 23, may be used as a basis of a circle-finding algorithm to locate and analyze the plurality of reaction sites on waveguide 2220. Reader instrument identification of grid patterns, such as grid patterns 2280 and 2382, in accordance with print layout information extracted from the reading of the identification indicia, allows for compatibility with variety of reaction site patterns in the analyte detection process. In addition, in the event that grid layout or image view is skewed (e.g., due to rotation of cartridge or reaction site printing misalignment), the algorithm so implemented may compensate for the skewed image by determining the actual grid pattern and making a "best fit" match to identify the reaction sites.

Example 5

Reaction Site Pattern and Size Variations

Figure 24:
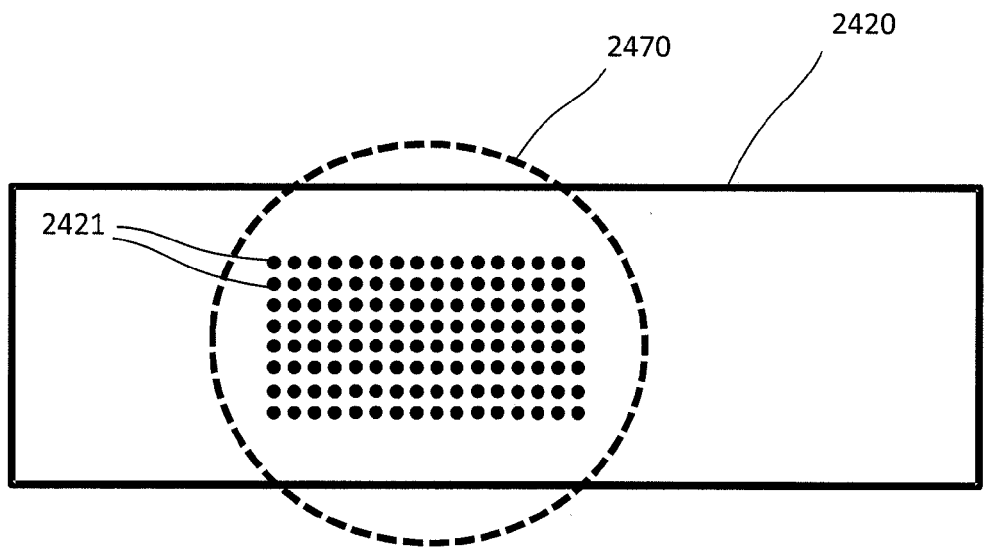
FIGS. 24 and 25 respectively illustrate reaction sites with different sizes, in accordance with an embodiment.
Figure 25:
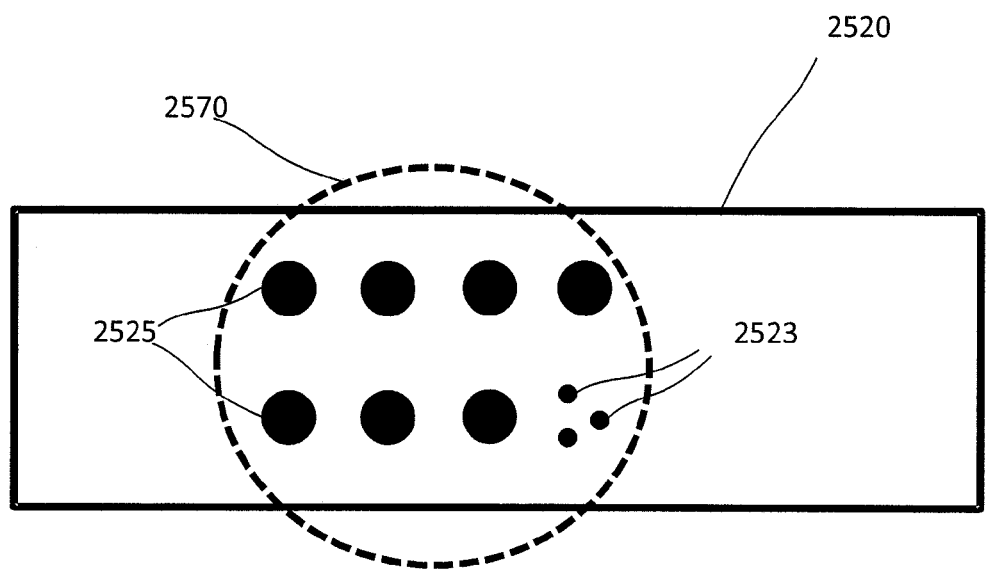

FIGS. 24 and 25 illustrate alternative reaction site layout patterns for reaction sites immobilized onto a waveguide. FIG. 24 shows a large number of small reaction sites 2421 densely printed on a waveguide 2420 and within a field of view 2470 of an imaging system (not shown). FIG. 25 shows a plurality of small and large reaction sites 2523 and 2525, respectively, printed on waveguide 2520 and within field of view 2570. In certain embodiments, fifty or more reaction sites can be simultaneously imaged in a single field of view, with even more possible if bar code or other identifying indicia are not required to be located in the same field of view as shown in FIGS. 20 and 21.

Example 6

Plasma Treatment of Surfaces in the Cartridge

One useful technique for certain applications involves plasma treatment to clean a surface by ion bombardment and physical ablation of contaminants, particularly for elimination of organic contaminants. In addition, plasma treatment can be used to modify surfaces for attachment or adsorption of functional groups, such as for the printing of reaction sites. Furthermore, plasma treatment of a surface may modify the flow behavior of fluids coming into contact with that surface.

In one embodiment, a waveguide may be prepared for attachment of desired reaction sites by use of an argon/oxygen plasma cleaning. Following cleaning, epoxy-silane may be deposited n the cleaned surface of the waveguide to functionalize and prepare the waveguide for further processing.

Additionally, capillary flow within the cartridge may be enhanced by suitable coatings or treatments of both the flow plate and the waveguide. In one embodiment, both the flow plate and the waveguide are subjected to a plasma cleaning step. When assembled, capillary flow rate is greatly enhanced relative to cartridges having a flow plate that has not been subjected to a plasma treatment. Consequently, smaller volumes of sample (e.g., 50 microliters or less) may be needed to perform the analyte detection process.

Example 7

Disposable Assay Cartridge and Assay System

Figure 26:
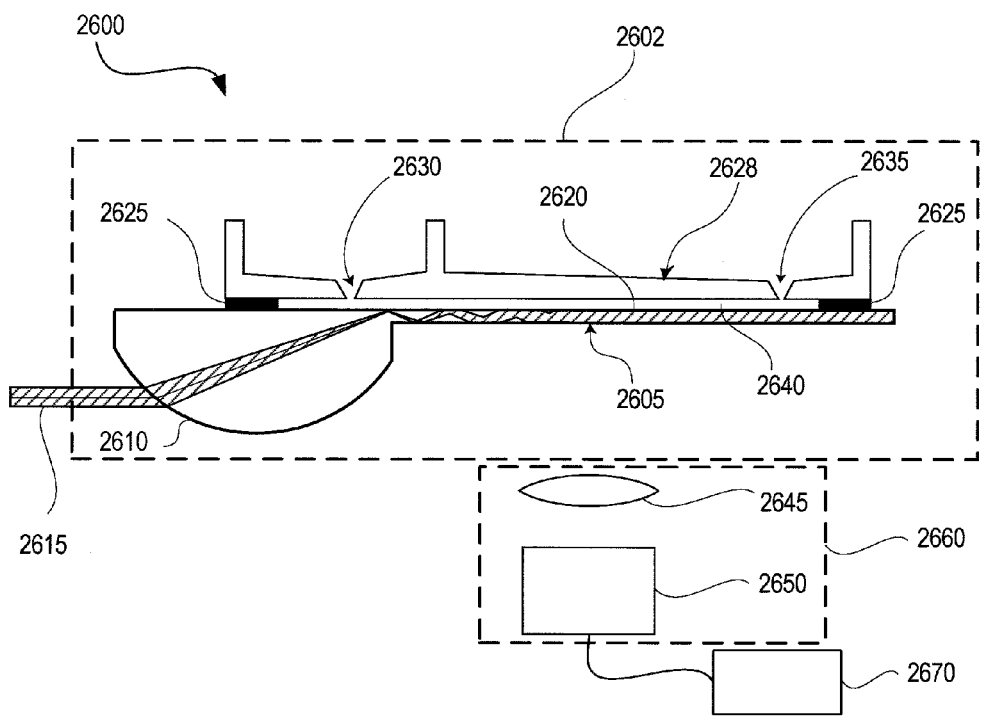
FIG. 26 illustrates a diagrammatic illustration of an assay system including the device having a waveguide with an integrated lens, illumination, and imaging system, in accordance with an embodiment.

FIG. 26 shows a schematic representation of an exemplary disposable assay cartridge and a multiplexed fluorescence assay, in accordance with an embodiment. A protein microarray is printed to a plastic planar waveguide which is bonded to a plastic upper component to define a flow channel. Fluids, such as sample, wash, and detect reagents may be introduced via an inlet port. The assay surface may be illuminated by an evanescent field generated down the length of the multi-mode waveguide. The array is imaged in a single field of view through the plane of the waveguide.

At the TIR interface, an evanescent field is generated that decays exponentially into the aqueous medium. The decay length of the evanescent field is on the order of a hundred nanometers for visible light. For fluorescence assay applications, the advantage is localization of the illumination source precisely at the solid-liquid assay interface, limiting negative effects such as the bulk solution, line-of-sight, light scattering.

Figure 27:
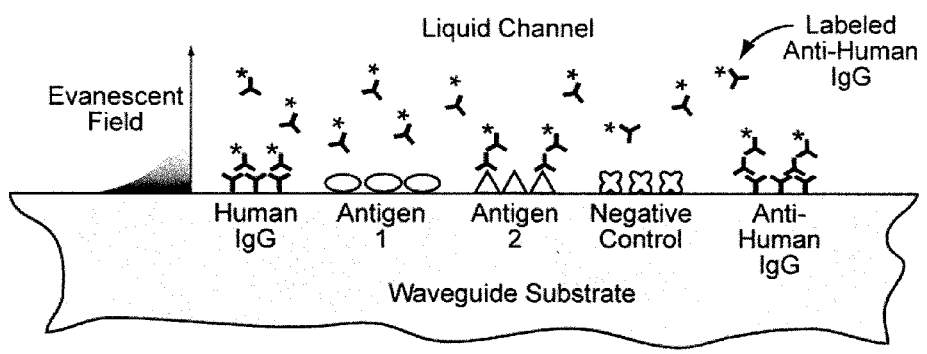
FIG. 27 is a schematic representation of the multiplexed fluorescence assay and assay cartridge, in accordance with an embodiment.

The cartridge is based on a thick (~1 mm), multi-mode planar waveguide fabricated by injection molding of a low auto-fluorescence plastic (e.g., cyclic olefin polymer). One of the major advantages of this cartridge configuration is the incorporation of a coupling lens into the molded waveguide (FIG. 27). This lens design overcomes fundamental challenge of reproducible light coupling to the waveguide in prior designs. The lens design creates a diverging beam such that modes mix down the length of the waveguide, eventually creating a spatially uniform illumination field along the axial length of the waveguide.

The plastic waveguides are activated with a surface chemistry treatment to render them amine-reactive. Details of the surface activation are similar to methods described in the literature, with proprietary modifications and improvements.

A protein array is printed to the activated surface of the planar waveguide prior to assembly into the cartridge. Details of the array features and layout are provided below. The arrays may be printed with a commercial arrayer, such as Bio-Dot AD3200 robotic arrayer equipped with Bio-Jet print head dispensing 28 nanoliter droplets. Resulting reaction site diameters are approximately 0.5 mm, and the arrays are printed on a grid with 1.25 mm centers. The length of the 30 feature (i.e., 2 rows by 15 columns in the present example) array is approximately 17.5 mm. After printing, the waveguide arrays are rinsed with a protein-based blocking agent, spin-dried, and then coated with a sugar-based stabilizer for storage.

Printed waveguides are assembled into an injection molded cartridge to form a 2 to 5 mm-wide fluidic channel with a volume of approximately 30 microliters. The cartridge inlet port provides a reservoir for introduction of assay fluids. The exit port provides a fluidic contact to an absorbent pad that serves as a waste reservoir. The cartridge is configured to provide reproducible passive fluid flow, driven by a combination of capillary action and hydrostatic pressure, as described in, for instance, U.S. Provisional Patent Application Ser. No. 61/391,911 entitled "Fluidic Assay Cartridge with Controlled Passive Flow" filed 11 Oct. 2010. All fluids stay on board the cartridge upon completion of the assay procedure, thus minimizing biohazard. In this way, a combination of printed antigens, controls, and a sample placed in the liquid channel may be used to perform an assay, as schematically shown in FIG. 27.

Returning to FIG. 26, further details of the cartridge and assay system are described. FIG. 26 illustrates a cross-sectional view of an assay system 2600, including a cartridge 2602. Cartridge 2602 includes a planar waveguide 2605 with an integrated lens 2610 suitable for use with the labeled antigen assay of FIG. 27, in accordance with the embodiment (See also U.S. patent application Ser. No. 12/617,535, which is incorporated herein in its entirety by reference). An illumination beam 2615 is inserted into planar waveguide 2605 through integrated lens 2610. Illumination beam 2615 may be provided, for example, by a laser with an appropriate wavelength to excite fluorescent labels at an assay surface 2620. Other appropriate forms of illumination, either collimated or uncollimated, may also be used with assay system 2600. Integrated lens 2610 is configured to cooperate with planar waveguide 2605 such that illumination beam 2615, so inserted, is guided through planar waveguide 2605 and may illuminate assay surface 2620 by evanescent light coupling. Assay surface 2620, an upper component 2628, which includes an inlet port 2630 and an output port 2635, cooperate to define a fluidic sample chamber 2640. Assay surface 2620 and upper element 2628 can be bonded via a channel-defining adhesive gasket 2625 or via direct bonding methods such as laser welding, ultrasonic welding, or solvent bonding. Appropriate chemical compounds (such as a printed antigen) are bound to assay surface 2620 such that when a biological sample and labeled detect reagent are added to the fluidic sample chamber 2640, a target analyte, if present, forms a sandwich between its specific labeled detect reagent and its specific chemical compound immobilized on assay surface 2620. If the specific complex is formed at assay surface 2620, fluorescence signal at the immobilized compound location is indicative of the presence of the target analyte within the biological sample. As an example, collection and filtering optics 2645 may be used to capture the fluorescence signal from assay surface 2620. A signal corresponding to the fluorescence so captured may then be directed to an imaging device 2650, such as a CCD or CMOS sensor.

In a further embodiment, assay system 2600 may be used for rapid, simple detection of multiple target antibodies in a single biological sample. Multiple different antigens may be immobilized at reaction sites on the assay surface, such as in stripes or spots in an array format using printing technology, thereby creating a spatially-localized set of parallel assay locations. The combination of a biological sample, labeled antibody against human IgG, and immobilized antigens on assay surface 2620 may lead to the formation of multiple physically separated antigen-antibody complexes on the assay surface. Illumination of assay surface 2620 results in spatially-localized fluorescence signal that may be read with a detection system 2660 including collection and filtering optics 2645, imaging device 2650, and computer 2670. Computer 2670 may be integrated into the detection system instrument (e.g., single board computer). Alternatively, computer 2670 could be an external device, such as peripheral device 1930 of FIG. 19.

Example 8

Multiplexed HIV/Syphilis/HCV Panel Assay

Unless otherwise specified in this disclosure, components, reagents, protocol, and other methods used in the system and the assays are as described in the Materials and Methods Section of the Example, and are for the purpose of illustration only.

This example demonstrates an HIV-1 Ab assay with 100% agreement with known seroreactivity on a collection of 82 HIV Ab-positive and 142 HIV Ab-negative samples, including multiple samples with HCV and syphilis co-infection. It also demonstrates a treponemal-specific syphilis antibody assay that correctly identifies 67 of 68 *T. pallidum* Ab positive and 100 of 102 *T. pallidum* Ab negative samples. The HCV assay correctly identifies 59 of 60 HCV Ab-positive and 120 of 121 HCV Ab-negative samples. Multiplexed assay performance on whole blood samples is also demonstrated.

Materials and Methods

Biological Reagents.

Modern serological assays for infectious diseases are typically based on recombinant proteins, multiple-epitope fusion proteins, and antigenic peptides. Selection, screening, and optimization of immobilized antigens are an important aspect of assay development. For the purposes of this disclosure, commercially available and commonly used proteins were used. However, it is to be recognized that other commercial or customized antigens or antibodies may also be used.

The HIV-1 assay demonstration utilized two commercially-sourced, purified recombinant proteins: envelope gp41, and capsid antigen p24. For the syphilis treponemal assay, commercially-sourced, recombinant proteins Tp47 and Tp17 were used. Tp47 and Tp17 are commonly used in treponemal-specific syphilis immunoassays. Note that treponemal-specific assays do not readily distinguish between active, latent, and treated syphilis infection. The platform described here, however, is amenable to the addition of a non-treponemal antibody detection component, as has been described in the literature.

Due to the high level of genomic and antigenic variability associated with HCV, anti-HCV antibody screening typically depends on multiple antigenic targets. For instance, a number of FDA-approved enzyme immunoassays rely on combinations of recombinant proteins and peptides. Consistent with the need for HCV antigen multiplexing, four commercially-available HCV recombinant proteins were used in this demonstration, including recombinant core protein (nucleocapsid, p22 fusion protein); full length NS3 (c33c); a mosaic recombinant including NS4 immunodominant regions; and a recombinant which contains HCV nucleocapsid, NS3, NS4, and NS5 immunodominant regions, which is also referred to as the multiple epitope antigen in this disclosure.

Assay Reagents.

Other biological reagents include purified human IgG (Sigma, St. Louis, Mo.), goat anti-human IgG (Thermo Scientific, Rockford, Ill.), and goat anti-human IgG conjugated with fluorescent dye (DyLight649, KPL, Inc.). Assay reagents include bovine serum albumin ("BSA", Sigma Life Science, St. Louis, Mo.), phosphate buffered saline ("PBS", Fisher Scientific, Rockford, Ill.), Blocker Casein in PBS (Thermo Scientific, Rockford, Ill.), and Tween20 (Thermo Scientific, Rockford, Ill.).

Clinical Samples.

Five sets of clinical samples were used to characterize the system. A total of 251 different clinical samples were processed in this example.

Commercial Controls.

Well-characterized human plasma and serum samples with known antibody reactivity for each of the three pathogens were commercially-sourced. These samples included four with known HIV-1 antibody reactivity, four with known *T. pallidum* antibody reactivity, and four with known HCV antibody reactivity.

HIV-1 Antibody Reactive Samples.

A total of 25 human serum samples with known HIV-1 Western Blot reactivity were sourced under an Institutional Review Board ("IRB")-approved protocol by the University of California, San Diego Medical Center (UCSD). Co-infection status was not known for the majority of these samples at the time of the assay described herein.

Syphilis Samples.

A collection of 30 de-identified sera known positive for syphilis infection were sourced from the Colorado Department of Public Health and Environment (CDPHE, Denver, Colo.). Syphilis reactivity was determined at the CDPHE Laboratory using rapid plasma regain ("RPR") and *T. pallidum* particle agglutination ("TPPA"). The HIV serostatus of each of these samples was not known upon receipt from the CDPHE. All 30 sera were also characterized with an FDA-approved HIV-1/2 RDT (Trinity Uni-Gold™ Recombigen® HIV).

Co-Infection Samples.

A collection of de-identified clinical samples from existing sample archives were coordinated with IRB approval by UCSD. Samples were selected for likely HIV, HCV, hepatitis B virus, and/or syphilis infection. UCSD clinical samples were all characterized for HIV and HCV infection on a Siemens Centaur™ clinical analyzer. Syphilis samples were tested by RPR with confirmation by TPPA. The UCSD Co-Infection Collection includes a large number of highly complex pathogen antibody and antigen reactivities, as commonly encountered in HIV and HCV infected individuals. In addition to HIV, HCV, HBV, and/or syphilis infection, many of these samples have positive reactivities for *T. gondii*, CMV, Epstein-Barr virus, and various human herpes viruses.

Negative Control Sera.

Human serum controls were commercially-sourced, and were vendor-certified as HIV, HCV, and RPR negative. *T. pallidum* antibody reactivity was not provided by the vendor for this collection. In the event of a positive *T. pallidum* antibody result using the present system and method, reference testing was performed on those specific samples. Reference tests for *T. pallidum* included TPPA (Fujirebio, Malvern, Pa.), a syphilis RDT (SD Bioline, Korea), and Treponemal Enzyme Linked Immunosorbent Assay ("ELISA", Trep-Sure, *Phoenix* Biotech, Ontario, Calif.). *T. pallidum* reference testing was not performed on samples that were negative by RPR and negative using the present system.

Whole Blood Samples.

Because one of the important uses of the present system and method will be in point-of-care settings, it is important to evaluate the performance of the system on whole blood samples. Whole blood was sourced under an IRB-approved protocol from HIV-positive donors at the UCSD Antiviral Research Center ("AVRC"). Venipuncture samples were collected in Ethylenediaminetetraacetic Acid ("EDTA") blood collection tubes (Lavender Cap BD Vacutainer®) and shipped overnight to the site where the assays were run within two hours of receipt of the samples (i.e., within 24 hours of draw). After whole blood samples were processed, the tubes were centrifuged and the plasma fraction was also assayed.

As shown in the examples, the HIV-1 assay have 100% agreement with known seroreactivity on a collection of 82 HIV Ab-positive and 142 HIV Ab-negative samples, including multiple samples with HCV and syphilis co-infection. The treponemal-specific syphilis assay correctly identifies 67 of 68 *T. pallidum* Ab positive and 100 of 102 *T. pallidum* Ab negative samples. The HCV assay correctly identifies 59 of 60 HCV Ab-positive and 120 of 121 HCV Ab-negative samples. Multiplexed assay performance on whole blood samples is also demonstrated.

Assay Cartridge and Instrument.

The system described in the examples here combined single-use disposable assay cartridges with a reader instrument. Fluorescence assays were illuminated and imaged using a multi-mode planar waveguide technology. Various types of planar waveguides have been used in biosensor and immunoassay applications for decades, and are the subject of several technical reviews. Briefly, a light source (typically a laser) was directed into a waveguide substrate where it propagated by total internal reflection ("TIR") at the interface between the high index of refraction waveguide (glass or plastic) and the surrounding medium (air or aqueous solution). The present system uses a planar waveguide system as disclosed, for example, in aforementioned U.S. patent application Ser. No. 12/617,535.

Assay Procedure.

Samples are processed in cartridges on the bench top at ambient temperature, which in this study was approximately 20 to 25° C. Since the assay procedure may be performed independently of the reader instrument, sample cartridges may be batch processed, with up to 30 run in parallel, for example. A tilt rack, such as that discussed below with respect to FIGS. 47-49, may be used during the assay to facilitate the batch processing, if desired. Sample volumes for the disposable cartridge are 6 microliters of serum or plasma or 12 microliters of whole blood, making the cartridge compatible with finger stick capillary samples. The larger volume for the whole blood samples is believed to be required to compensate for the cell volume.

Results presented here are based on the following sample processing procedure. A 6 microliter aliquot of serum or plasma is diluted in 194 microliters of a diluent (PBS, 0.5% casein, 0.05% Tween20). 175 microliters of this diluted sample mixture is then loaded into the cartridge input port by transfer pipette. Passive flow through the cartridge during a 15 minute incubation occurs independently of any user interaction. 175 microliters of wash buffer (PBS, 0.1% Tween20) is then added to the input port and allowed to flow through the cartridge for 3 minutes, followed by 175 microliters of dye-conjugated anti-human IgG in a second diluent (PBS, 1 mg/mL BSA and 0.05% Tween20) and allowed to incubate for 10 minutes. The total per cartridge assay time, in the present example, is approximately 28 minutes. While the fluorescence signal generated at the assay region of the cartridge may change over time, the cartridge may be read on the reader instrument any time within an hour of sample processing without affecting the final test result. Read time and data processing in the reader instrument is approximately 30 seconds per cartridge.

Custom image processing software has been developed for reaction site finding, intra-site fluorescence signal intensity measurement and normalization. After results reporting, the cartridge is removed from the reader instrument and disposed as biohazard waste, and the next processed cartridge may be inserted into the reader instrument. The combination of parallel cartridge processing, large read window, and rapid analysis allows more than 100 samples per work shift to be processed.

Results: Multiplex Assay of HIV, Syphilis and HCV on the Same Cartridge

FIGS. 28-29 show an exemplary array layout and representative images for the multiplex HIV/Syphilis/HCV assay.

FIG. 28 provides an exemplary layout of the HIV-1/Syphilis (*T. pallidum*)/HCV array map along with images from a representative set of clinical samples. In-array control features include printed human IgG, anti-human IgG, and print buffer controls. These features should yield fluorescence signal in an acceptable range for a test to be considered valid, ensuring that sample and fluorescently labeled detect antibody were added to the cartridge and that the cartridge was properly illuminated. In particular, the 30 feature array (2 rows by 15 columns) of the present example includes pathogen-specific printed antigens as well as multiple in-assay controls. Dye-labeled bovine serum albumin ("BSA") sites serve as corner markers (C1) for imaging. These sites are not used in the analysis in this embodiment. Printed human IgG (C2) serves as a procedural control for the dye-labeled detect antibody. Printed anti-human IgG (C3) serves as a sample control. Print buffer sites serve as negative controls, and monitor for any unusual non-specific binding. Excessive fluorescence signal on the negative control spotsites yields an invalid test result.

The human IgG and anti-human IgG control sites were designed to give fluorescence signal comparable to a typical seropositive sample. Obviously, total human IgG and the goat anti-human IgG fluorescent conjugate were both in large excess relative to the specific antibodies reacting with each of the antigen sites. The IgG print concentration were adjusted such that the positive control signals fell into an appropriate range.

Images from four clinical plasma samples are shown in FIG. 29, along with background-subtracted reaction site signal intensities for the pathogen-specific antigens. The clinical sample images in FIG. 29 are a representative sampling of images generated in the 28 minute cartridge assay. Positive and negative controls are present in these exemplary assays, and the printed antigen sites show different intensities for different individual samples. Based on reference test methods, samples (A) through (C) are each reactive for one pathogen and negative for the other two. Sample (D) is antibody reactive for all pathogens as indicated by all array antigen sites yielding positive signal. In particular, samples (A) to (C) are each mono-infected, with reactivity to HIV Ab (A), *T. pallidum* Ab (B), and HCV Ab (C). Sample (D) has Ab reactivity to all three pathogens both in the reference methods and the assay system, as described herein.

The fluorescence arrays are also quantitative. The table in FIG. 30 provides quantitative antibody-antigen signal intensities associated with each reaction site. Results for each reaction site in the array are reported as background-subtracted and normalized fluorescence signal intensity. Background signal is an average of the signal on negative reference sites adjacent to the antigen site of interest. The intensity of the printed human IgG site signal is utilized for normalization; and the reported intensity is thus a dimensionless number. Slightly negative numbers result when the signal on the antigen site is lower than the adjacent negative control. All negative numbers encountered are invariably close to zero. Dynamic range of the current reader instrument is approximately 3.5 logs. Normalization by the signal of the anti-human IgG spots compensates for potential differences in coupled and collected light between different instruments or cartridges, as well as for possible changes in the fluorescent conjugate solution. Decisions about the reactivity of a sample with each disease antigen are based on comparing the normalized antigen signal to a pre-determined cutoff value. For each antigen, the cutoff value is established by reviewing the signals obtained from a large number of assays with samples known to be positive and negative for each disease. The cutoff value may be chosen to accurately distinguish positive from negative signals for the specific antigen. Significant changes to the antigens and the print or assay conditions may require establishment of new cutoff values for the various antigens in the assay.

Figure 31:
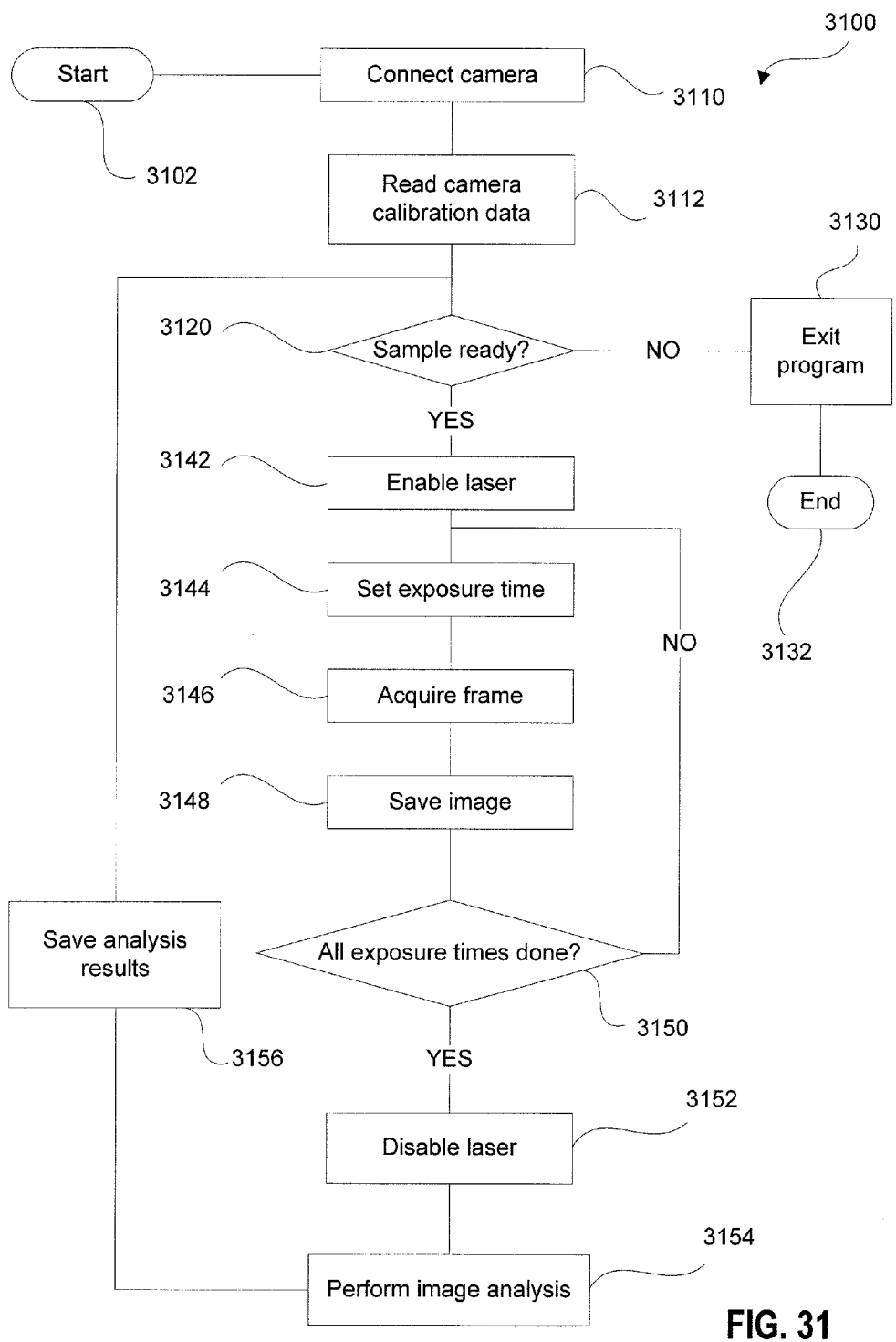
FIG. 31 is a flow chart illustrating an exemplary process for operating the reader instrument, in accordance with an embodiment.
Figure 32:
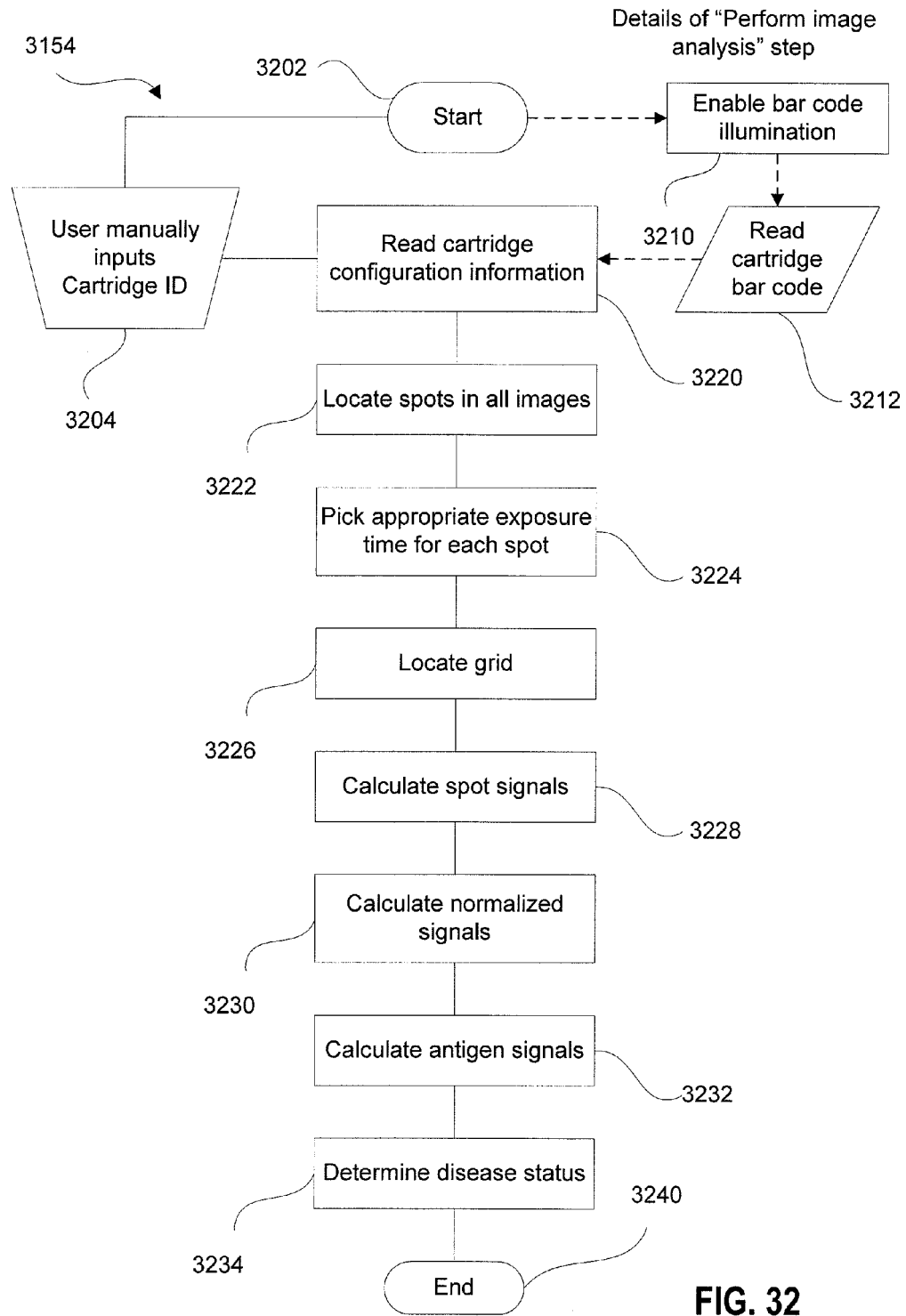
FIG. 32 is a flow chart illustrating further details of an image analysis step in the exemplary process as illustrated in FIG. 31, in accordance with an embodiment.

FIGS. 31 and 32 illustrate details of an exemplary software processing used to calculate the results as summarized in the table in FIG. 30. FIG. 31 shows a flow chart, illustrating a process 3100 for operating a reader instrument, in accordance with an embodiment. Process 3100 is initiated by a start step 3102, which may be actuated by, for example, the insertion of cartridge 3110 into reader instrument 100. A camera (or another suitable imaging device, e.g., sensor 128 of FIG. 2) is connected within reader instrument 100 and brought online in a step 3110. The camera is calibrated in a step 3112. The calibration of the camera may be performed by, for example, reading in externally-supplied calibration data and adjusting the camera settings as appropriate. In a decision 3120, a determination is made as to whether a sample is ready within reader instrument 100. If, for example, cartridge 110 is incorrectly inserted into reader instrument 100 such that cartridge 110 cannot be correctly imaged by the camera, then the result of decision 3120 is "NO", the sample is not ready, and process 3100 proceeds to a step 3130 to exit the program, and the process is ended in an end step 3132.

Continuing to refer to FIG. 31, if the result of decision 3120 is "YES", the sample is ready within reader instrument 100, and process 3100 proceeds to a step 3142, in which a light source is enabled. The light source may be, for example, a laser or a light-emitting diode (LED) of an appropriate wavelength and output power for illumination of the sample being evaluated. Additionally, a "watchdog circuit" may be activated, so as to safely power down the light source in case of any malfunction. In a step 3144, the exposure time of the light source is set. For example, a certain number and durations of exposure times may be preset in process 3100. An image frame is acquired in a step 3146, and the acquired image is saved to memory in a step 3148. In a decision 3150, a determination is made as to whether images have been taken for all preset exposure times. If the result of decision 3150 is "NO", not all exposure times are done, then process 3100 returns to step 3144, and the exposure time setting and image acquisition steps are repeated. If the result of decision 3150 is "YES", images have been acquired at all preset exposure times, then the light source is disabled in a step 3152. The acquired and saved images are then analyzed in a step 3154, and the analysis results are saved to memory in a step 3156. As an alternative, step 3154 and 3156 may be performed at peripheral device 1980 of FIG. 19, such as an external computer, rather than being integrated onboard reader instrument 100. Following step 3156, process 3100 returns to decision 3120. If a new sample cartridge has been inserted, then steps 3142-3156 are repeated. Otherwise, process 3100 is ended with exit program step 3130 and end step 3132.

Referring now to FIG. 32, further details of step 3154 of FIG. 31 are described. Step 3154 is initiated at a start step 3202 then, in a step 3204, a user manually inputs a cartridge identification number ("cartridge ID") into reader instrument 100. Alternatively, reader instrument 100 may include a barcode reader arrangement. In this case, a barcode illumination is enabled in a step 3210, and a barcode, including cartridge ID and placed on cartridge 110, is read into reader instrument 100. Based on the cartridge ID, the appropriate cartridge configuration information is read into reader instrument 100. Cartridge configuration may include, for example, specific reagents used on cartridge 110, layout of any printed protein array sites, and any other factors that may influence the image analysis. Once the cartridge configuration information has been read in step 3220, then reaction sites are located in all saved images in the memory, in a step 3222. For example, for cartridges with circular printed antigen sites, step 3222 may involve circle finding routines. In a step 3224, the acquired images for each reaction site for the various exposure times are compared, and the "best" acquired image for each reaction site is identified. For instance, the selected reaction site may correspond to the longest exposure time that does not saturate the camera. Then, in a step 3226, a grid corresponding to the printed protein array (such as shown in FIGS. 22 and 23) is located. For instance, step 3226 may include identifying the centers of the circles found in step 3222, combining this data with geometry information included in the cartridge configuration, then refining the analysis according to a least squares fit of predefined parameters in the cartridge configuration.

Still referring to FIG. 32, a reaction site signal is calculated for each reaction site in the printed protein array in a step 3228. In particular, as an example, the radius of each reaction site is calculated as an average of found reaction sites, the raw signal is integrated over the reaction sites, then a per-pixel average (at the camera) is calculated as the reaction site signal. In a step 3230, a normalization process is implemented in order to calculate normalized signals for the reaction sites using, for instance, a power normalization algorithm. In a step 3232, signals at each antigen site is determined to calculate antigen signals. For instance, step 3232 may involve the identification of the antigen sites (in accordance with the cartridge configuration), then averaging the signals at the antigen sites. Additionally, a "look-up" table may be used as an error control, such as in the case of noisy signals, highly-fluctuating signal intensity, etc. Finally, the calculated antigen signals are compared against predetermined cut-offs so as to determine the disease status for the various antigens in a step 3234. The image analysis step is ended in an end step 3240, and the process proceeds to step 3156 of FIG. 31.

Figure 19:
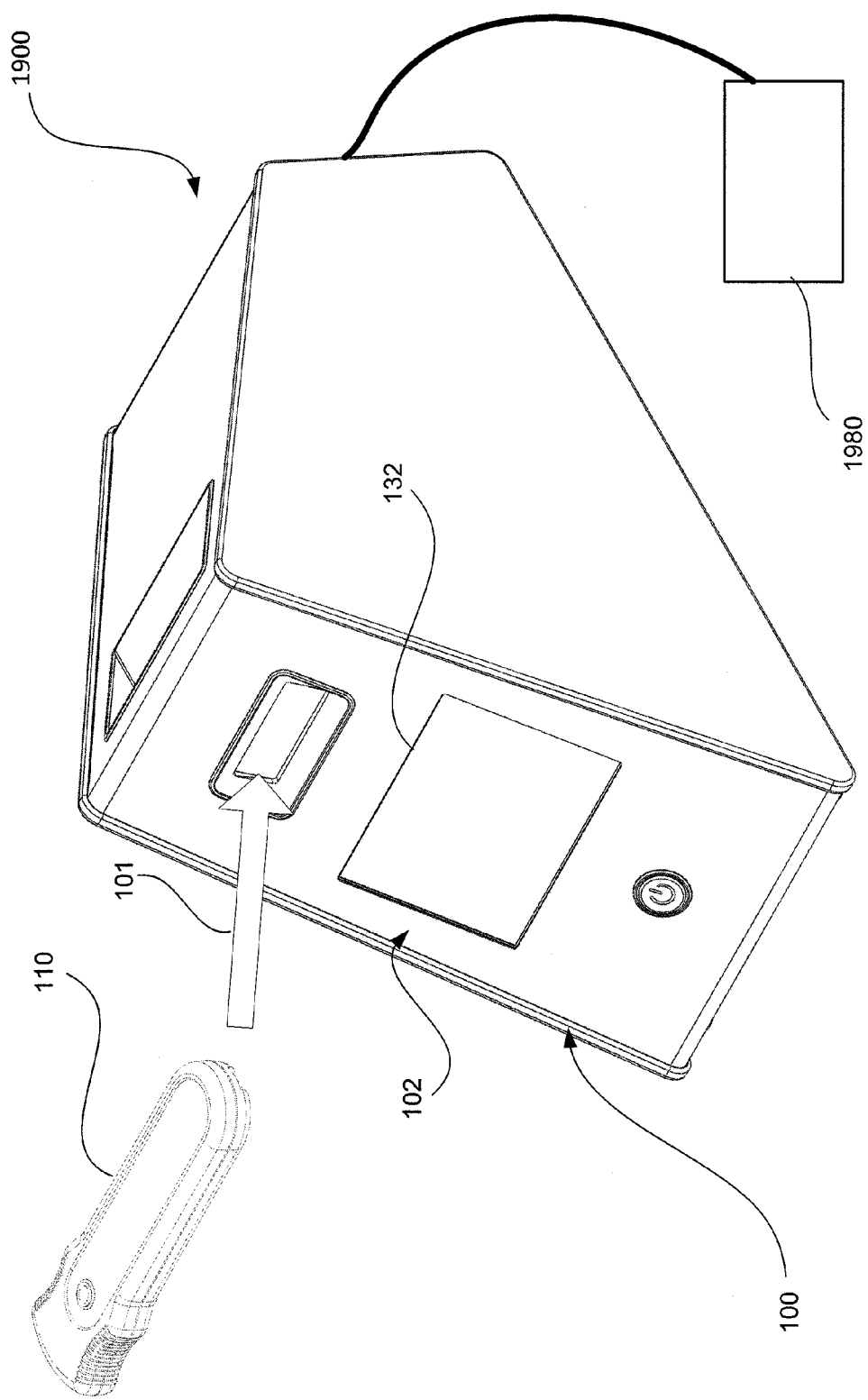
FIG. 19 is a perspective view of a reader instrument including a peripheral device, in accordance with an embodiment.
Figure 20:
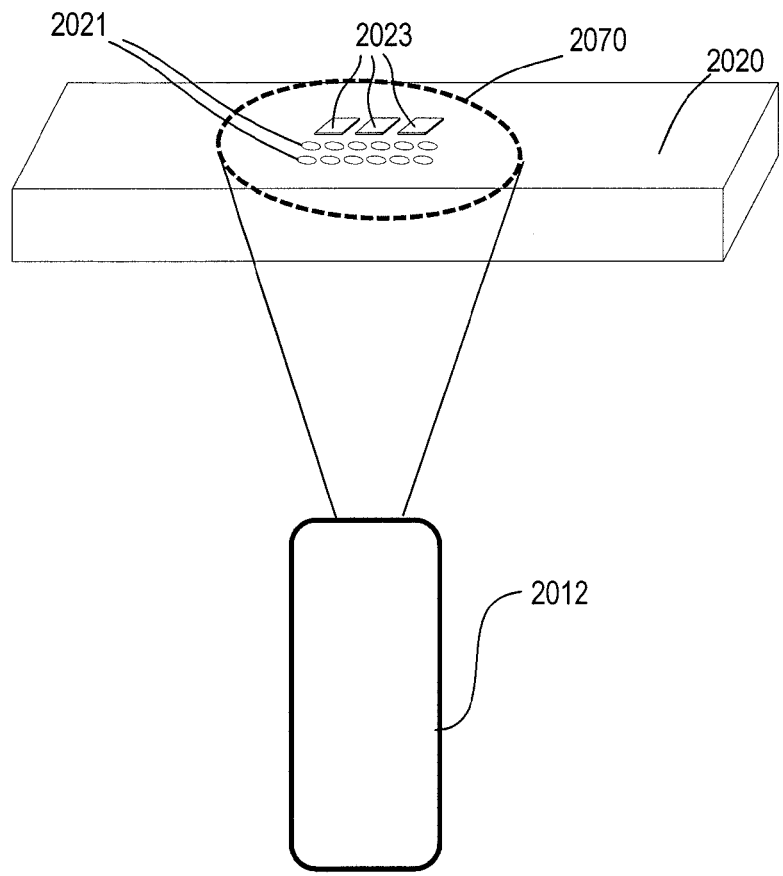
FIG. 20 is a view showing an imaging system field of view suitable for reading both markings and analyte markers within the same field of view, in accordance with an embodiment.

As previously described, the specific steps of process 3154 as shown in FIG. 32 may be performed onboard reader instrument 100 or at peripheral device 1980 of FIG. 19.

Clinical Results

Figure 33:
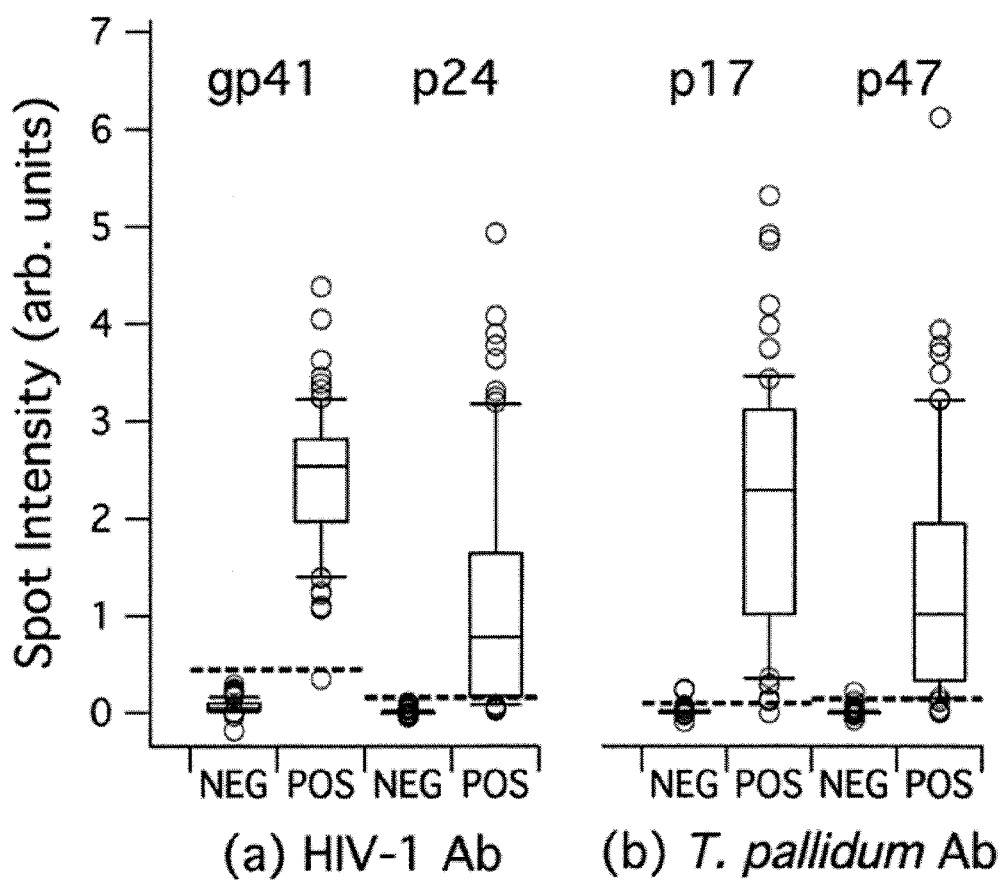
FIG. 33 shows the antibody reactivity for clinical samples with known HIV-1 and *T. pallidum* serostatus, as analyzed with an exemplary system, in accordance with an embodiment.
Figure 34:
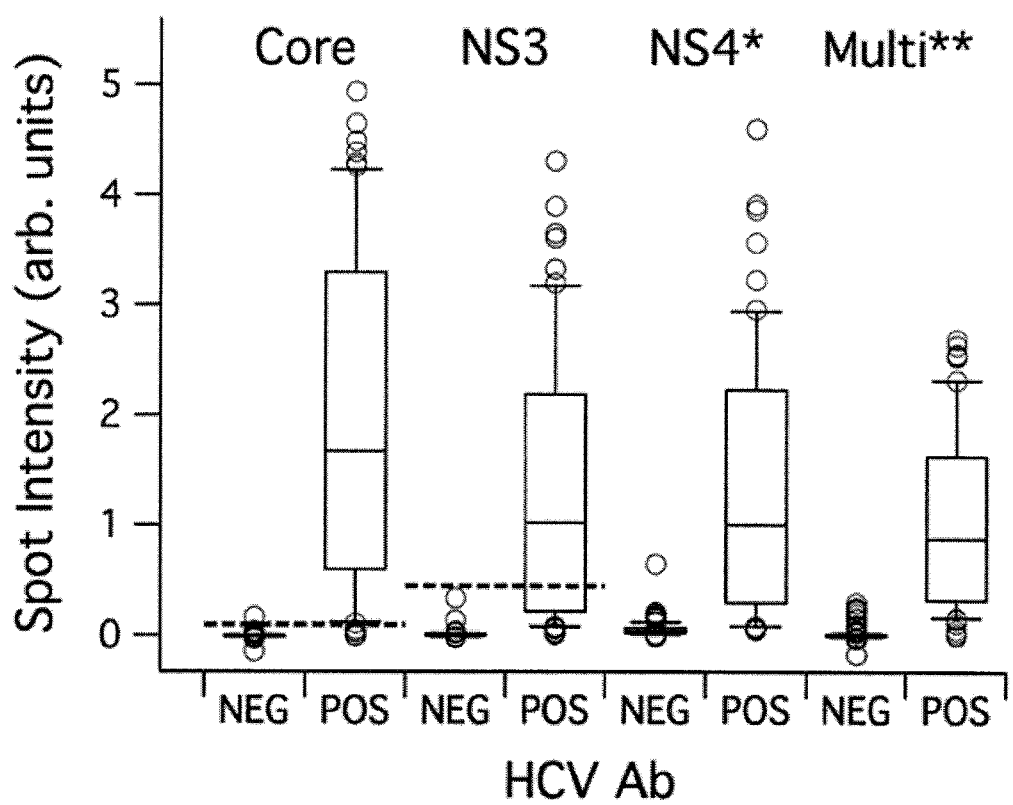
FIG. 34 shows the antibody reactivity for 181 clinical samples with known HCV antibody serostatus (60 positive and 121 negative), as analyzed with an exemplary system, in accordance with an embodiment.

With the combination of commercial positive controls, the UCSD HIV-1 samples, the CDPHE Syphilis samples, the UCSD Co-Infection samples, and the negative controls, a total of 251 different samples (serum and plasma) are presented in this clinical results section. It is emphasized that antibody reactivity against all antigens in FIGS. 33 and 34 is measured simultaneously for each sample.

HIV-1 Antibody Assay Results.

A total of 224 samples in the collection had known HIV-1 seroreactivity status, with 82 HIV-1 Ab positive and 142 HIV-1 Ab negative. Antibody reactivity (signal as described above) against the two HIV antigens in the array (gp41 and p24) are linked to the known HIV Ab reactivity status and plotted in FIG. 33(*a*). Reaction site signal intensity is the background subtracted, normalized intensity, as discussed above. The horizontal solid bar in each box represents the median; upper and lower boundaries of the boxes are the 75th and 25th percentiles; and the upper and lower whisker bars are the 90th and 10th percentiles, respectively. The open circles represent samples with values above and below the 90th and 10th percentiles. The dashed lines are empirically derived cutoffs. FIG. 33(*a*) shows antibody reactivity results for a total of 224 samples with known HIV-1 Ab reactivity status (82 positive and 142 negative).

Ideally, samples that are known HIV Ab negative should show little or no intensity on the HIV antigen sites. As expected, gp41 and p24 signal results are clustered near zero for these negative samples. We note that the gp41 sites do show some cross-reactivity, with normalized signals between 0 and 0.4 on this scale. For the HIV Ab positive samples, we see a distribution of intensities. A strong gp41 antibody response is expected in seroconverted individuals represented in this collection, and the FIG. 33(*a*) gp41 results are consistent with this expectation. One known HIV Ab positive sample does show low signal on the gp41 site. This particular sample yielded robust signal on the p24 site. For the collection, reactivity against the p24 antigen is varied, as seen in FIG. 33(*a*).

The data plots of FIG. 33(*a*) are used to establish empiric cutoff values that will be used for subsequent signal/cutoff ("S/CO") calculations. Cutoffs are set near the highest signal negative sample in the collection. Increasing the cutoff value will yield a more specific assay (fewer false positives). Decreasing the cutoff will yield a more sensitive assay (fewer false negatives). Given that the antibody reactivity status of the samples in this collection was known, individual antigen cutoffs were adjusted empirically to optimize "effective" sensitivity and specificity. We note that the results obtained in this study are based on a self-referential dataset, i.e., we are applying the cutoff to the same data used to generate the cutoff. We therefore do not report results in terms of sensitivity and specificity. On the scale shown in FIG. 33(*a*), the gp41 and p24 cutoffs are set at a value above the highest signal negative sample in the collection (cutoffs are 0.45 and 0.16, respectively). If it is assumed that a S/CO>1 for either antigen constitutes overall HIV-1 Ab reactivity for that sample, then the cutoffs as defined yield 100% agreement between the multiplex assay as described herein and the reference result.

Syphilis Assay Results.

A total of 170 samples in the collection had known *T. pallidum* antibody reactivity status, including 68 treponemal positive and 102 treponemal negative samples. Results for the treponemal antigens p17 and p47 are provided in FIG. 33(*b*). FIG. 33(*b*) shows antibody reactivity results for a total of 170 samples with known treponemal Ab reactivity status (68 positive and 102 negative). As described above, cutoffs were empirically determined and are indicated on the plots. Applying these cutoffs to the 170 samples, we report treponemal Ab reactivity on 67 of 68 known treponemal Ab reactive samples (one false negative). The assay correctly identifies 100 of 102 treponemal negatives (two false positives). Next steps will be to improve specific activity and minimize non-specific binding to the treponemal antigen sites.

Hepatitis C Assay Results.

A total of 181 samples had known HCV antibody reactivity, including 60 HCV Ab positive and 121 HCV Ab negative. Results for the four recombinant antigens are provided in FIG. 34, which shows the antibody reactivity in the exemplary assay for 181 clinical samples with known HCV antibody serostatus (60 positive and 121 negative). Reaction site signal intensity is the background subtracted, normalized intensity described in the text. Antibody reactivity against all antigens is measured simultaneously for each sample. The dashed lines are empirically derived cutoffs for the core and NS3 recombinant antigens. The synthetic NS4* and Multi** multiple-epitope antigens showed relatively high signals on the HCV Ab negative samples, so cutoffs for these two antigens were not used in subsequent analyses.

Continuing to refer to FIG. 34, a large spread of antibody reactivity signals is observed, as expected. The core and NS3 antigens appear to provide the best overall performance in terms of distinguishing positive from negative. The two multiple epitope antigens (NS4* and Multi) did not offer a benefit over the core and NS3 antigens in this assay. Using these results, cutoffs were set for the core and NS3 antigen as described above. With the selected cutoffs, the assay correctly identifies 59 of 60 positive and 120 of 121 negative HCV samples. FIG. 34** shows a large number of samples (positive and negative) near the cutoff values. Antigen selection and activity improvements are required to improve robustness of the HCV assay.

Whole Blood Assay Results.

Because point-of-care is the target application of the present system, whole blood performance of the assay system is an important demonstration. Lateral flow based RDT's typically incorporate a sample pad material designed to capture red blood cells ("RBCs") without promoting hemolysis, as the RBCs and hemoglobin can interfere with the colorimetric read of the device. The present system has no such requirement; that is, 6% whole blood in buffer may be added directly to the device with no separation of cellular components prior to running the standard assay protocol described above.

Figure 35:
FIGS. 35-37 show representative images and a comparison of whole blood and plasma performance on an exemplary system, in accordance with an embodiment.
Figure 36:
Figure 37:
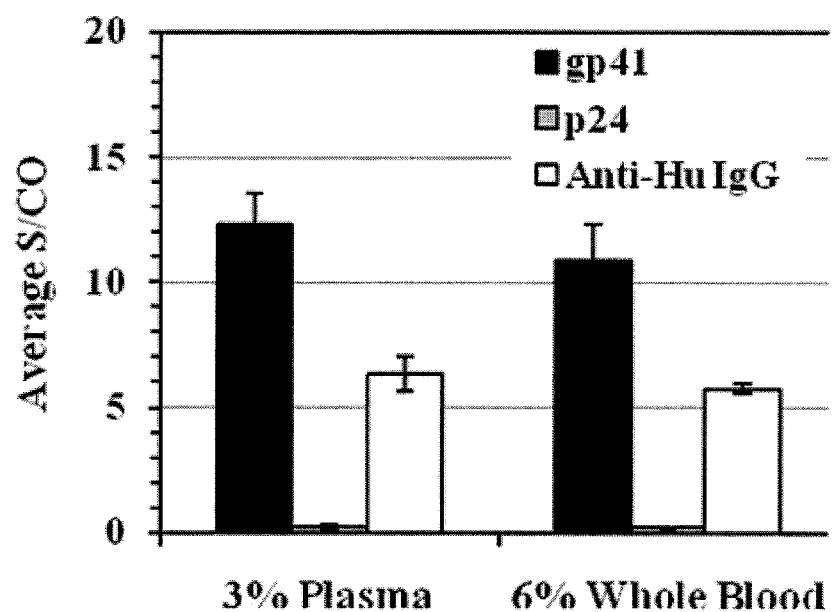

Representative whole blood assay results are provided in FIGS. 35-37, which present whole blood performance in direct comparison to plasma from the same blood tube. FIG. 37 shows comparison of whole blood and plasma performance on the exemplary system. Cartridges were processed with 6% whole blood or 3% plasma from the same venipuncture sample approximately 24 hours after draw. The larger volume of whole blood was to approximately compensate for cell volume. The array layout was as in FIG. 28. Images for the whole blood and plasma from this HIV-positive sample were essentially identical (as shown in FIGS. 35 and 36), demonstrating that there is no cellular or hemoglobin-induced interference in the system. The bar graph provides quantitative output for the gp41, p24, and anti-human IgG sites on the arrays, demonstrating the same quantitative signal profile for the whole blood and plasma samples. This particular sample had strong reactivity to the gp41 antigen but very little reactivity to p24.

Note that the anti-human IgG is printed at very low concentration in the array, with activity tuned to give signal on the same scale as positive antigen sites. Total IgG is in large excess in the sample. Data presented are mean values for three replicate cartridges for each sample type. Error bars represent one standard deviation.

Reproducibility.

The whole blood and plasma assay described above and shown in FIG. 6 include triplicate measurements of the same blood or plasma sample (6 cartridges total), providing an initial assessment of system reproducibility. Defining % coefficient of variation ("% CV") as the standard deviation of the three measurements divided by the mean, the following results were observed. For the plasma samples, gp41 S/CO % CV was 10%. For the whole blood samples it was 13%. For the anti-human IgG sites, the plasma samples gave 11% CV and the whole blood gave 4%. These are reasonable initial results for a 28 minute whole blood assay; CVs are expected to improve as manufacturing controls are augmented during scale-up.

Example 9

Simple Fluorescence Sandwich Assay

Figure 38:
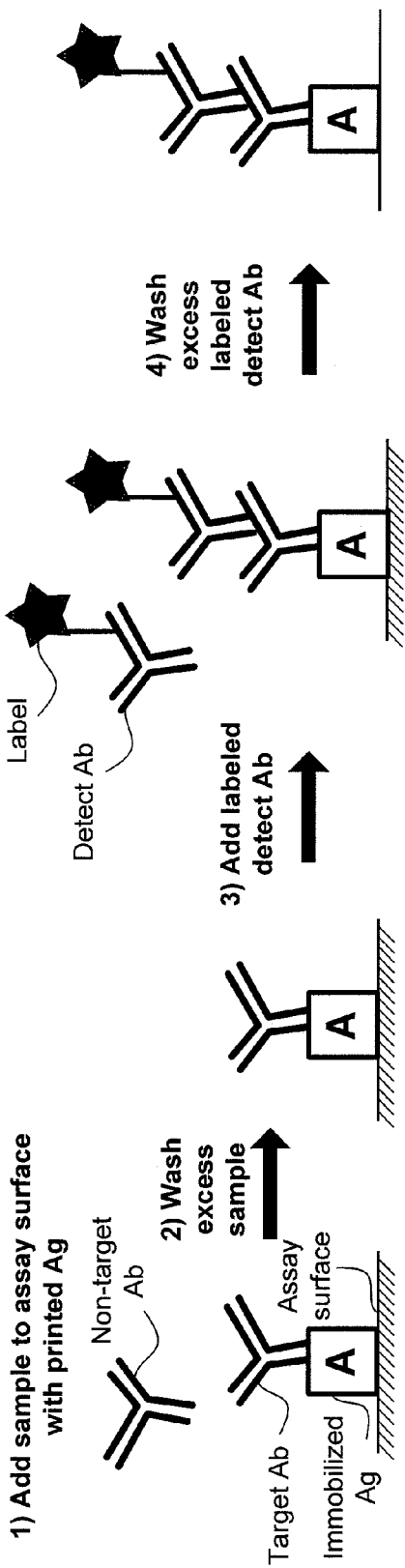
FIG. 38 shows a series of diagrams illustrating the steps of an indirect fluorescence assay.

FIG. 38 shows a series of diagrams representing the steps of an exemplary, indirect fluorescence assay. The goal of this type of assay is to detect and identify the presence of specific antibodies in a biological sample. In one configuration, one or more antigens ("Ag") are immobilized on an assay surface, such as the walls of a microwell device (e.g., a 96-well microtiter plate). The antigen can be, for example, a purified natural protein, recombinant protein, synthetic peptide, or other biological molecular representing an immunogenic target. For commercially prepared immunoassays, this antigen immobilization step is performed during manufacture of the immunoassay kit. At the time of use, a biological sample is introduced to the well (i.e., Step "1") shown in FIG. 38). The biological sample may potentially include target and non-target antibodies ("Ab"). If present, target antibodies bind to the immobilized antigens during an incubation period. A wash step is typically used to remove excess biological sample (i.e., step "2") shown in FIG. 38), then a labeled detect antibody is added to the well (i.e., Step "3") shown in FIG. 38). For example, in an assay for specific human antibodies, the detect antibody could be a goat anti-human IgG conjugated with horseradish peroxidase ("HRP"). The label may be an enzyme (HRP, alkaline phosphatase, luciferase, etc.), for use with colorimetric or chemiluminescence signal transduction. The label could also be a fluorescent dye, lanthanide, nanoparticle, microparticle, light scattering particle, or some other labeling mechanism. A final wash step is typically used to remove excess labeled detect antibody (i.e., step "4") shown in FIG. 38), and the microwell device is then read by eye (e.g., in a colorimetric assay) or through some appropriate instrumentation (e.g., absorbance plate reader, chemiluminescence detector, or fluorescence detector).

In another configuration (not shown), antigens may be printed to a solid substrate that is then incorporated in a fluidic cartridge that includes a fluid inlet port. The antigens may be printed, for example, in a spot or stripe, and multiple antigens may be printed in an array format. Similarly to the microwell protocol described above, a biological sample is added to the fluidic cartridge and, if present, target antibodies bind to the printed antigens. After a wash step to remove excess biological sample, a labeling step, then another wash step to remove excess labeled detect antibody, the fluidic cartridge may be imaged using a reader instrument (see, for example, Myatt, C. J. et al., Low-cost, multiplexed biosensor for disease diagnosis, Proc. SPIE 7167 Frontiers in Pathogen Detection: From Nanosensors to Systems, 716703 (2009), which is incorporated herein in its entirety).

While the indirect fluorescence assay has proven utility, the multi-step process may be undesirable for certain applications, particularly in the context of rapid, point-of-care or point-of-need testing. A potentially simpler workflow approach is known in the field as the "double antigen sandwich" method (See, for example, U.S. Pat. No. 6,120,990 to Brust et al. and U.S. Pat. No. 7,629,295 to Wienhues et al.). The double antigen sandwich method takes advantage of the multi-valent nature of immunoglobulin ("Ig") molecules. Instead of the anti-immunoglobulin detect format used in the indirect fluorescence assay described above, the detect reagent is a labeled antigen containing the same binding epitope as the immobilized antigen. The antigen may be, for example, a purified natural protein, recombinant protein, synthetic peptide, or other biological molecular representing an immunogenic target. The label may be an enzyme (e.g., HRP or alkaline phosphatase), for use with colorimetric or chemiluminescence signal transduction. The label may also be a fluorescent dye, nanoparticle, microparticle, light scattering particle, or some other labeling system. In the double antigen configuration, the target antibody is sandwiched between the surface immobilized antigen and the labeled detect antigen.

There may be several advantages to the double antigen sandwich approach. Importantly, the format provides detection of multiple immunoglobulin types (IgG and its subtypes, IgM, etc.). The format also is amenable to simplified workflow protocols, as wash and detect reagent steps may be eliminated.

Various versions of the double-antigen sandwich concept have been described in the literature and incorporated into commercially-available assays, including, for example, tests for detection of anti-HIV antibodies such as SD Bioline HIV-1/2 3.0 (Standard Diagnostics, Inc.), Uni-Gold™ Recombigen® HIV (Trinity Biotech plc), ARCHITECT™ (Abbott Laboratories), Determine® (Alere), and COBAS CORE Anti-HIV-1/HIV-2 EIA DAGS (CORE HIV-1/2) (Roche). See also Zaaijer et al., The Lancet, vol. 340, pp. 770-772, 1992, and Miolini et al., Journal of Immunological Methods, vol. 20, pp. 25-34, 1978). This technique has become known as the "third generation" of HIV antibody detection because it is capable of identifying a broader range of antibody types than previous "first" and "second" generation tests. The technique is also often incorporated into the current "fourth" generation HIV antigen/antibody combination assays.

The simple labeled antigen assay technique, as described herein, provides a number of advantages over existing technology. For example, current third- and fourth-generation HIV diagnostic assays that use the double antigen sandwich approach require integration into an immunochromatographic (e.g., lateral flow) device, which requires colorimetric visual interpretation, or into an expensive, fully-integrated, automated system with automated fluidic handling and optical readout. The labeled antigen assay, in the present embodiment, generates signal through fluorescence imaging of captured complexes with evanescent illumination. As described herein, the combination of labeled antigens, evanescent illumination, and fluorescent detection provides advantages of simplicity (i.e., minimal user interactions), speed (i.e., time to result), multiplexing (i.e., multiple assay results for a single sample) and compatibility with complex sample matrices (e.g., whole blood). In addition, the system described herein provides a means to perform assays based on kinetic data, enables numerous in-assay controls, and can provide means for automatically timing the assay. The approach also allows fluorescence signal acquisition of bound complexes on the surface without the need for washing away of residual unbound fluorescent markers in the liquid volume above the surface, thus allowing a truly one step process from biological sample introduction through signal acquisition. While a wash step may still be useful in some applications of the labeled antigen assay described herein, the potential elimination of the wash step may provide a significant advantage over existing assay protocols.

Figure 39:
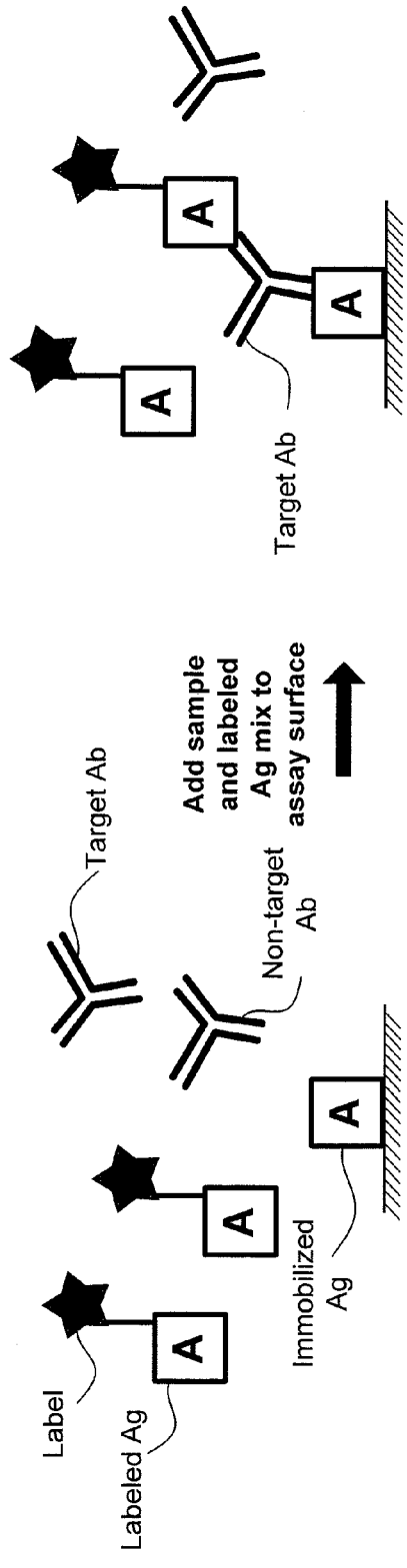
FIG. 39 shows a series of diagrams illustrating a labeled antigen assay, in accordance with an embodiment.

FIG. 39 shows a diagrammatic representation of a labeled antigen assay technique, in accordance with an embodiment, which is a further simplification of the aforementioned double antigen sandwich technique. As shown in FIG. 39, an antigen is immobilized onto an assay surface. A labeled antigen, including the same antigenic epitope as the immobilized antigen, serves as the detect reagent. When the specific target antibody is present in the biological sample, a double antigen sandwich is formed at the assay surface.

Figure 40:
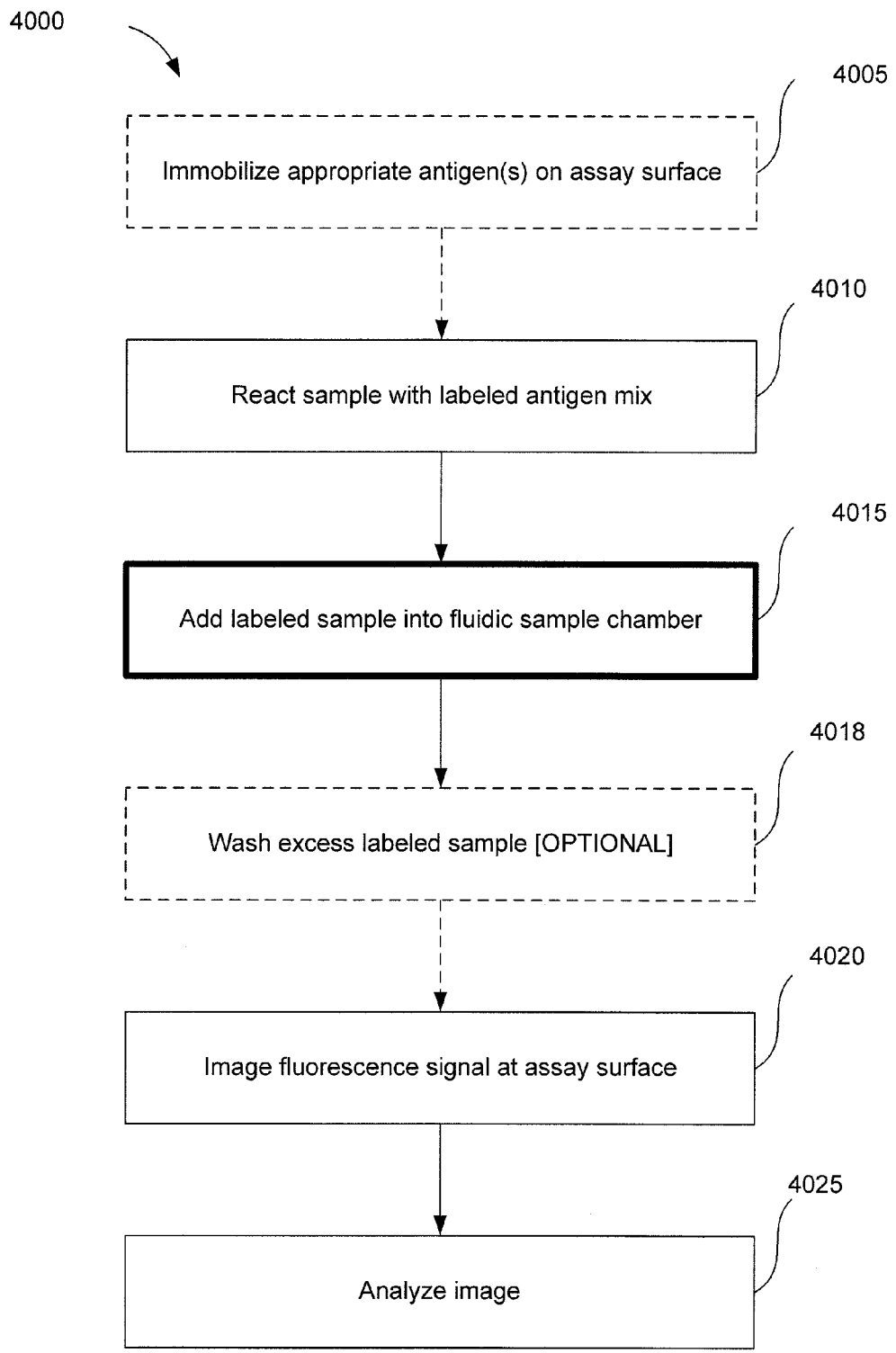
FIG. 40 shows a flow chart illustrating the labeled antigen assay process, in accordance with an embodiment.

FIG. 40 shows a flow chart, summarizing an exemplary labeled antigen assay process flow, in accordance with an embodiment. An assay process 4000 begins with an antigen immobilization step 4005, in which one or more appropriate antigens as well as potentially positive and negative controls are immobilized on an assay surface, such as assay surface 2620 of FIG. 26. Step 4005 may be performed, for example, by the manufacturer of the assay system rather than the assay system user.

Continuing to refer to FIG. 40, assay process 4000 then proceeds to a step 4010, in which a biological sample, such as a serum sample, is reacted with a labeled antigen mix. The labeled antigen mix may be provided by the assay system manufacturer or custom-formulated by the assay system user. The mixed sample is then added to a fluidic sample chamber in a step 4015. Optionally, excess labeled antigen mix may be washed away from assay surface 2620 in an optional step 4018. The fluorescence signal at the assay surface is then imaged by the assay system in a step 4020, and then the captured image may be analyzed in a step 4025.

The assay described with respect to this example may be reduced to a single step assay, in which the only user interaction is the introduction of biological sample to the assay device. In an embodiment, the labeled antigen mix may be immobilized within the fluidic sample chamber using conventional methods such as lyophilization. For example, the labeled antigen mix may be lyophilized along with sugar-based stabilizers at or near an inlet port of the assay system. Upon biological sample introduction, the labeled antigen mix is rehydrated and target antibody-labeled antigen complexes are formed. The complexes may then bind to the appropriate immobilized antigen sites on the assay surface, thereby forming the antigen-antibody-antigen complexes as previously described. A further advantage of this embodiment is that the sensitivity of assay system 2600 may allow elimination of subsequent wash steps. In particular, when using planar waveguide illumination, the evanescent field is localized within a few hundred nanometers of the assay surface for visible light illumination. Consequently, fluorescent dye in the bulk solution of fluidic sample chamber does not contribute to the fluorescence signal measured at detection system 2660. The result is a true single step assay: a biological sample is added to cartridge 2602, which is then imaged on detection system 2660 in step 4080 and subsequently analyzed in step 4025. Alternatively, a final wash step 4018 may potentially yield improved signal-to-background performance in the assay and may therefore be useful in certain assay applications. Several methods for the final wash step may be envisioned. For example, this step may be a simple wash buffer addition introduced by the user from a dropper bottle. Alternatively, the final wash buffer may be stored on-board the device, such as in a blister pack that is either deployed by the user or automatically by activation in the detection system.

We note that the workflow outlined in FIG. 40 is only exemplary. Other embodiments may have different sequences of steps or additional modifications.

Example 10

Labeled Antigen Assay with Serum Samples

Array Printing:
Recombinant antigens associated with human immunodeficiency virus ("HIV") and *Treponema pallidum* (causative organism of syphilis) were printed in duplicate as a geometrically defined array on assay surface 2620 of planar waveguide 2605 using a conventional arraying robot (Bio-Dot). gp 41 and HIV-1 p24 protein were printed for HIV infection analysis, while *Treponema pallidum* proteins p17 and p47 were printed for detection of syphilis antibodies.

Antigen Labeling and Labeled Antigen Mix Formulation:
Aliquots of the antigens printed to the array were covalently labeled with fluorescent dye Alexa-647 and quantitated by UV absorbance. Optimal working concentrations of labeled antigens were determined empirically, and a labeled antigen mix of antigens at two times the working concentration in assay buffer (1×=1× phosphate buffered saline ("PBS")+1% bovine serum albumin ("BSA")+0.05% Tween 20 (Poly(oxyethylene)x-sorbitane-monolaurate, purified for membrane research and available from Roche)) was formulated.

Assay Procedure:

10 microliters of human serum was mixed with 10 microliters of 2× labeled antigen mix in a microcentrifuge tube. The full volume was introduced to a fluidic sample chamber and allowed to incubate for 20 minutes at room temperature. The incubated sample was imaged with imaging device 2650 without any further processing. The signal-to-noise ratio ("SNR") value for the captured fluorescence signal was derived according to the following formula:

$$SNR = \frac{(SN - BK)}{sdBK}, \quad \text{(Eq. 1)}$$

where SN is scaled signal with reader instrument noise removed, BK is scaled signal from negative control sites flanking the feature, and sdBK is standard deviation of the BK signals.

FIG. 41 shows an example of a series of digital images captured using the labeled antigen assay protocol described above. The array as shown was formed of a series of duplicated features, including fluorescently-labeled BSA as fiducial markers (BSA647), antigens associated with HIV (p24 and gp41), antigens associated with *T. pallidum* (p17 and p47), and negative sites composed of print buffer only (Neg). The arrays were incubated with 20 microliters of a 1:1 mixture of labeled antigen mix and a human serum sample for 20 minutes. Three human serum samples were used in the demonstration: 1) Seracare 9148134 is a known positive for antibodies against HIV-1; 2) Seracare BM217820 is a known positive for antibodies against *T. pallidum*; and 3) Sigma H4522 is a pooled human serum sample negative for antibodies against HIV-1 and *T. pallidum*. The resulting fluorescence signal was recorded at imaging device 2650 without a wash step. Custom reaction site-finding algorithms, implemented at computer 2670, define feature locations and record fluorescence intensity as numerical values corresponding to average pixel intensities within defined regions, and SNR values are calculated according to Equation 1. As may be seen in FIG. 41, the appropriate reaction sites indicative of the presence of target antibodies indicative of HIV-1 and syphilis produce fluorescence signal in accordance with the known sample serostatus, thereby confirming the accuracy of the labeled antigen assay in identifying the disease state of the given biological sample.

Example 11

Real Time Signal Acquisition for a Kinetic Analysis

In another embodiment, assay system 2600 may be combined with the labeled antigen assay described herein to generate kinetic assay data rather than the more common end point assay approach. Due to the fact that the detection system is relatively insensitive to fluorescent dye in the bulk solution, assay system 2600 may be used to collect real time data as the labeled antigen-target antibody complexes bind to the immobilized antigens on the assay surface. Real time data collection allows collection of kinetic parameters that offer several potential advantages. For example, initial binding rate information may be used for very rapid assays. Because initial binding rate is directly related to the concentration of target analyte in solution, kinetic assays may potentially provide quantitative data, with initial binding rate linked to bulk solution concentration. For qualitative assays, a biological sample with a large concentration of target analyte will show signal very quickly relative to a negative control. Example kinetic data are provided in FIG. 42 from an experiment described in detail below. In this example, two target analyte concentrations are distinguished from each other and from the negative control within 5 minutes of biological sample addition. The labeled antigen assay allows real time acquisition of signal from the assay surface in the presence of the sample mixture. Therefore, the rate of accumulation of signal on a specific antigen feature may be tracked in real time as a kinetic assay. As an example, a labeled antigen assay was performed as in Example 1, except fluorescence images were acquired at time points over fixed intervals for two biological samples varying in concentration of human serum (50% dilution and 0.58% dilution, respectively), and one biological sample of known negative HIV status (VBMA90015-01) (See FIG. 42). Signal intensity varied in both rate of increase and final intensity as a function of concentration of serum sample, with both the HIV positive samples showing more and faster accumulation of signal than the negative control sample. This result suggests the possibility of a diagnostic assay for analyzing the presence and concentration of targets by the rate of signal acquisition.

Example 12

Rapid Assay Demonstration

Figure 42:
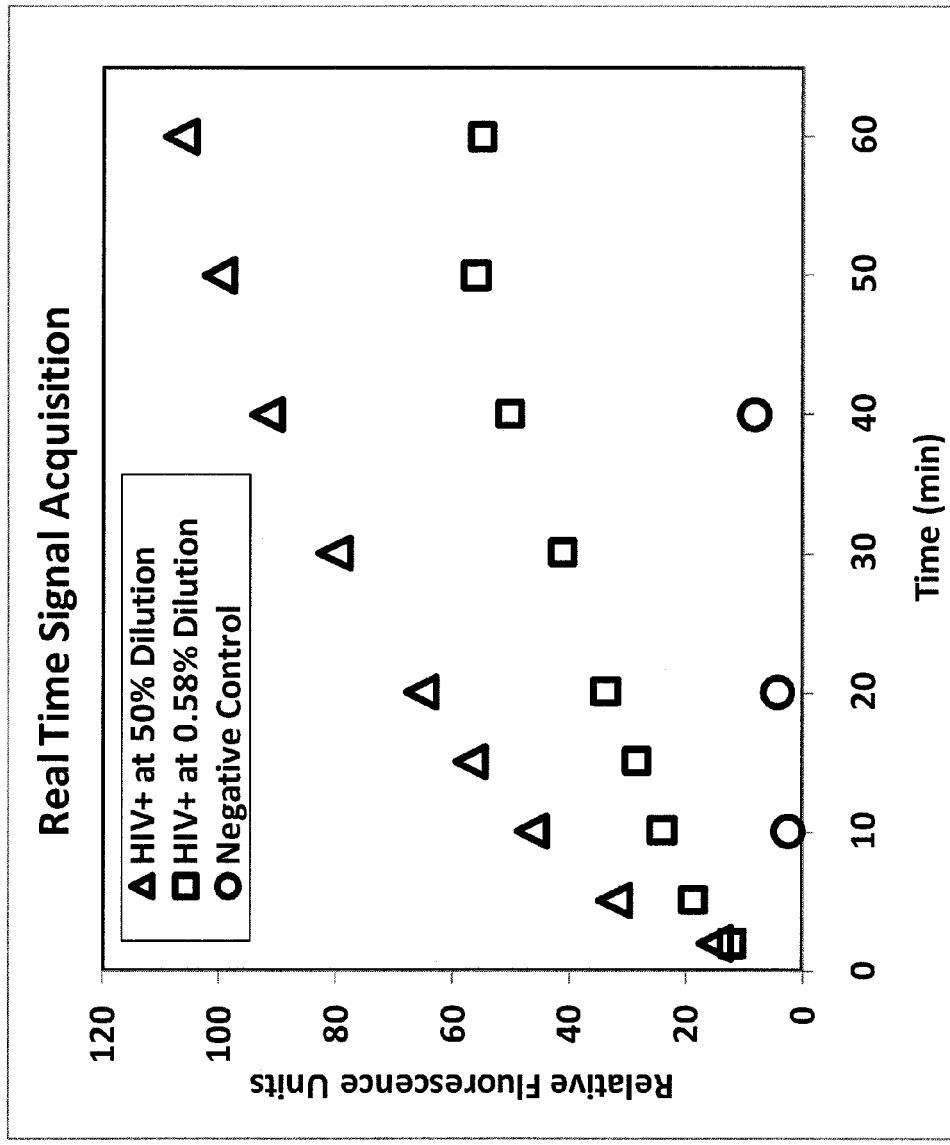
FIG. 42 is a graph showing the results of a real time signal acquisition for a kinetic analysis of an analyte, using the labeled antigen assay with the assay system, in accordance with an embodiment.

The experiment and data in EXAMPLE 11 may also be used as a demonstration of an extremely rapid HIV-1 antibody detection assay. FIG. 42 illustrates the collection of kinetic data. Alternatively, one may define an end point assay at, for example 5 minutes. Reviewing the data shown in FIG. 42, one sees that a high concentration HIV sample, a lower concentration sample, and a negative control are all readily distinguished in terms of quantitative fluorescence output. FIG. 42 is thus a demonstration of a very rapid (i.e., in minutes) HIV-1 antibody detection assay.

Example 13

Labeled Antigen Assay with Whole Blood Results

Figure 43:
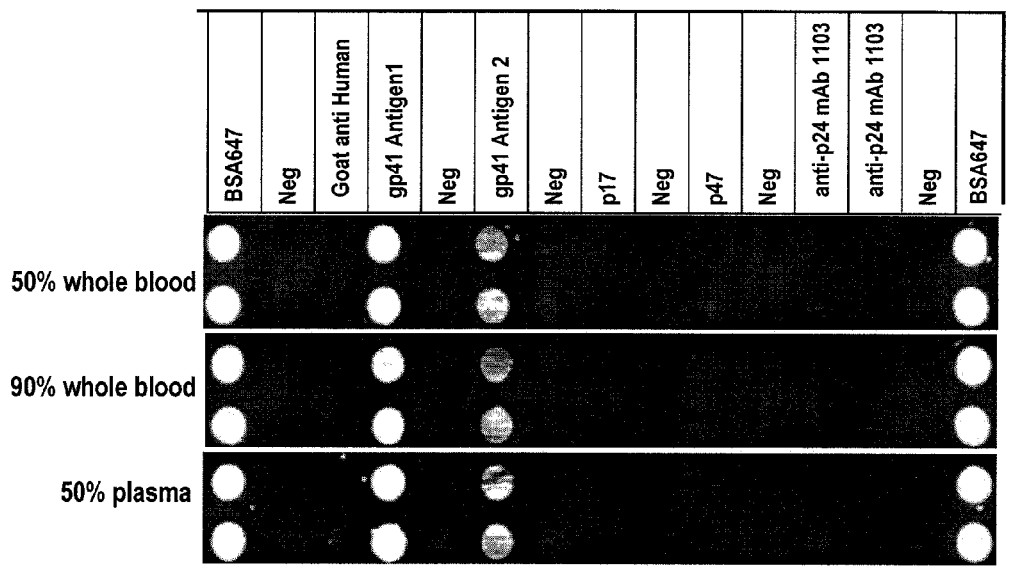
FIGS. 43-44 show an exemplary analysis summary obtained using the assay system and labeled antigen assay process with whole blood or plasma as the biological sample, in accordance with an embodiment.
Figure 44:
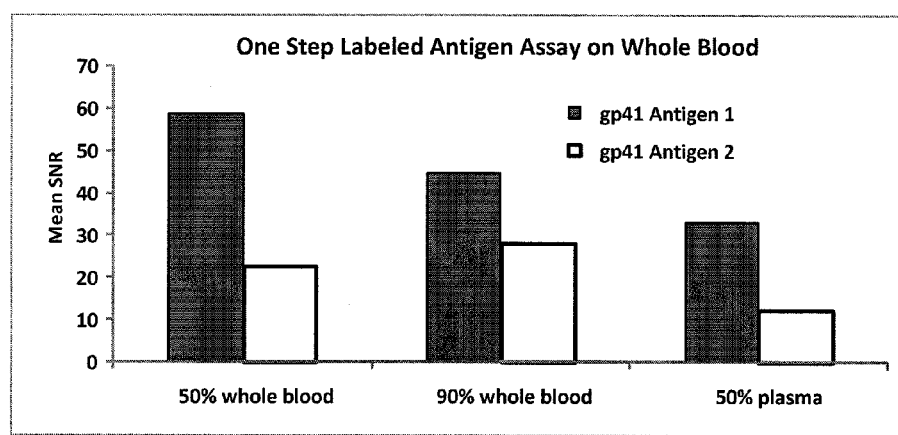

In another embodiment, system 2600 may be combined with the labeled antigen assay described herein to perform assays in complex sample matrices. Because of the evanescent illumination approach, the assay is relatively insensitive to various components encountered in the bulk solution. For example, many immunoassays require serum or plasma specimens, as the cellular components of whole blood may interfere with assay performance. Whole blood assay devices, such as immunochromatographic strip assays, typically require a cell separation membrane upstream from the readout zone, as red blood cells and hemolytic products can interfere with readout on these devices. Example whole blood assay results are provided in FIGS. 43-44 from an experiment described immediately below.

In an embodiment, whole blood is assayed using the labeled antigen assay described above. The ability to analyze whole blood may extend the utility of a point-of-care assay by reducing the need for biological sample preparation and the inherently necessary laboratory infrastructure. For example, a process flow may be envisioned in which whole blood from a fingerstick is applied directly to a labeled antigen assay cartridge, wherein a single addition of assay reagents completes the assay procedure. To demonstrate the feasibility of such a process flow using the labeled antigen assay on the assay system described above, whole blood samples from HIV positive donors were drawn into EDTA blood tubes to inhibit coagulation. A portion of each sample was withdrawn and centrifuged to obtain plasma by removal of red blood cells. Then, the above labeled antigen assay procedures were performed using concentrations of 90% whole blood, 50% whole blood, and 50% plasma. As may be seen from FIGS. 43-44, the signal-to-noise ratio results clearly demonstrate efficacy of the method using either whole blood or plasma. Further, the results were comparable when using 50% or 90% whole blood. Cellular and other components in the whole blood do not appear to interfere with the assay.

In another embodiment, fluidic sample chamber in cartridge 2602 may be specifically designed to improve assay performance by controlling fluid flow rates over the assay surface. Static incubations in small fluidic channels generally have limits of detection set by mass transport limitations (e.g., diffusion) in the system. By engineering fluidic sample chamber geometry (i.e., length, width, height, shape) and surface energies, sample flow rate over the assay surface can be optimized for improved assay performance.

Example 14

HIV Antigen-Antibody Combination Assay

In another embodiment, the disclosed system and method are used to detect both antiviral antibodies and viral antigen(s) in the same sample in a single combination assay. In the context of HIV infection, detection of antibodies against the virus is a well established diagnostic tool. Serological testing, however, only detects infection after the individual has developed an immune response, leaving a "window phase" where viral replication is occurring but no detectable antibodies are present in the host. By adding direct detection of HIV viral antigen such as p24 capsid protein, infection may be detected earlier during the window phase. This so-called antigen-antibody combination assay (sometimes referred to as the $4^{th}$ generation of HIV blood diagnostics assays) may provide more timely and sensitive test results as compared to antibody-only tests.

In this example, p24 antigen is used to illustrate the HIV antigen-antibody combination detection assay in a sandwich immunoassay using two purified monoclonal antibodies (mAbs) to detect the p24 antigen. It is to be understood that polyclonal antibodies can also be used as either capture or detect antibodies. For the purpose of this example, a mAb-mAb pair was used. It is to be understood that other HIV antigens may be used as target proteins. Mouse monoclonal antibodies against HIV-1 p24 antigen were obtained from commercial vendors, such as ImmunoDiagnostics, Inc. (Catalog #1103), Meridian Life science, Inc. (cat #C65690M), Santa Cruz Biotechnology, Inc. (Catalog #sc-57827), United States Biological (Catalog #H6003-33D, H6003-30A, H6003-27J, H6004-72, H6004-73, and H6004-74), Thermo Fisher Scientific, Inc. (Catalog #MA1-83231), PerkinElmer, Inc. (Catalog #NEA-9306001), Maine Biotechnology Services (Catalog #MAB739P), and NIH AIDS Research and Reference Reagents Program (Catalog #3537, 4121, 6457, and 6458). Alternatively, polyclonal anti-p 24 antibodies may be commercially sourced from vendors such as United States Biological (Catalog #H6005 and H6003-27A), Thermo Fisher Scientific, Inc. (Catalog #PA1-85555), and Maine Biotechnology Services (Catalog #PAB7103P).

An appropriate mAb pair was selected based on pairwise screen as commonly performed in sandwich immunoassay development. One mAb was printed to the activated waveguide surface using a robotic arrayer (Bio-Dot, Inc.) and is referred to as the "capture antibody." The second antibody in the pair, also called the "detect antibody," was conjugated to biotin in a standard NHS-ester crosslinking reaction consisting of the antibody and NHS-PEG12-Biotin (Pierce Biotechnology; Rockford, Ill.), then purified by size-exclusion chromatography.

It is to be noted that antibodies against different epitopes of the antigens may be used. In one aspect, antibodies against the same antigen may be combined and tested in all possible permutations in order to identify the best pair with the highest specificity and sensitivity. For example, three different antibodies (Abs) A, B and C may be tested as antibody pairs A-B, B-A, A-C, C-A, B-C, and C-B, with the first antibody being the capture antibody and the second antibody being the detect antibody. Samples with known antigen composition or samples tested using established methods may be used to select the pair having the highest specificity and sensitivity.

In another aspect, either the detect antibody or the capture antibody may contain more than one antibody. In another aspect, the detect antibody is different from the capture antibody. In some cases, the capture antibody and the detect antibody may be interchangeable, or in other words, the capture antibody may be used as the detect antibody while the detect antibody is used as the capture antibody. In other cases, the capture antibody and the detect antibody are unique and are not interchangeable. In another aspect, the detect antibodies shall not significantly bind to the capture antibodies. Typically, the detect antibodies and the capture antibody bind to different epitopes on the antigen. The detect antibody and the capture antibody may be either monoclonal or polyclonal antibodies.

During an infection, the host may produce antibodies against the foreign antigens. Antigen bound to these host antibodies may not be detectable by antibody sandwich assays. These antibody-antigen complexes may be disrupted with heat, low pH (followed by pH neutralization), salt, or combination thereof. These disruption methods may help denature the antibodies which are incapable of re-binding the released antigen. Such disruption process may be referred to as decomplexation.

In this example, the final detect reagent is streptavidin conjugated with a fluorescent dye (SureLight P3, Columbia Biosciences; Columbia, Md.). If p24 antigen is present in the sample, an antibody-antigen-antibody sandwich is created on the waveguide surface. The streptavidin-dye binds to the biotinylated detect antibody and fluorescent signal is detected The HIV antibody detection assay is similar to that described in Example 8. Recombinant proteins representing HIV-1 envelope glycoprotein 41 (gp41) and capsid antigen p24 were printed to the waveguide surface using the Bio-Dot arrayer. The detect reagent was goat anti-human IgG conjugated to the fluorescent dye DyLight649 (KPL, Inc., Gaithersburg, Md.). Control spots in the array included human IgG (detect reagent control) and print buffer spots (non-specific binding control).

Printed waveguide arrays were rinsed and then blocked with a protein-based blocker and then coated with a sugar-based stabilizer. Processed waveguides were then assembled into disposable cartridges described previously.

Human serum control samples certified as negative for HIV, hepatitis C virus and RPR (syphilis) were sourced commercially (Valley Biomedical, Winchester, Va.). Serum samples from HIV-positive individuals were from a sample archive at the Antiviral Research Center, San Diego, Calif., provided under an Institutional Review Board approved protocol. Three categories of HIV positive samples were provided: (1) RNA positive, antibody negative samples (acute, or window-phase samples. These samples have been tested negative for HIV-1/2 antibody by Enzyme Immunoassay (EIA); EIA is considered the most sensitive screening test in this protocol and Western Blots were not run once the negative EIA results was generated); (2) Western Blot indeterminate samples; and (3) weak positive Western Blot samples. The HIV-positive collection therefore represents individuals in the early stages of HIV infection.

Samples were assayed on the cartridges at ambient temperature (about 20 to 25° C.). The p24 antigen detection cartridge array contained spatially-arrayed anti-p24 antibody, printed print buffer blanks, and fluorescently-labeled BSA positioning marker features. At the completion of the assay procedure, the cartridges were inserted into the reader instrument for fluorescence imaging. This workflow allows batch processing of the disposable sample cartridges.

Detection of HIV antigen was performed using the following protocol. A 19-microliter aliquot of serum was combined with an 8-microliter volume biotin-labeled detection antibody in sample dilution buffer (PBS, 0.1% Tween-20, non-specific binding blocking reagents) and mixed by aspiration. Immunoassay blocking buffer components may include bovine serum albumin (BSA), polymerized BSA, fetal calf serum or normal serum from other animal species, non-fat dry milk or casein, alkaline-hydrolyzed casein, acid-hydrolyzed casein, fish gelatin, polyethylene glycol (PEG), polyvinyl alcohol (PVA), polyvinylpyrrolidone (PVP), thiol-reactive compounds such as glutathione and L-cysteine, and immunoglobulins, including IgG from specific animal sources (e.g., mouse IgG), polymerized IgG, and species-specific fragments of IgG [Fc, Fab, F(ab')2], to block nonspecific binding. Immunoassay blocking buffer may also contain non-ionic detergents such as Tween-20 and Triton X-100. 25 microliters of this diluted sample mixture was loaded into the cartridge input port by transfer pipette. The applied sample passively flowed through the cartridge, covering the printed array. Static incubation was for 20 minutes without user intervention. Following the sample incubation period, a 100-microliter volume of 8 nanomolar streptavidin-SureLight P3 in conjugate dilution buffer (PBS, 0.2% Tween-20, non-specific binding blocking reagents) was added to the cartridge input port and allowed to passively flow through the cartridge. Following a 20-minute incubation with streptavidin-SureLight P3, two 150-microliter volumes of wash buffer (PBS, 0.2% Tween-20, non-specific binding blocking reagents including 10 mg/ml bovine serum albumin (Roche; as above) and 0.5% v/v fetal bovine serum (Atlas Biologicals, Fort Collins, Colo.)) were serially added to the input port, and each wash was allowed to flow through the cartridge for 5 to 6 minutes. The cartridge was then inserted into the reader instrument for fluorescence data collection. Read time and data processing in the instrument is approximately 30 seconds per cartridge. After results acquisition, the cartridge was removed from the reader instrument and disposed as biohazard waste.

Detection of anti-HIV antibody was performed using the following protocol. A 6 microliter aliquot of serum or plasma was diluted in 194 microliters of sample dilution buffer (PBS, 0.5% casein, 0.05% Tween-20). 175 microliters of this diluted sample mixture was then loaded into the cartridge input port by transfer pipette and were allowed to flow passively through the cartridge during a 15-minute incubation period without user intervention. 175 microliters of wash buffer (PBS, 0.1% Tween-20) was then added to the input port and allowed to flow through the cartridge for 3 minutes, followed by the addition of 175 microliters of dye-conjugated anti-human IgG in a second diluent (PBS, 1 mg/ml BSA, 0.05% Tween-20) and allowed to incubate for 10 minutes. The cartridge was then inserted into the reader instrument for fluorescence data collection. Read time and data processing in the instrument was approximately 30 seconds per cartridge. After acquisition of the results, the cartridge was removed from the reader instrument and disposed as biohazard waste.

FIG. 50 shows the results of the HIV-1 p24 antigen and antibody combination assays. Antigen and antibody reactivities were recorded as normalized fluorescence signal intensity after background signal had been subtracted. Background signal was the average of the signal on printed buffer blank spots (negative reference spots) located adjacent to the printed antibody or antigen spot of interest. For the HIV-1 p24 antigen assay, the intensity of the printed fluorescently-labeled BSA positioning spot signals was utilized for normalization; for the HIV-1 antibody assay arrays, the intensity of the printed human IgG spot signal was used for normalization. For both assay formats, spot intensity cutoff values ("co") are based on the mean on-spot signal generated from a panel of HIV-negative samples. For this example, cutoff for a given printed spot was defined as the mean intensity plus three standard deviations for the collection of negatives. Antigen detection data are presented in FIG. 50 as sample signal to cutoff ratios ("s/co"). Antibody detection data are reported as "positive" for s/co>1.15, "indeterminate" for $1.15 \geq s/co \geq 0.85$, and "negative" for s/co<0.85.

As shown in FIG. 50, two of five window-phase sera (RNA-positive, antibody-negative) had detectable p24 antigen in this assay (See results for Sample IDs 3 and 4). These HIV antigen positive samples would not be detected with an antibody-only test. None of the Western Blot indeterminate or weak positive samples gave p24 antigen signal above the cutoff threshold. Of particular note, however, are samples 9 and 13. These are negative in the MBio antibody assay, but show S/CO at 0.6 on the MBio p24 antigen assay. We believe this antigen signal is real, and that these early seroconversion samples have detectable p24 antigen. Further optimization of the cutoffs for the antigen assay will possibly result in these samples achieving positive status on the p24 antigen assay. The lack of p24 antigen signal in most of the antibody-positive samples is expected. As a person generates antibodies against the virus, circulating p24 antigen becomes bound in antigen-antibody complex. In the absence of decomplexation through heat or chemical treatment, which results in denaturation of antibodies and release of their bound antigens, complexed p24 antigen may not be detected in a sandwich immunoassay like that described here. Because the current p24 antigen assay in this example does not involve decomplexation, p24 antigen may not be detectable when it is bound by anti-p24 antibody present in the sample. The decomplexation methods described above may be applied to expose the antigen and make it detectable by the disclosed assays.

Of the 10 HIV-1 positive samples with indeterminate Western Blot results, the HIV-1 antibody assay gave five positive, two indeterminate, and three negative results. All of these samples are "true positive" for HIV infection as defined by the presence of viral RNA. These results suggest that the antibody assay disclosed herein has superior sensitivity relative to the Western Blot reference method. Of the 10 HIV-1 positive samples with weak positive Western Blot results, the HIV-1 assay of the present embodiment was positive for all 10.

In summary, the combined HIV-1 antigen/antibody assay demonstrated here has superior sensitivity to the Western Blot reference method. This includes detection of some samples in the pre-seroconversion window phase. We note that in this example, each sample was run in two separate cartridge channels, one for antigen and one for antibody. By combining the sandwich assay approach demonstrated in Examples 9 and 10 with the sandwich immunoassay described in this Example, a single fluidic channel, antigen/antibody combination assay may also be performed. It is to be noted that the antigen-antibody assay may also be modified to detect infections by other agents, for example, HCV and syphilis, among others.

Additional Embodiments

Figure 45:
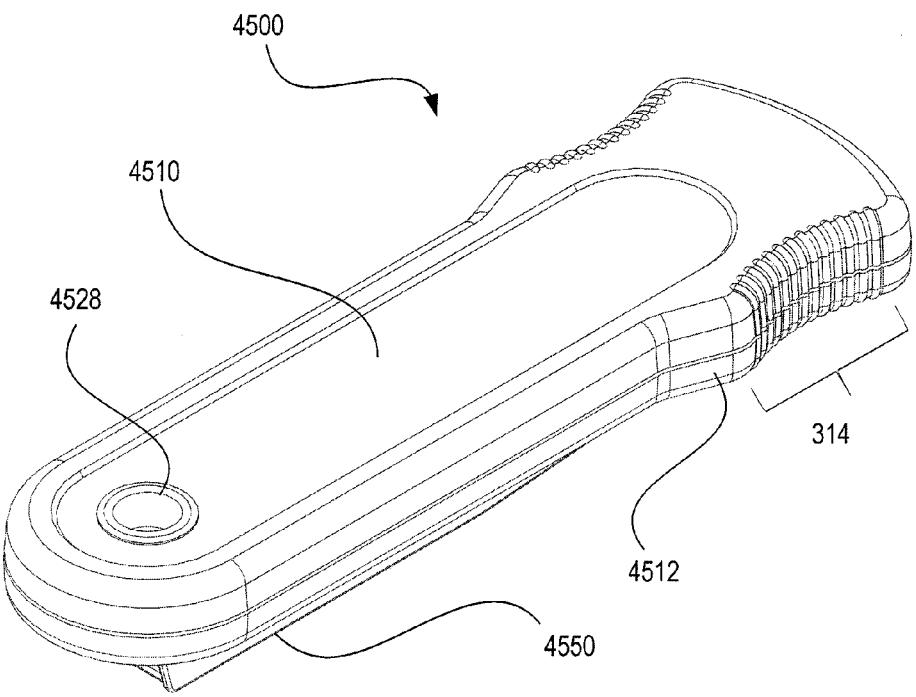
FIGS. 45-46 show a cartridge with integrated tilt mechanisms, in accordance with an embodiment.
Figure 46:
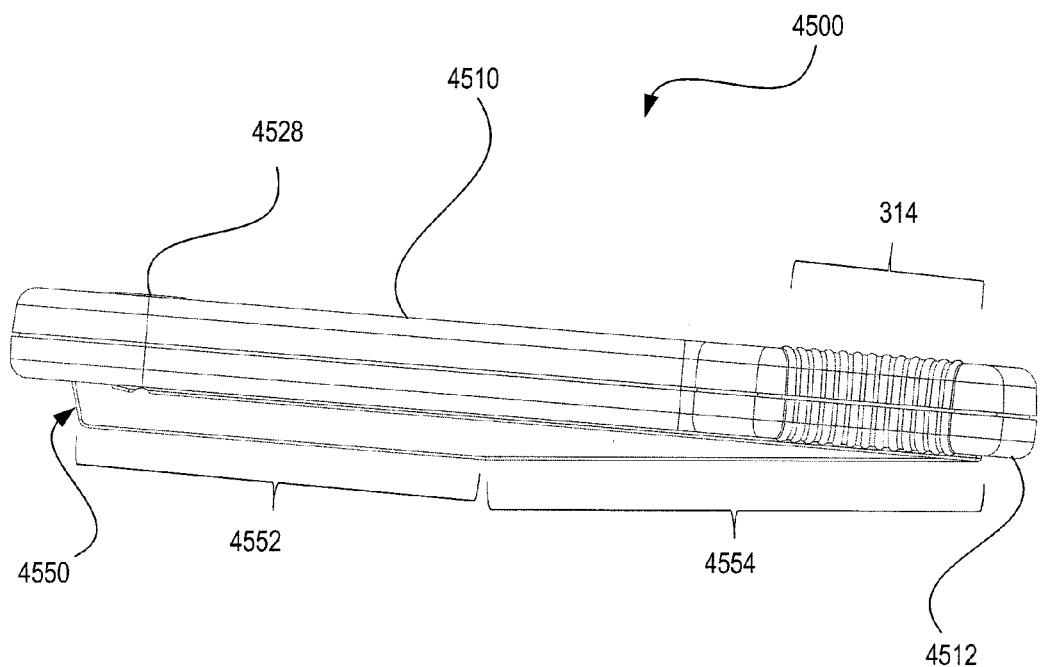

In certain applications, such as when more than one addition of a fluid into the assay cartridge is required, it may be advantageous to place the assay cartridge at a tilt so as to assist with the fluid flow, such as discussed in previously-mentioned U.S. Provisional Patent Application Ser. No. 61/391,911. FIGS. 45 and 46 show a perspective view and a side view of a cartridge 4500, which is a slight modification of cartridge 300 of FIGS. 3-11. Cartridge 4500 includes an upper piece 4510 and a lower piece 4512. Upper piece 4510 includes an inlet port 4528, which is located at a distal end from textured grooves 344, in contrast to cartridge 300. Lower piece 4512 additionally includes fin features 4550. As better visible in FIG. 46, fin features 4550 includes a first portion 4552 and a second portion 4554. First and second portions 4552 and 4554, respectively, are configured such that, when cartridge 4500 is resting on first portion 4552, then flow plate 324 (not visible) inside cartridge 4500 lies parallel to the resting surface (i.e., flat). When cartridge 4500 is resting on second portion 4554, then flow plate 324 within cartridge 4500 lies at a 5-degree angle with respect to the resting surface such that inlet port 4528 is slightly elevated with respect to the outlet port of the flow plate (not visible). The angle of induced tilt may be any angle appropriate for optimum flow of the particular liquids being used in the assay. Optionally, the position of the inlet port and the direction of the tilt may be reversed, i.e., the inlet port may be located near textured grooves 344, and the cartridge may be tilted such that the end with the textured grooves rests higher than a distal end away from the textured grooves.

Figure 47:
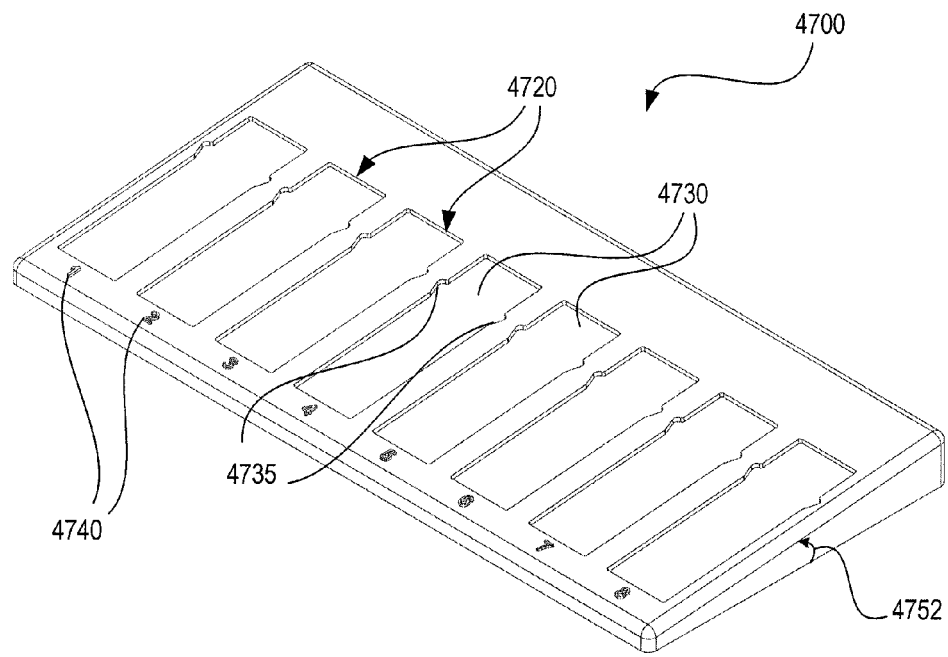
FIG. 47 shows a rack for enabling batch processing and cartridge tilt for assay cartridges, in accordance with an embodiment.
Figure 48:
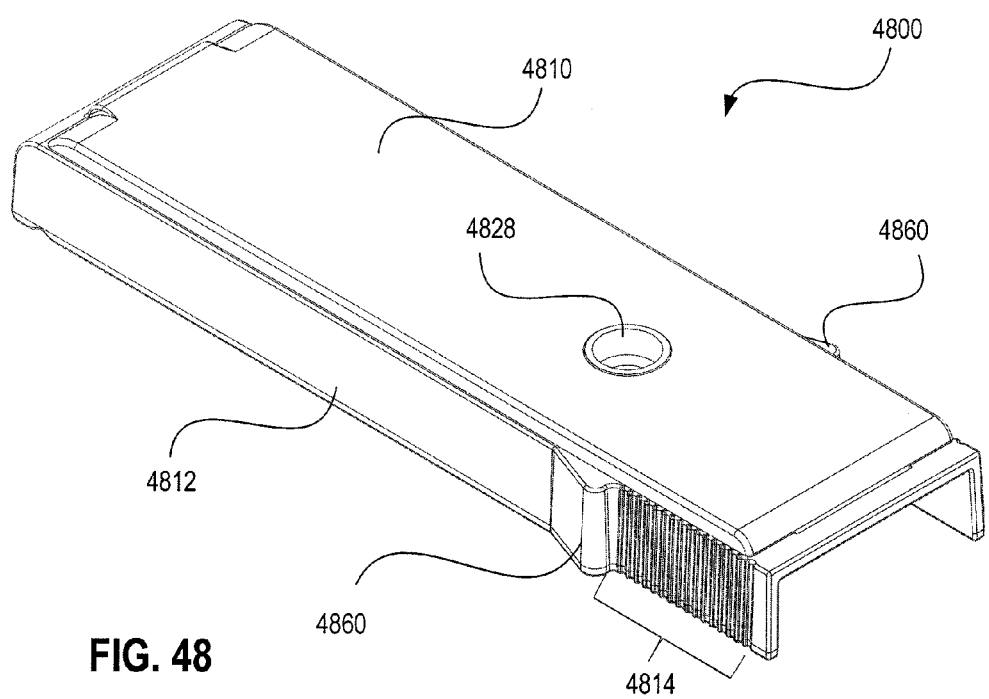
FIG. 48 shows a cartridge suitable for use with the rack of FIG. 47, in accordance with an embodiment.
Figure 49:
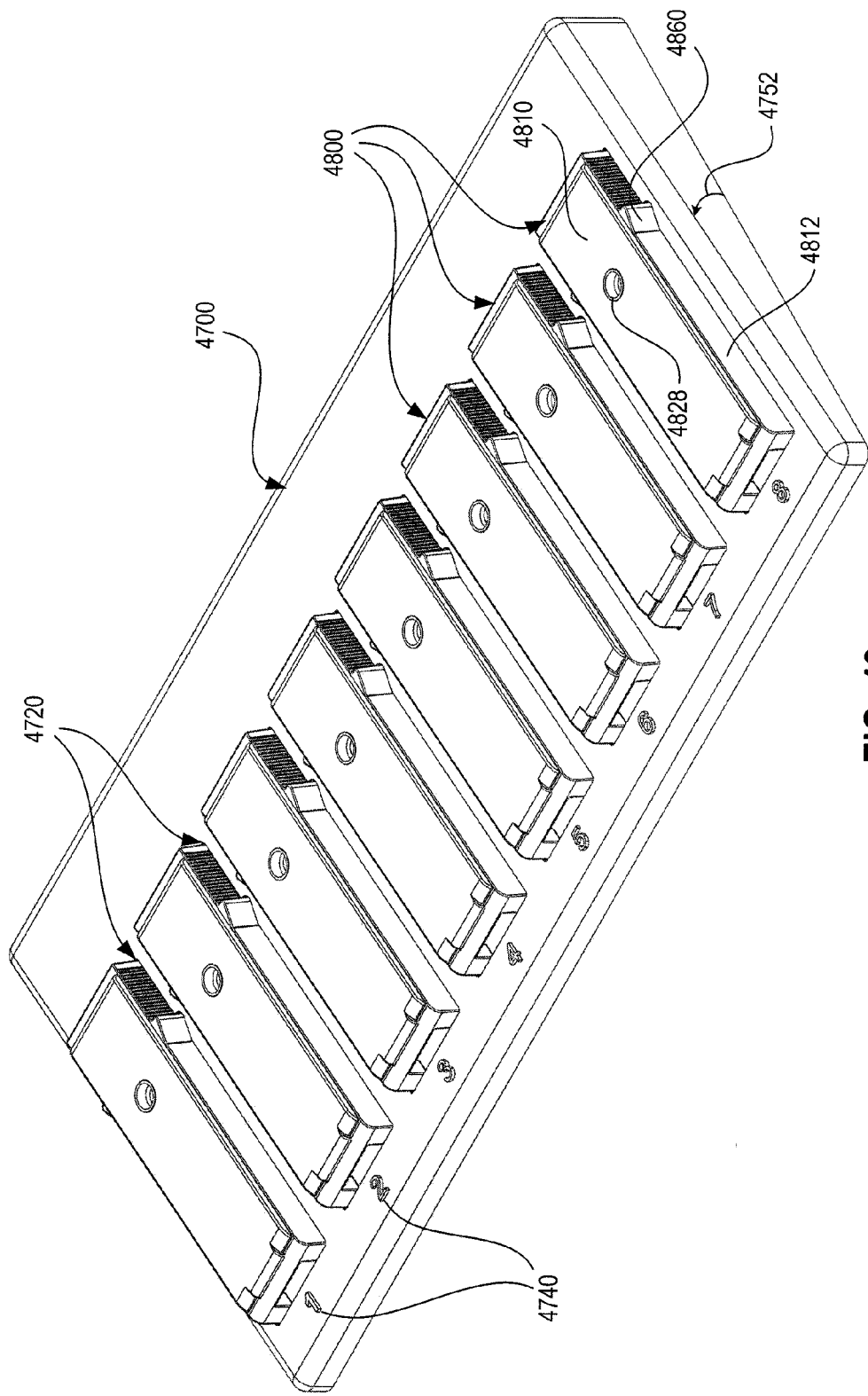
FIG. 49 shows the tilt rack of FIG. 47 filled with cartridges of FIG. 48, in accordance with an embodiment.

In another embodiment, the reader instrument and cartridges may be accompanied by a rack. The purpose of the rack may be to help organize operator workspace. In another embodiment, the rack may be designed such that the cartridges, when placed on the rack, lies at a tilt in order to facilitate fluid flow through the cartridges. FIGS. 47-49 illustrate a tilt rack and cartridge system for facilitating batch processing of cartridges as well as the placement of the cartridges at a specified tilt angle.

FIG. 47 shows a tilt rack 4700, including a plurality of slots 4720 into which cartridges may be placed. Each one of slots 4720 includes an indentation 4730 and notches 4735 configured for unidirectional placement of a compatible cartridge. Tilt rack 4700 may optionally include numbers 4740 for identifying slots 4720. One side of tilt rack 4700 is designed to be higher than an opposing end such that the top surface of tilt rack 4700 is at an angle 4752 with respect to the surface on which the tilt rack rests. Angle 4752 may be, for example, 5 degrees or any suitable angle to optimize the fluid flow for the particular assay being run. Tilt rack 4700 may be, for example, molded out of a plastic or metal material, which may be readily cleaned with conventional detergents and cleaners.

FIG. 48 shows a cartridge 4800 which is configured to be compatible with tilt rack 4700. Cartridge 4800 includes an upper piece 4810 and a lower piece 4812 with textured grooves 4814 to facilitate gripping. Although not visible in the figure, a waveguide and a mechanism for defining a fluidic channel, such as a gasket, are housed within cartridge 4800, in accordance with an embodiment. An input port 4828 provides sample access to the fluidic channel defined within cartridge 4800. Cartridge 4800 is sized and shaped so as to fit into one of slots 4720 of tilt rack 4710, with protrusions 4860 on cartridge 4800 being designed to engage with notches 4735 of tilt rack 4700. FIG. 49 shows an example of rack 4700 filled with eight cartridges 4800.

In another embodiment, the rack may include one or more integrated timers (e.g., stopwatches) for user convenience. In another embodiment the rack may have buttons or other user interface means use for initiating timed steps. In another embodiment, the rack may have indicating means such as lights or alarms that provide feedback to the user. For example, insertion of a cartridge into the rack may initialize an internal timer. Upon completion of a pre-determined amount of time, a light may illuminate (or go out) and/or an audible chime may indicate to the user that a step has been completed. Multiple lights or indicating means could be used to stage multiple steps. In another embodiment, the rack may physically actuate features of the cartridge. For example, a physical actuator in the rack may deploy an on-cartridge reagent contained in a pre-loaded blister pack.

We note that the above embodiments are described in terms of labeled antigen assays. The sandwich assay concept described here, however, is not restricted only to labeled antigen assays. The sandwich assay approach and detection system described herein may be used, for example, with nucleic acid (e.g., DNA, RNA) based assays and cell-based assays.

The assay system described above may be provided in a kit. For example, a functional kit may include a reader instrument, one or more cartridges, a tilt rack, one or more sample mixing tubes, sample diluent solution, wash solution and fluorescent conjugate solution (such as anti-human IgG labeled with an appropriate dye, such as Dylight647 or Alexa649). The cartridges may be sealed in individual pouches for protection during shipping and storage. The reader instrument in the kit may include an on-board computer for instrument control and image analysis or, alternatively, provided with software and/or an external computer loaded with software for controlling the reader instrument and image analysis. An adjustable pipette may also be provided as a part of the kit, or may be supplied by the end user.

A variety of embodiments of the present system are contemplated including, but not limited to, the following:

1. A device for analyzing a sample potentially containing an analyte, the device including: a) a planar waveguide; b) a refractive volume for optically coupling light provided by a light source to the planar waveguide; and c) a plurality of capture molecules, wherein the planar waveguide and the refractive volume are integrally formed as a single piece, and wherein the planar waveguide includes a first surface and a second surface that is opposite from the first surface, wherein the plurality of capture molecules is immobilized to the first surface.

2. The device of item 1, wherein the plurality of capture molecules include at least one molecule selected from the group consisting of a peptide, a polypeptide, a protein, an antibody, an antigen, a polysaccharide, sugar, an oligonucleotide, a polynucleotide, a synthetic molecule, an inorganic molecule, an organic molecule, and combinations thereof.

3. The device of item 1 or 2, wherein at least one of the plurality of capture molecules is capable of specifically binding the at least one analyte in the sample.

4. The device of item 1, 2 or 3, wherein the planar waveguide is made of an optically transparent plastic material.

5. The device of item 4, wherein the optically transparent plastic material is a material selected from the group consisting of cyclic olefin polymer, cyclic olefin copolymer, polyolefin, polystyrene, acrylic, polymethylmethacrylate, and polycarbonate.

6. The device of item 1, 2, 3 or 4, wherein at least a portion of the first surface of the planar waveguide is modified to provide improved attachment of the capture molecules to the first surface compared to had the first surface not been modified.

7. The device of item 1, 2, 3, 4 or 5, wherein at least a portion of the first surface of the planar waveguide is modified to provide a static water contact angle of between 60 and 75 degrees.

8. The device of item 7, wherein the first surface of the planar waveguide is modified using a process selected from the group consisting of plasma activation, chemical vapor deposition, liquid phase deposition, and surface polymerization of an activation chemistry, and combinations thereof.

9. The device of item 8, wherein the planar waveguide modification is performed using a chemical selected from the group consisting of organosilane, alkoxysilane, chlorosilane, alkylsilane, epoxy silane, glycidoxy silane, aldehyde silane, aminosilane and combinations thereof.

10. The device of item 1, 2, 3, 4, 5, 6 or 7, wherein at least a portion of the first surface of the planar waveguide is covered with a coating, the coating including at least one molecule selected from the group consisting of a polymethacryloyl polymer, a polyethylene glycol polymer, a polycationic polymer, an avidin, a biotin and combinations thereof.

11. The device of item 1, 2, 3, 4, 5, 6, 7 or 10, wherein at least a portion of the first surface of the planar waveguide is covered with a coating for inhibiting nonspecific binding between the first surface of the planar waveguide and the at least one analyte.

12. The device of item 1, 2, 3, 4, 5, 6, 7, 10, or 11, wherein the first surface of the planar waveguide includes an array including at least two reaction sites, each of the at least two reaction sites being formed by printing a composition onto the first surface, the composition including at least one capture molecule.

13. The device of item 12, wherein the array further includes at least one negative control site, the at least one negative control site being formed by printing onto the first surface a composition containing no molecule that detectably binds to the at least one analyte in the sample.

14. The device of item 13, wherein the at least one negative control site is located at a proximal end of the array closest to an inlet port, at which the sample is introduced onto the first surface.

15. The device of item 13, wherein the array further includes at least one positive control site, the at least one positive control site being formed by printing onto the first surface a composition containing a molecule that consistently binds to the at least one analyte in the sample.

16. The device of item 13, wherein at least one of the positive control sites is located at a distal end of the array farthest from an inlet port, at which the sample is introduced onto the first surface.

17. The device of item 13, wherein the first surface of the planar waveguide further includes a reference site for calibrating one of item intensity and uniformity of the light source.

18. The device of item 17, wherein the reference site includes an excitable molecule immobilized on a portion of the first surface of the planar waveguide.

19. The device of item 18, wherein the excitable molecule is a fluorophore selected from the group consisting of organic dye, lanthanide chelate, semiconductor nanoparticles, and phosphorescent material.

20. The device of item 13, further including a fluidic channel to allow the sample be in contact with the array.

21. The device of item 1, 2, 3, 4, 5, 6, 7, 10, 11 or 12, wherein the plurality of capture molecules is selected from a group consisting of polypeptides, antigens and antibodies.

22. The device of item 21, wherein the array includes a first reaction site and a second reaction site, the first and second reaction sites containing a different capture molecule selected from the group.

23. The device of item 21, wherein the array includes a first reaction site and a second reaction site, the first reaction site including at least a fragment of gp41 antigen of HIV-1, and the second reaction site including at least a fragment of p24 antigen of HIV-1.

24. The device of item 23, wherein the array further includes a third reaction site and a fourth reaction site, the third reaction site including at least a fragment of p47 of *Treponema pallidum*, and the fourth reaction site including at least a fragment of p17 of *Treponema pallidum*.

25. The device of item 24, wherein the array further includes a fifth reaction site and a sixth reaction site, the fifth reaction site including at least a fragment of hepatitis C virus (HCV) core antigen, and the sixth reaction site including an HCV antigen selected from the group consisting of HCV NS3, HCV NS4, HCV NS5, fragments thereof, and combinations thereof.

26. The device of item 21, wherein the array also includes antibodies against the p24 antigen of HIV.

27. The device of item 21, wherein the array includes one or more reaction sites, wherein said reaction sites include capture molecules selected from the group consisting of HIV antigens p17, p24, p31, gp41, p51, p55, p66, gp120, gp160, p41 Type O, and p36 of HIV-2.

28. The device of item 27, wherein the array includes antibodies against the p24 antigen of HIV.

29. The device of item 1, 2, 3, 4, 5, 6, 7, 10, 11, 12 or 21, wherein said sample is whole blood, plasma, or serum.

30. A device for analyzing a sample potentially including at least one analyte, the device including: a) a planar waveguide; b) a refractive volume for optically coupling light provided by a light source to the planar waveguide; and c) a plurality of capture molecules, wherein the planar waveguide and the refractive volume are integrally formed as a single piece, and wherein the planar waveguide including a first surface and a second surface that is opposite from the first surface, the plurality of capture molecules being immobilized to the first surface, the first surface including an array, the array including a first reaction site and a second reaction site, the first reaction site including at least a fragment of gp41 antigen of HIV-1, and the second reaction site including at least a fragment of p24 antigen of HIV-1.

31. A device for analyzing a sample potentially including at least one analyte, the device including: a) a planar waveguide; b) a refractive volume for optically coupling light provided by a light source to the planar waveguide; and c) a plurality of capture molecules, wherein the planar waveguide and the refractive volume are integrally formed as a single piece, and wherein the planar waveguide including a first surface and a second surface that is opposite from the first surface, the plurality of capture molecules being immobilized to the first surface, the first surface including an array, the array including a first reaction site and a second reaction site, the first reaction site including at least a fragment of p47 of *Treponema pallidum*, and the second reaction site including at least a fragment of p17 of *Treponema pallidum*.

32. A device for analyzing a sample potentially including at least one analyte, the device including: a) a planar waveguide; b) a refractive volume for optically coupling light provided by a light source to the planar waveguide; and c) a plurality of capture molecules, wherein the planar waveguide and the refractive volume are integrally formed as a single piece, and wherein the planar waveguide including a first surface and a second surface that is opposite from the first surface, the plurality of capture molecules being immobilized to the first surface, the first surface including an array, the array including a first reaction site and a second reaction site, the first reaction site including at least a fragment of hepatitis C virus (HCV) core antigen, and the second reaction site including an HCV antigen selected from the group consisting of HCV NS3, HCV NS4, HCV NS5, fragments thereof, and combination thereof.

33. A device for analyzing a sample potentially including at least one analyte, the device including: a) a planar waveguide; b) a refractive volume configured for optically coupling light provided by a light source to the planar waveguide, and c) a plurality of capture molecules, wherein the planar waveguide and the refractive volume are integrally formed as a single piece, the planar waveguide including a first surface, and a second surface that is opposite from the first surface, the plurality of capture molecules being immobilized to the first surface, the first surface including an array of at least two reaction sites, and wherein a volume of the sample needed for full contact with all reaction sites on the array is less than 30 microliters.

34. A method for analyzing a sample potentially including at least one analyte, the method including: a) adding at least a portion of the sample to a device, the device including a planar waveguide, a light source, a refractive volume configured for optically coupling light provided by the light source to the planar waveguide, and a plurality of capture molecules, the planar waveguide and the refractive volume being integrally formed as a single piece, the planar waveguide including a first surface and a second surface that is opposite from the first surface, the plurality of capture molecules being immobilized to the first surface; b) allowing the sample to incubate with the plurality of capture molecules on the first surface; c) adding a detection reagent to the device, the detection reagent having been labeled with an excitable tag; and d) allowing the detection reagent to incubate with the first surface.

35. The method of item 34, further including detecting light signal emitted by the excitable tag.

36. The method of item 34 or 35, wherein the detection reagent is selected from the group consisting of anti-human IgG antibody and anti-human IgM antibody.

37. The method of item 34, 35 or 36, wherein the excitable tag is a fluorophore.

38. The method of item 34, 35, 36 or 37, wherein the amount of the sample added to the device is less than 30 microliters.

39. A reader instrument for detection of analyte contained in a cartridge, the cartridge including a waveguide for directing illumination to an assay region thereon, the reader instrument including: a) a housing having at least one aperture for accommodating at least a portion of the cartridge; b) an illumination module attached to the housing, the illumination module being configured for providing illumination; c) imaging optics positioned between the illumination module and the cartridge, when the cartridge is inserted into the housing, the imaging optics being configured for shaping and redirecting the illumination toward the cartridge; and d) an image sensor system held within the housing, the image sensor system being immovably fixed with respect to the illumination module, and the image sensor system further having a field of view that substantially covers the assay region.

40. The reader instrument of item 39, wherein the cartridge extends partially out of the housing in an operating position.

41. The reader instrument of item 39 or 40, further including a door for blocking illumination potentially leaking out of the housing.

42. The reader instrument of item 39, 40 or 41, further including light baffle elements on and around the cartridge for blocking illumination leakage during operation of the reader instrument.

43. The reader instrument of item 39, 40, 41 or 42, wherein the illumination module is not activatable unless the cartridge is correctly inserted into the housing.

44. The reader instrument of item 39, 40, 41, 42 or 43, wherein the imaging optics includes a beam homogenizer.

45. The reader instrument of item 39, 40, 41, 42, 43 or 44, wherein the waveguide includes a refractive volume integrally formed from the waveguide for directing the illumination to the assay region.

46. The reader instrument of item 39, 40, 41, 42, 43, 44 or 45, wherein the image sensor is disposed perpendicular to the planar waveguide.

47. The reader instrument of item 39, 40, 41, 42, 43, 44, 45 or 46, wherein the image sensor is configured for reading supplemental information disposed on the cartridge.

48. A system for performing a biochemical assay on a sample, the system including: A) a cartridge including a planar waveguide having a plurality of capture molecules bound to a planar surface thereof, a refractive volume for optically coupling a light beam provided by a light source to the planar waveguide, the refractive volume being integrally formed from the planar waveguide, and a sample chamber for receiving and containing the sample such that the sample comes into contact with the plurality of capture molecules; and B) a reader instrument including a receiving mechanism for positioning the cartridge therein, the light source for providing the light beam, a detector for detecting a light signal from a portion of the planar surface on which the plurality of capture molecules is bound, and an analysis module for receiving and analyzing the light signal from the detector; wherein the light beam is incident on the refractive volume in a plane parallel to and offset from the planar waveguide, and wherein the refractive volume is configured for refracting the light beam such that the light beam is focused at the planar surface at a nonzero, internal propagation angle relative to the planar surface for all light within the light beam.

49. The system of item 48, wherein the plurality of capture molecules include at least one molecule selected from the group consisting of a peptide, a polypeptide, a protein, an antibody, an antigen, a polysaccharide, sugar, an oligonucleotide, a polynucleotide, a synthetic molecule, an inorganic molecule, an organic molecule, and combinations thereof.

50. The system of item 48 or 49, wherein the planar waveguide is formed of an optically transparent material selected from the group consisting of cyclic olefin polymer, cyclic olefin copolymer, polyolefin, polystyrene, acrylic, polymethylmethacrylate, and polycarbonate.

51. The system of item 48, 49 or 50, wherein the planar surface is modified using a process selected from the group consisting of plasma activation, chemical vapor deposition, liquid phase deposition, and surface polymerization of an activation chemistry, and combinations thereof.

52. The system of item 48, 49, 50 or 51, the sample containing antibodies and viral antigen, wherein the cartridge and the reader instrument are configured to cooperate so as to detect both antibodies and viral antigen in the sample.

53. The system of item 48, 49, 50, 51 or 52, wherein the plurality of capture molecules are arranged as an array including at least two reaction sites, each of the at least two reaction sites being formed by printing a composition onto the planar surface, the composition including at least one of the capture molecules.

54. The system of item 53, wherein the at least two reaction sites containing different compositions.

55. The system of item 53 or 54, wherein the at least two reaction sites include capture molecules selected from the group consisting of HIV antigens p17, p24, p31, gp41, p51, p55, p66, gp120, gp160, p41 Type O, p36 of HIV-2, antibodies against HIV antigen p24, and combinations thereof.

56. The system of item 48, 49, 50, 51, 52 or 53, the reader instrument further including a beam homogenizer.

57. A method for performing a biochemical assay on a sample, the method including: A) providing a cartridge, which cartridge includes a planar waveguide having a plurality of capture molecules bound to a planar surface thereof, a refractive volume for optically coupling a light beam provided by a light source to the planar waveguide, the refractive volume being integrally formed from the planar waveguide, and a sample chamber for receiving and containing the sample such that the sample comes into contact with the plurality of capture molecules; B) introducing the sample into the sample chamber of the cartridge; C) providing a reader instrument, which reader instrument includes a receiving mechanism for positioning the cartridge therein, the light source for providing the light beam, a detector for detecting a light signal from a portion of the planar surface on which the plurality of capture molecules is bound, and an analysis module for receiving and analyzing the light signal from the detector; D) inserting the cartridge, containing the sample, into the reader instrument; E) using the light source, illuminating a portion of the planar waveguide at which the plurality of capture molecules are bound such that, if the sample includes a target analyte, the target analyte interacts with the plurality of capture molecules so as to produce a light signal; F) capturing the light signal; and G) analyzing the light signal; wherein illuminating includes directing the light beam at the refractive volume such that the light beam is incident on the refractive volume in a plane parallel to and offset from the planar waveguide, and refracting the light beam such that the light beam is focused at the planar surface at a non-zero, internal propagation angle relative to the planar surface for all light within the light beam.

58. The method of item 57, wherein the plurality of capture molecules include at least one molecule selected from the group consisting of a peptide, a polypeptide, a protein, an antibody, an antigen, a polysaccharide, sugar, an oligonucleotide, a polynucleotide, a synthetic molecule, an inorganic molecule, an organic molecule, and combinations thereof.

59. The method of item 57 or 58, further including modifying the planar surface using a process selected from the group consisting of plasma activation, chemical vapor deposition, liquid phase deposition, and surface polymerization of an activation chemistry, and combinations thereof.

60. The method of item 57, 58 or 59, the sample containing antibodies and viral antigen, the method further including detecting both antibodies and viral antigen in the sample.

61. The method of item 60, wherein the plurality of capture molecules are selected from the group consisting of HIV antigens p17, p24, p31, gp41, p51, p55, p66, gp120, gp160, p41 Type O, p36 of HIV-2, antibodies against HIV antigen p24, and combinations thereof.

62. The method of item 57, 58, 59 or 60, wherein providing the reader instrument further including homogenizing the light beam before the light beam is optically coupled to the planar waveguide.

63. A kit for performing a biochemical assay on a sample, the kit including: A) a cartridge including a planar waveguide having a plurality of capture molecules bound to a planar surface thereof, a refractive volume for optically coupling a light beam provided by a light source to the planar waveguide, the refractive volume being integrally formed from the planar waveguide, and a sample chamber for receiving and containing the sample such that the sample comes into contact with the plurality of capture molecules; B) a reader instrument including a receiving mechanism for positioning the cartridge therein, the light source for providing the light beam, a detector for detecting a light signal from a portion of the planar surface on which the plurality of capture molecules is bound, and an analysis module for receiving and analyzing the light signal from the detector; and C) one or more processing solutions; wherein the cartridge and the reader instrument cooperate such that the light beam is incident on the refractive volume in a plane parallel to and offset from the planar waveguide, and the light beam is focused at the planar surface at a non-zero, internal propagation angle relative to the planar surface for all light within the light beam, while illuminating a portion of the planar waveguide including the plurality of capture molecules thereby, if the sample includes a target analyte, the target analyte interacts with the plurality of capture molecules so as to produce the light signal capturable by the detector.

64. The kit of item 63, wherein the one or more processing solutions is selected from a group consisting of sample diluents solution, fluorescent conjugate solution, and wash solution.

65. The system of item 63 or 64, wherein the plurality of capture molecules include at least one molecule selected from the group consisting of a peptide, a polypeptide, a protein, an antibody, an antigen, a polysaccharide, sugar, an oligonucleotide, a polynucleotide, a synthetic molecule, an inorganic molecule, an organic molecule, and combinations thereof.

66. The system of item 63, 64 or 65, wherein the planar waveguide is formed of an optically transparent material selected from the group consisting of cyclic olefin polymer, cyclic olefin copolymer, polyolefin, polystyrene, acrylic, polymethylmethacrylate, and polycarbonate.

67. The kit of item 63, 64, 65 or 66, the sample containing antibodies and viral antigen, and wherein the cartridge and the reader instrument are configured to cooperate so as to detect both antibodies and viral antigen in the sample.

Changes may be made in the above methods and systems without departing from the scope hereof. It should thus be noted that the matter contained in the above description or shown in the accompanying drawings should be interpreted as illustrative and not in a limiting sense. The following claims are intended to cover generic and specific features described herein, as well as statements of the scope of the present method and system, which, as a matter of language, might be said to fall therebetween. For example, different capture molecules, printed protein site configurations, and other surface chemistries, from those described herein, may be contemplated. Additional suitable designs and materials for the integrated lens, other than those shown in the figures herein, may be incorporated into the planar waveguide without deviating from the spirit of the present disclosure. Additionally, other suitable types of illumination and detection may be used for further improved illumination uniformity and detection sensitivity.

Although each of the aforedescribed embodiments and examples have been illustrated with various components having particular respective orientations, it should be understood that the system as described in the present disclosure may take on a variety of specific configurations with the various components being located in a variety of positions and mutual orientations and still remain within the spirit and scope of the present disclosure. Furthermore, suitable equivalents may be used in place of or in addition to the various components, the function and use of such substitute or additional components being held to be familiar to those skilled in the art and are therefore regarded as falling within the scope of the present disclosure. Therefore, the present examples are to be considered as illustrative and not restrictive, and the present disclosure is not to be limited to the details given herein but may be modified within the scope of the appended claims.

What is claimed is:

1. A system for performing an assay on a sample to determine presence or absence of a target analyte in the sample, the system comprising:
   a cartridge having:
   (a) planar waveguide with a planar surface and a plurality of capture molecules bound thereto,
   (b) refractive volume for optically coupling a light beam to the planar waveguide, the refractive volume refracting the light beam such that all of the light beam focuses at a non-zero, internal propagation angle at the planar surface, and
   (c) sample chamber for containing the sample in contact with the plurality of capture molecules; and
   a reader instrument having:
   (a) light source for delivering the light beam parallel to the planar surface, and offset from the planar waveguide when incident on the refractive volume,
   (b) detector for detecting a light signal from a portion of the planar surface on which the plurality of capture molecules is bound,
   (c) analysis module for receiving and analyzing the light signal from the detector, and
   (d) a beam homogenizer.

2. The system of claim 1, the plurality of capture molecules comprising at least one molecule selected from the group consisting of a peptide, a polypeptide, a protein, an antibody, an antigen, a polysaccharide, sugar, an oligonucleotide, a polynucleotide, a synthetic molecule, an inorganic molecule, an organic molecule, and combinations thereof.

3. The system of claim 1, wherein the planar waveguide includes an optically transparent material selected from the group consisting of cyclic olefin polymer, cyclic olefin copolymer, polyolefin, polystyrene, acrylic, polymethylmethacrylate, and polycarbonate.

4. The system of claim 1, wherein the planar surface is modified using a process selected from the group consisting of plasma activation, chemical vapor deposition, liquid phase deposition, and surface polymerization of an activation chemistry, and combinations thereof.

5. The system of claim 1, further comprising a sample containing an antibody and an antigen, wherein the cartridge and the reader instrument cooperate so as to detect both the antibody and the antigen in the sample.

6. The system of claim 1, wherein the plurality of capture molecules includes an array arrangement including at least two reaction sites, each of the at least two reaction sites being formed by printing a composition onto the planar surface, the composition comprising at least one of the capture molecules.

7. The system of claim 6, wherein the at least two reaction sites contain different compositions.

8. The system of claim 6, wherein the at least two reaction sites include capture molecules selected from the group consisting of HIV antigens p17, p24, p31, gp41, p51, p55, p66, gp120, gp160, p41 Type O, p36 of HIV-2, antibodies against HIV antigen p24, and combinations thereof.

9. A method for performing an assay on a sample, the method comprising:
   introducing the sample into the sample chamber of the cartridge of claim 1;
   inserting the cartridge containing the sample, into the reader instrument of claim 1;
   using the light source, illuminating a portion of the planar waveguide at which the plurality of capture molecules are bound such that, if the sample includes a target analyte, the target analyte interacts with the plurality of capture molecules so as to produce a light signal;
   capturing the light signal; and
   analyzing the light signal,
   wherein illuminating includes
      directing the light beam at the refractive volume such that the light beam is incident on the refractive volume in a plane parallel to and offset from the planar waveguide, and
      refracting the light beam such that the light beam is focused at the planar surface at a non-zero, internal propagation angle relative to the planar surface for all light within the light beam.

10. The method of claim 9, wherein the plurality of capture molecules include at least one molecule selected from the group consisting of a peptide, a polypeptide, a protein, an antibody, an antigen, a polysaccharide, sugar, an oligonucleotide, a polynucleotide, a synthetic molecule, an inorganic molecule, an organic molecule, and combinations thereof.

11. The method of claim 9, further comprising modifying the planar surface using a process selected from the group consisting of plasma activation, chemical vapor deposition, liquid phase deposition, and surface polymerization of an activation chemistry, and combinations thereof.

12. The method of claim 9, the sample containing an antibody and an antigen, the method further comprising detecting both the antibody and the antigen in the sample.

13. The method of claim 12, wherein the plurality of capture molecules are selected from the group consisting of HIV antigens p17, p24, p31, gp41, p51, p55, p66, gp120, gp160, p41 Type O, p36 of HIV-2, antibodies against HIV antigen p24, and combinations thereof.

14. The method of claim 9, wherein providing the reader instrument further comprising homogenizing the light beam before the light beam is optically coupled to the planar waveguide.

15. A kit for performing a biochemical assay on a sample to determine presence or absence of a target analyte in the sample, the kit comprising:
- a cartridge having:
    - (a) planar waveguide with a planar surface and a plurality of capture molecules bound thereto,
    - (b) refractive volume for optically coupling a light beam to the planar waveguide, the refractive volume refracting the light beam such that all of the light beam focuses at a non-zero, internal propagation angle at the planar surface, and
    - (c) sample chamber for containing the sample in contact with the plurality of capture molecules;
- a reader instrument having:
    - (a) receiving mechanism for positioning the cartridge therein,
    - (b) light source for delivering the light beam parallel to the planar surface, and offset from the planar waveguide when incident on the refractive volume,
    - (c) detector for detecting a light signal from a portion of the planar surface on which the plurality of capture molecules is bound, and
    - (d) analysis module for receiving and analyzing the light signal from the detector, and
    - (e) a beam homogenizer; and
- one or more processing solutions for performing the assay on the sample in conjunction with the cartridge.

16. The kit of claim 15, wherein the one or more processing solutions is selected from a group consisting of sample diluents solution, fluorescent conjugate solution, and wash solution.

17. The kit of claim 15, the plurality of capture molecules including at least one molecule selected from the group consisting of a peptide, a polypeptide, a protein, an antibody, an antigen, a polysaccharide, sugar, an oligonucleotide, a polynucleotide, a synthetic molecule, an inorganic molecule, an organic molecule, and combinations thereof.

18. The kit of claim 15, wherein the planar waveguide includes an optically transparent material selected from the group consisting of cyclic olefin polymer, cyclic olefin copolymer, polyolefin, polystyrene, acrylic, polymethylmethacrylate, and polycarbonate.

19. The kit of claim 15, further comprising a sample containing an antibody and an antigen, and wherein the cartridge and the reader instrument are configured to cooperate so as to detect both the antibody and the antigen in the sample.

20. The system of claim 1, the cartridge further comprising one or more information indicators disposed on the cartridge, wherein at least one of the one or more information indicators represents at least one piece of information selected from the group consisting of cartridge parameters, cartridge type, print geometry, print layout, print lot, serial number, expiration date and combinations thereof.

21. The system of claim 1, wherein the plurality of capture molecules is immobilized to the first planar surface as an array comprising:
- at least two reaction sites, each of the at least two reaction sites being formed by printing a composition comprising at least one of the plurality of capture molecules onto the first planar surface, and,
- one or more positive control sites formed by printing, onto the first planar surface, a composition containing a control molecule that consistently binds to at least one analyte in a sample, at least one of the positive control sites being located at a distal end of the array farthest from the inlet port.

22. The kit of claim 15, the cartridge further comprising one or more information indicators disposed on the cartridge, wherein at least one of the one or more information indicators represents at least one piece of information selected from the group consisting of cartridge parameters, cartridge type, print geometry, print layout, print lot, serial number, expiration date and combinations thereof.

* * * * *